US010501418B2

(12) United States Patent
Aftab et al.

(10) Patent No.: US 10,501,418 B2
(45) Date of Patent: Dec. 10, 2019

(54) CRYSTALLINE SOLID FORMS OF N-{4-[(6,7-DIMETHOXYQUINOLIN-4-YL) OXY]PHENYL}-N'-(4-FLUOROPHENYL) CYCLOPROPANE-1,1-DICARBOXAMIDE, PROCESSES FOR MAKING, AND METHODS OF USE

(71) Applicant: Exelixis, Inc., South San Francisco, CA (US)

(72) Inventors: Dana T. Aftab, San Rafael, CA (US); Nathan Guz, Half Moon Bay, CA (US); Stephen Lau, South San Francisco, CA (US); Noel Hamill, Belfast (GB); Tracy Walker, Lurgan (GB); Jana Galbraith, Kinallen (GB); Simon Yau, Sunnyvale, CA (US); Khalid Shah, South San Francisco, CA (US)

(73) Assignee: Exelixis, Inc., Alameda, CA (US)

( * ) Notice: Subject to any disclaimer, the term of this patent is extended or adjusted under 35 U.S.C. 154(b) by 0 days.

(21) Appl. No.: 15/118,738

(22) PCT Filed: Feb. 16, 2015

(86) PCT No.: PCT/US2015/016052
§ 371 (c)(1),
(2) Date: Aug. 12, 2016

(87) PCT Pub. No.: WO2015/123639
PCT Pub. Date: Aug. 20, 2015

(65) Prior Publication Data
US 2017/0044106 A1    Feb. 16, 2017

Related U.S. Application Data

(60) Provisional application No. 61/939,985, filed on Feb. 14, 2014.

(51) Int. Cl.
C07D 215/00    (2006.01)
C07D 215/233    (2006.01)
C07D 215/22    (2006.01)

(52) U.S. Cl.
CPC ....... *C07D 215/233* (2013.01); *C07D 215/22* (2013.01); *C07B 2200/13* (2013.01)

(58) Field of Classification Search
CPC .................................................. C07D 215/233
USPC .............................................................. 546/153
See application file for complete search history.

(56) References Cited

U.S. PATENT DOCUMENTS

| 7,579,473 | B2 | 8/2009 | Bannen et al. |
| 7,977,345 | B2 | 7/2011 | Bannen et al. |
| 7,999,006 | B2 | 8/2011 | Lamb |
| 8,067,436 | B2 | 11/2011 | Bannen et al. |
| 8,178,532 | B2 | 5/2012 | Bannen et al. |
| 8,314,232 | B2 | 11/2012 | Deschamps et al. |
| 8,476,298 | B2 | 7/2013 | Bannen et al. |
| 8,497,284 | B2 | 7/2013 | Bannen et al. |
| 8,673,912 | B2 | 3/2014 | Cannon et al. |
| 8,877,776 | B2 * | 11/2014 | Brown ................. C07D 215/22 514/312 |
| 9,174,947 | B2 | 11/2015 | Bannen et al. |
| 9,365,516 | B2 | 6/2016 | Wilson et al. |
| 9,717,720 | B2 | 8/2017 | Wilson et al. |
| 9,724,342 | B2 | 8/2017 | Wilson et al. |
| 9,809,549 | B2 | 11/2017 | Brown et al. |
| 9,861,624 | B2 | 1/2018 | Aftab et al. |
| 9,969,692 | B2 | 5/2018 | Wilson et al. |
| 10,034,873 | B2 | 7/2018 | Wilson et al. |
| 10,039,757 | B2 | 9/2018 | Wilson et al. |
| 10,159,666 | B2 | 12/2018 | Aftab et al. |
| 10,166,225 | B2 | 1/2019 | Aftab et al. |
| 10,273,211 | B2 | 4/2019 | Aftab et al. |
| 2008/0161305 | A1 | 7/2008 | Forsyth et al. |
| 2009/0274693 | A1 | 11/2009 | Gilmer et al. |
| 2011/0077233 | A1 | 3/2011 | Bannen et al. |
| 2012/0070368 | A1 | 3/2012 | Bannen et al. |
| 2012/0184523 | A1 | 7/2012 | Bannen et al. |

(Continued)

FOREIGN PATENT DOCUMENTS

| CN | 103664776 | 3/2014 |
| CN | 103664778 | 3/2014 |

(Continued)

OTHER PUBLICATIONS

Byrn, et al., "Pharmaceutical Solids: A Strategic Approach to Regulatory Considerations." Pharmaceutical Research, 12: 945-954, 1995.
Caira, M. R., "Crystalline Polymorphism of Organic Compounds," Topics in Current Chemistry, vol. 198, pp. 163-208, 1998.
Database CA, Database accession No. 2015:316867, XP002739310, corresponding to CN 104370811 A.
Hancock, et al., "Characteristics and Significance of the Amorphous State in Pharmaceutical Systems", Journal of Pharmaceutical Sciences, vol. 86, No. 1, pp. 1-12, Jan. 1, 1997.
Hilfiker, R. (ed), "Polymorphism in the Pharmaceutical Industry", 2006.

(Continued)

*Primary Examiner* — Nizal Chandrakumar
(74) *Attorney, Agent, or Firm* — Honigman LLP; Heidi M. Berven; Jonathan P. O'Brien

(57) ABSTRACT

The invention relates to novel crystalline solid forms of the chemical compound N-{4-[(6,7-dimethoxyquinolin-4-yl) oxy]phenyl}-N'-(4-fluorophenyl) cyclopropane-1,1-dicarboxamide (Compound 1), and solvates thereof, including hydrates, that are useful for the treatment of cancer. Also disclosed are pharmaceutical compositions comprising the crystalline solid forms and processes for making the crystalline solid forms, as well as methods of using them for the treatment of cancer, particularly thyroid cancer, prostate cancer, hepatocellular cancer, renal cancer, and non-small cell lung carcinoma. The crystalline solid forms can be used to make the L-malate salt of cabozantinib.

11 Claims, 30 Drawing Sheets

(56) References Cited

U.S. PATENT DOCUMENTS

| | | |
|---|---|---|
| 2012/0252840 A1 | 10/2012 | Aftab et al. |
| 2012/0282179 A1 | 11/2012 | Aftab et al. |
| 2013/0030172 A1 | 1/2013 | Wilson et al. |
| 2013/0142790 A1 | 6/2013 | Gilmer et al. |
| 2013/0143881 A1 | 6/2013 | Cannon et al. |
| 2013/0150363 A1 | 6/2013 | Gilmer et al. |
| 2013/0197230 A1 | 8/2013 | Wilson et al. |
| 2013/0252940 A1 | 9/2013 | Bannen et al. |
| 2013/0252956 A1 | 9/2013 | Kallender et al. |
| 2013/0330377 A1 | 12/2013 | Wilson |
| 2013/0337015 A1 | 12/2013 | Wilson et al. |
| 2014/0057908 A1 | 2/2014 | Smith et al. |
| 2014/0057943 A1 | 2/2014 | Smith et al. |
| 2014/0066444 A1 | 3/2014 | Smith et al. |
| 2014/0121239 A1 | 5/2014 | Aftab |
| 2014/0155396 A1 | 6/2014 | Bannen et al. |
| 2014/0179736 A1 | 6/2014 | Schwab et al. |
| 2014/0200242 A1 | 7/2014 | Wilson et al. |
| 2014/0221372 A1 | 8/2014 | Kulkarni et al. |
| 2014/0228401 A1 | 8/2014 | Aftab et al. |
| 2014/0256938 A1 | 9/2014 | Wilson et al. |
| 2014/0302012 A1 | 10/2014 | Aftab et al. |
| 2014/0323522 A1 | 10/2014 | Aftab et al. |
| 2015/0057310 A1 | 2/2015 | Brown et al. |
| 2015/0133494 A1 | 5/2015 | Aftab et al. |
| 2015/0196545 A1 | 7/2015 | Aftab et al. |
| 2015/0202196 A1 | 7/2015 | Bannen et al. |
| 2015/0238477 A1 | 8/2015 | Aftab |
| 2015/0376133 A1 | 12/2015 | Bannen et al. |
| 2016/0000772 A1 | 1/2016 | Aftab et al. |
| 2016/0022662 A1 | 1/2016 | Decillis et al. |
| 2016/0031818 A1 | 2/2016 | Aftab et al. |
| 2016/0051532 A1 | 2/2016 | Aftab et al. |
| 2016/0082019 A1 | 3/2016 | Sweeney et al. |
| 2016/0185725 A1 | 6/2016 | Bannen et al. |
| 2016/0220554 A1 | 8/2016 | Smith et al. |
| 2016/0229805 A1 | 8/2016 | Wilson et al. |
| 2017/0057921 A1 | 3/2017 | Wilson et al. |
| 2017/0143689 A1 | 5/2017 | Wilson et al. |
| 2017/0217896 A1 | 8/2017 | Donnelly et al. |
| 2017/0224670 A1 | 8/2017 | Smalley |
| 2017/0224672 A1 | 8/2017 | Aftab et al. |
| 2017/0266178 A1 | 9/2017 | Wilson et al. |
| 2017/0275251 A1 | 9/2017 | Brown et al. |
| 2017/0355678 A1 | 12/2017 | Bannen et al. |
| 2018/0002289 A1 | 1/2018 | Brown et al. |
| 2018/0037552 A1 | 2/2018 | Brown et al. |
| 2018/0230100 A1 | 8/2018 | Wilson et al. |
| 2018/0311229 A1 | 11/2018 | Wilson et al. |
| 2019/0030021 A1 | 1/2019 | Wilson et al. |
| 2019/0076420 A1 | 3/2019 | Aftab et al. |
| 2019/0091215 A1 | 3/2019 | Aftab et al. |
| 2019/0151302 A1 | 5/2019 | Aftab et al. |

FOREIGN PATENT DOCUMENTS

| | | |
|---|---|---|
| CN | 104370811 | 2/2015 |
| WO | 2010083414 | 7/2010 |
| WO | 2012009722 | 1/2012 |

OTHER PUBLICATIONS

International Search Report for PCT/US2015/016052, dated May 26, 2015.
Banker, et al., eds., Modern Pharmaceutics Fourth Edition, pp. 172-174, 2002.
Bavin, et. al, "Polymorphism in Process Development." Chemistry & Industry, pp. 527-529, Aug. 21, 1989.
Hancock, et al., "Molecular Mobility of Amorphous Pharmaceutical Solids Below their Glass Transition Temperatures", Pharmaceutical Research, vol. 12, No. 6, pp. 799-806, 1995.
International Conference on Harmonisation of Technical Requirements for Registration of Pharmaceuticals for Human Use, "Specifications: Test Procedures and Acceptance Criteria for New Drug Substances and New Drug Products: Chemical Substances." ICH Harmonised Tripartite Guideline Q&A Oct. 6. 1999.
Jozwiakowski, Michael J., "Alteration of the Solid State of the Drug Substance: Polymorphs, Solvates, and Amorphous Forms", Water-Insoluble Drug Formation, Rong Liu, ed., pp. 525-561, 2000.
Kurzrock R et al. "379 POSTER A phase I study of XL 184, a MET, VEGFR2, and RET kinase inhibitor, administered orally to patients (pts) with advanced malignancies, including a subgroup of pts with medullary thyroid cancer (MTC)." Eropean journal of cancer. supplement, vol. 6, No. 12, Oct. 1, 2008, 119.

* cited by examiner

XRPD Pattern of Amorphous Compound I Prepared by Lyophilisation

FIG. 17 TG/DTA Thermogram for Compound I Form XXVIII

¹H NMR of Compound I Form XXVIII

¹H NMR of Compound I Form XXXI

CRYSTALLINE SOLID FORMS OF N-{4-[(6,7-DIMETHOXYQUINOLIN-4-YL)OXY]PHENYL}-N'-(4-FLUOROPHENYL)CYCLOPROPANE-1,1-DICARBOXAMIDE, PROCESSES FOR MAKING, AND METHODS OF USE

PRIORITY CLAIM

This application is a 35 U.S.C. § 371 United States National Phase Application of, and claims priority to, PCT Application No.: PCT/US2015/16052, filed Feb. 16, 2015, which claims the benefit under 35 U.S.C. § 119 of U.S. Provisional Application Ser. No. 61/939,985, filed Feb. 14, 2014. The entire contents of both of the aforementioned applications are incorporated herein by reference in their entireties.

FIELD OF THE INVENTION

The invention relates to novel crystalline solid forms of the chemical compound N-{4-[(6,7-dimethoxyquinolin-4-yl)oxy]phenyl}-N'-(4-fluorophenyl) cyclopropane-1,1-dicarboxamide, and solvates thereof, including hydrates, that are useful for the treatment of cancer. Also disclosed are pharmaceutical compositions comprising the crystalline solid forms and processes for making the crystalline solid forms, as well as methods of using them for the treatment of cancer, particularly thyroid cancer, prostate cancer, hepatocellular cancer, renal cancer, and non-small cell lung carcinoma.

BACKGROUND OF THE INVENTION

Commonly assigned PCT Patent Publication No. WO 2005/030140, incorporated by reference herein in its entirety, discloses novel inhibitors of multiple receptor tyrosine kinases (RTKs) implicated in tumor growth and angiogenesis, pathologic bone remodeling, and metastatic progression of cancer. In particular, the compound N-{4-[(6,7-dimethoxyquinolin-4-yl)oxy]phenyl}-N'-(4-fluorophenyl) cyclopropane-1,1-dicarboxamide is specifically described in WO 2005/030140 as an RTK inhibitor. The chemical structure of N-{4-[(6,7-dimethoxyquinolin-4-yl)oxy]phenyl}-N'-(4-fluorophenyl) cyclopropane-1,1-dicarboxamide is represented by Compound 1.

Compound 1

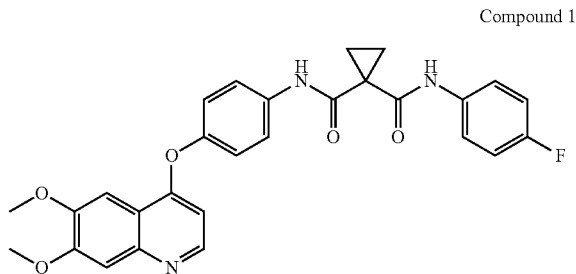 [SMILES: COc1cc2nccc(Oc3ccc(NC(=O)C4(C(=O)Nc5ccc(F)cc5)CC4)cc3)c2cc1OC]

Compound 1 was found to have an enzyme Ret $IC_{50}$ value of about 5.2 nM (dihydrate) and an enzyme c-Met $IC_{50}$ value of about 1.3 nM (dihydrate). The assay that was used to measure this c-Met activity is described in paragraph [0458] in WO2005/030140.

During initial development experiments, Compound 1 (a free base) was found to be a BCS class II compound having low solubility and high permeability. Because Compound 1 was observed to have low solubility in water, it was initially considered unsuitable for solid oral dosage development, and hence the pharmaceutical development focused on finding a salt with suitable hygroscopicity, thermal stability, chemical stability, physical stability, and solubility.

The malate salt of the Compound 1, as described in WO 2010/083414, the entire contents of which is incorporated by reference, was subsequently identified as providing an acceptable combination of crystallinity, solubility, and stability as compared to cabozantinib free base. On Nov. 29, 2012, the S-malate salt of N-{4-[(6,7-dimethoxyquinolin-4-yl)oxy]phenyl}-N'-(4-fluorophenyl) cyclopropane-1,1-dicarboxamide (also known as cabozantinib or COMETRIQ®) was approved by the United States Food and Drug Administration for the treatment of progressive, metastatic medullary thyroid cancer (MTC). In December 2013, the European Committee for Medicinal Products for Human Use (CHMP), issued a positive opinion on the Marketing Authorization Application (MAA), submitted to the European Medicines Agency, or EMA, for COMETRIQ for the proposed indication of progressive, unresectable, locally advanced, or metastatic MTC. Cabozantinib is being evaluated in a broad development program, including ongoing phase 3 pivotal trials in metastatic renal cell cancer (RCC), and advanced hepatocellular cancer (HCC).

Besides therapeutic efficacy, the Applicant continues to endeavor to provide suitable form(s) of Compound 1 that have favorable properties related to processing, manufacturing, storage stability, and/or usefulness as a drug. Accordingly, the discovery of new crystalline solid forms of Compound 1 that possesses some or all of these desired properties remains vital to drug development. Thus, disclosed herein are novel crystalline solid forms of Compound 1 that may be used in pharmaceutical compositions for the treatment of proliferative diseases such as cancer.

SUMMARY OF THE INVENTION

These and other needs are met by the present invention, which is directed to novel crystalline solid forms of Compound 1, as well as pharmaceutical compositions containing, methods for using, and processes for making such crystalline solid forms. The crystalline solid forms include free base crystalline solid forms, as well as solvate, including hydrate, crystalline solid forms. Among other uses, crystalline solid forms of Compound 1 are useful for preparing pharmaceutical compositions expected to have utility in treating cancer. Accordingly, one aspect of the invention pertains to a pharmaceutical composition comprising a pharmaceutically acceptable carrier and a therapeutically effective amount of a solid form of Compound 1.

As indicated previously, Compound 1 inhibits multiple receptor tyrosine kinases (RTKs) implicated in tumor growth and angiogenesis, pathologic bone remodeling, and metastatic progression of cancer. Accordingly, crystalline solid forms of the Compound 1 are useful for treating cancer. Thus, another aspect of the invention pertains to a method for treating cancer comprising administering to a subject a therapeutically effective amount of a solid form of Compound 1 as disclosed herein. The invention is also directed to processes for preparing crystalline solid forms of Compound 1.

As a further aspect, any of the crystalline solid forms disclosed herein can be used to make pharmaceutically acceptable salts of N-{4-[(6,7-dimethoxyquinolin-4-yl)oxy]

phenyl}-N'-(4-fluorophenyl) cyclopropane-1,1-dicarboxamide, including its S-malate salt, which is sold as cabozantinib.

BRIEF DESCRIPTION THE DRAWINGS

Various aspects of the present invention are illustrated by reference to the following drawings.

DETAILED DESCRIPTION OF THE INVENTION

Definitions

Figure 1:
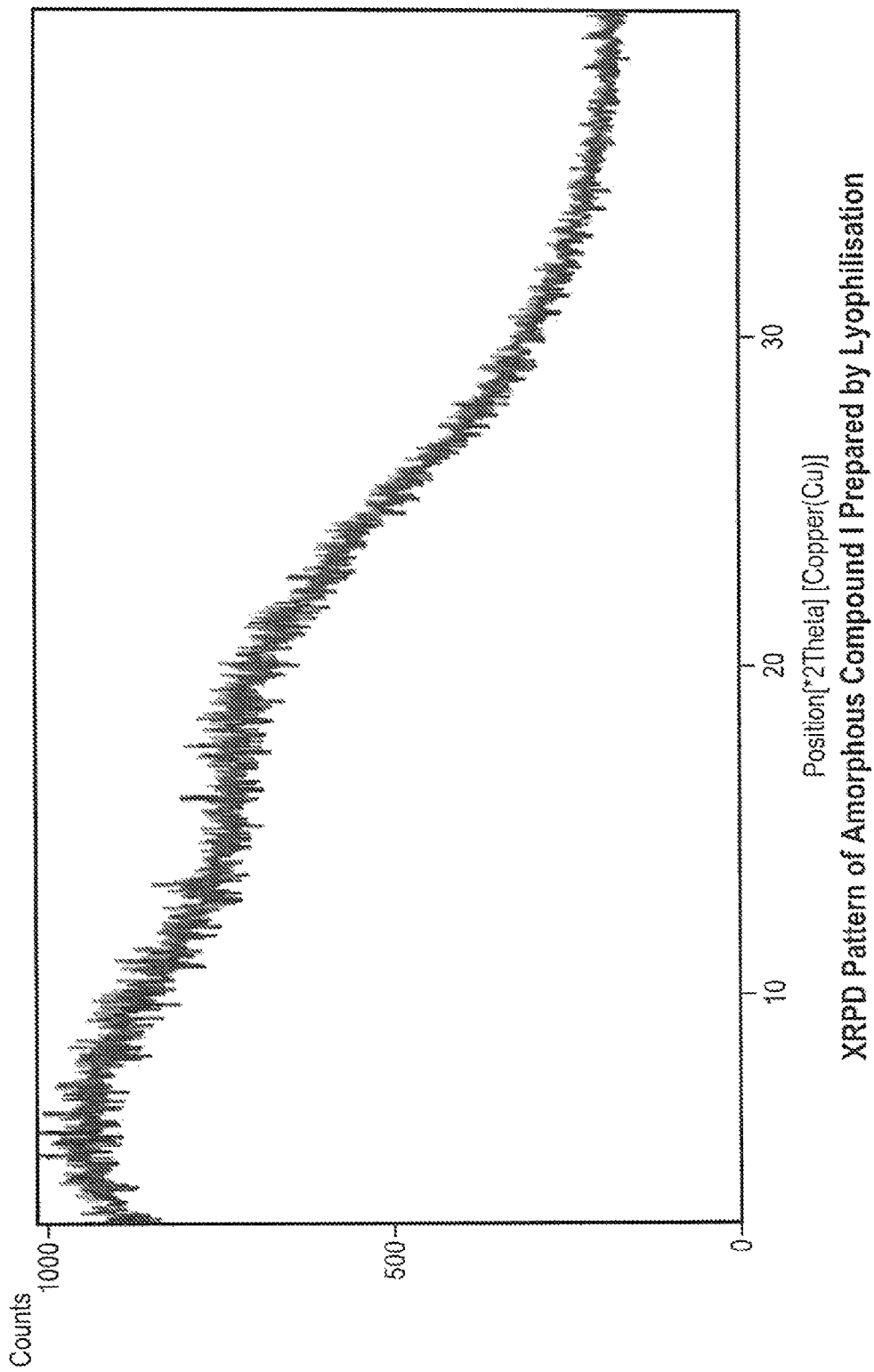
FIG. 1 shows the experimental x-ray powder diffraction (XRPD) pattern of amorphous Compound 1 prepared by lyophilisation.

When describing the compounds, compositions, methods, and processes of the invention, the following terms have the following meanings unless otherwise indicated.

The term "solvate" means a complex or aggregate formed by one or more molecules of a solute, i.e., a crystalline Compound 1, and one or more molecules of a solvent. Such solvates typically have a substantially fixed molar ratio of solute and solvent. This term also includes clathrates, including clathrates with water. Representative solvents include, for example, water, methanol, ethanol, isopropanol, acetic acid, and the like. When the solvent is water, the solvate formed is a hydrate.

"Therapeutically effective amount" means an amount sufficient to effect treatment when administered to a subject in need of treatment. For example, a therapeutically effective amount for, as described below. "The amount of a compound of the invention which constitutes a "therapeutically effective amount" will vary depending on the compound, the disease state and its severity, the age of the subject to be treated, and the like. The therapeutically effective amount can be determined routinely by one of ordinary skill in the art taking into consideration his own knowledge and to this disclosure. Thus, a "therapeutically effective amount" of Compound 1 refers to an amount sufficient to treat a subject suffering from any of a variety of cancers associated with abnormal cell proliferation and angiogenesis. A therapeutically effective amount according to this disclosure is an amount therapeutically useful for the treatment or prevention of the disease states and disorders discussed herein. Compound 1 (including the solid state forms disclosed herein) possess therapeutic activity to inhibit, regulate, and/or modulate the signal transduction of kinases such as described in WO2005-030140.

"Treating" or "treatment" as used herein means the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state.

The term "pharmaceutically acceptable" refers to a material that is not biologically or otherwise undesirable. For example, the term "pharmaceutically acceptable carrier" refers to a material that can be incorporated into a composition and administered to a subject without causing undesirable biological effects or interacting in a deleterious manner with other components of the composition. Such pharmaceutically acceptable materials typically have met the required standards of toxicological and manufacturing testing and include those materials identified as suitable inactive ingredients by the U.S. Food and Drug Administration.

The term "dosage form" refers to a physically discrete unit suitable for dosing a subject, i.e., each unit containing a predetermined quantity of a compound of the invention calculated to produce the desired therapeutic effect either alone or in combination with one or more additional units. For example, such unit dosage forms may be capsules, tablets, pills, and the like.

As used herein, "amorphous" refers to a solid form of a molecule and/or ion that is not crystalline. An amorphous solid does not display a definitive X-ray diffraction pattern with sharp maxima.

As used herein, the term "substantially pure" means the solid form of Compound 1 referred to contains at least about 90 weight percent based on the weight of such solid form. The term "at least about 90 weight percent," while not intending to limit the applicability of the doctrine of equivalents to the scope of the claims, includes, but is not limited to, for example, about 90, about 91, about 92, about 93, about 94, about 95, about 96, about 97, about 98, about 99, and about 100 weight percent, based on the weight of the solid form referred to. The remainder of the solid form of Compound 1 may comprise other solid form(s) of Compound 1 and/or reaction impurities and/or processing impurities that arise, for example, when the crystalline form is prepared. The presence of reaction impurities and/or processing impurities may be determined by analytical techniques known in the art, such as, for example, chromatography, nuclear magnetic resonance spectroscopy, mass spectroscopy, and/or infrared spectroscopy.

Embodiments

This disclosure relates to solid solvate forms of Compound 1, as well as unsolvated (otherwise known as "anhydrous" or "free base") crystalline solid forms of Compound 1. The forms disclosed herein each represent separate aspects of the disclosure. Although the crystalline solid forms are described herein, the invention also relates to novel compositions containing the disclosed crystalline solid forms. Therapeutic uses of the crystalline solid forms described as well as therapeutic compositions containing them represent separate aspects of the disclosure. The techniques used to characterize the crystalline solid forms are described in the examples below. These techniques, alone or in combination, may be used to characterize the crystalline forms disclosed herein. The crystalline solid forms may be also characterized by reference to the disclosed figures.

Crystalline Solid Forms of Compound 1

This disclosure relates to crystalline solid forms of Compound 1. The crystalline solid forms include:

A crystalline dihydrate form of Compound designated as Compound 1 Form I;
A crystalline solvate form of Compound designated as Compound 1 Form II;
A crystalline anhydrous ("free base") form of Compound 1 designated as Compound 1 Form III;
A crystalline anhydrous ("free base") form of Compound 1 designated as Compound 1 Form XXVIII;
A crystalline anhydrous ("free base") form of Compound 1 designated as Compound 1 Form XXX; and
A crystalline dihydrate form of Compound 1 designated as Compound 1 Form XXXI.

The names used herein to characterize a specific form, e.g. "Form I," etc., are not to be limited so as to exclude any other substance possessing similar or identical physical and chemical characteristics, but rather such names are used as mere identifiers that are to be interpreted in accordance with the characterization information presented herein.

Each form of Compound 1 is a separate aspect of the disclosure. Mixtures of the crystalline solid forms of Compound 1 are another aspect of the disclosure. Compound 1 Forms have various desirable properties for development.

Figure 2:
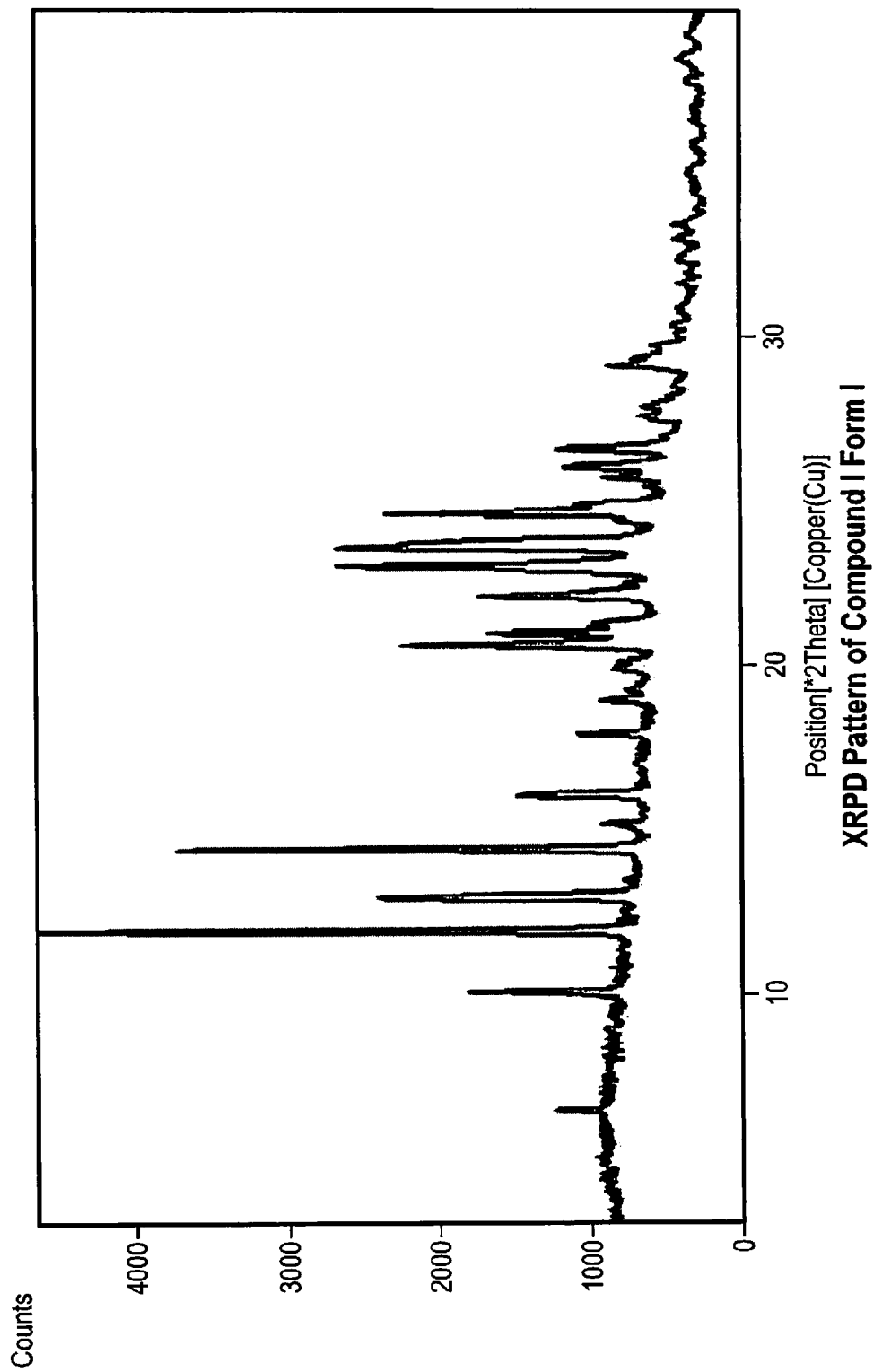
FIG. 2 shows the experimental x-ray powder diffraction (XRPD) pattern for Compound 1 Form I.

Compound 1 Form I may be characterized by at least one of the following:
(i) an x-ray powder diffraction pattern (CuKα) comprising two or more peaks as depicted in FIG. 2, wherein measurement of the crystalline form is at an ambient room temperature; and
(ii) an x-ray powder diffraction (XRPD) spectrum substantially in accordance with the pattern shown in FIG. 2.

Compound 1 Form I may be characterized by an x-ray powder diffraction pattern (CuKα) comprising peaks at 10.1, 11.9, 12.9, 14.4, 16.0, 23.0, 23.6, and 24.7 (°2θ±0.2 °2θ). In another embodiment, Compound 1 Form I may be characterized by an x-ray powder diffraction pattern (CuKα) comprising peaks at 10.1, 11.9, 12.9, 14.4, 16.0, and 23.6 (°2θ±0.2 °2θ). In another embodiment, Compound 1 Form I may be characterized by an x-ray powder diffraction pattern (CuKα) comprising peaks at 10.1 and 12.9 (°2θ±0.2 °2θ). In a further embodiment, Compound 1 Form I may be characterized by an x-ray powder diffraction pattern (CuKα) comprising peaks at 11.9, 14.4, 16.0, and 23.6 (°2θ±0.2 °2θ).

Figure 3:
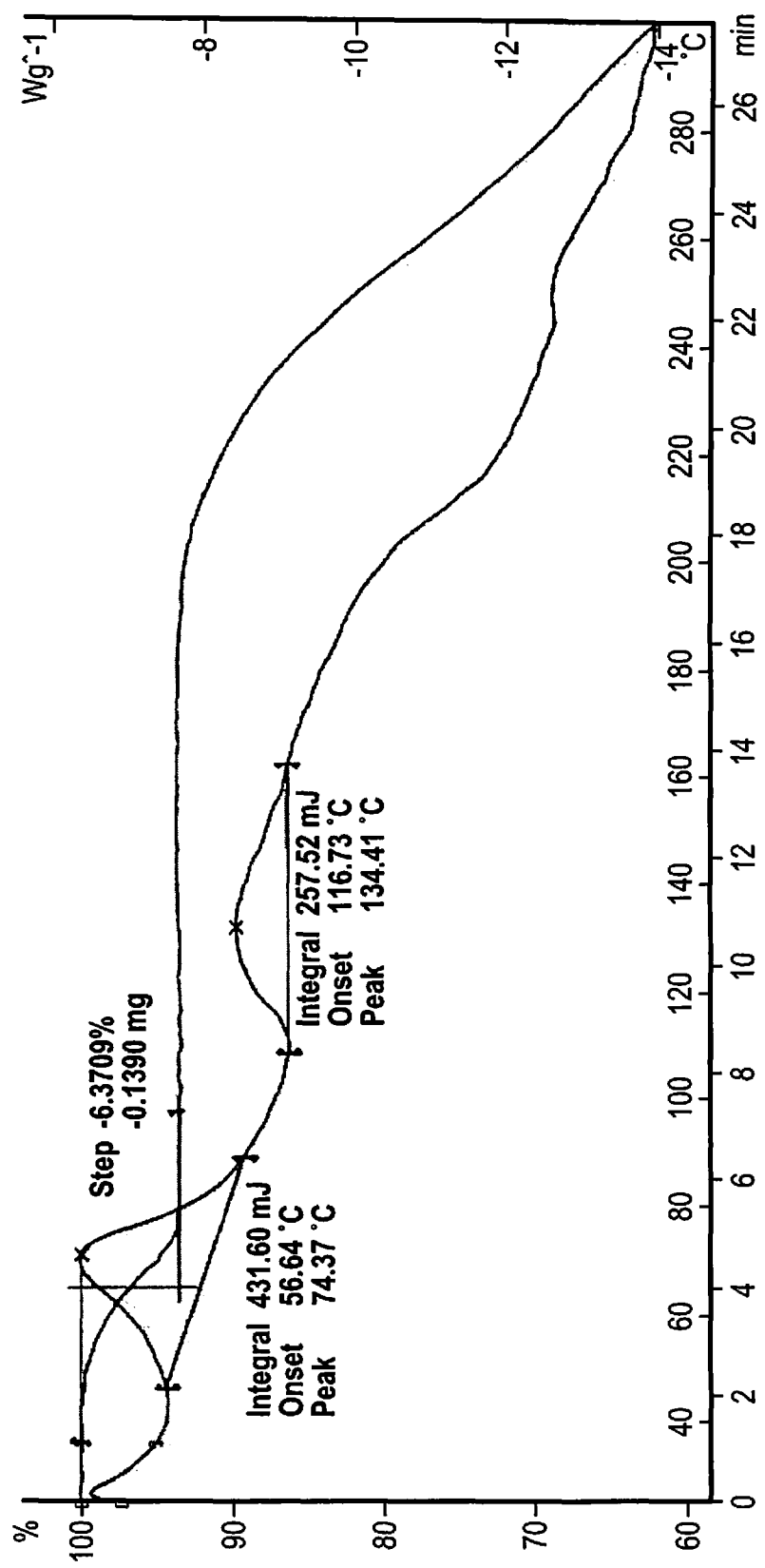
FIG. 3 shows the thermogravimetric differential thermal analysis (TG/DTA) thermogram for Compound 1 Form I, run from 30-300° C. at 10° C./min.

Other solid state properties which may be used to characterize Compound 1 Form I are shown in the FIGS. (FIGS. 3-6) and discussed in the examples below. For example, thermogravimetric/differential analysis (TG/DTA) of Compound 1 Form I showed weight loss of 6.5 percent, from 25-80° C., corresponding to the loss of 1.92 moles of water, indicating that Compound 1 Form I is a dihydrate (FIG. 3). The hygroscopicity and the sorption properties of Compound 1 Form I indicated very small weight gain between 40% RH and 90% RH, indicating that Compound 1 Form I is stable and non-hygroscopic at higher humidity.

Compound 1 Form I can be prepared by agitating a mixture of Compound 1 Form I or amorphous Compound 1 and THF at ambient temperature until the Compound 1 is dissolved. Water is then added portionwise, and the mixture is stirred for a sufficient time. The solid Compound 1 Form I is collected and dried.

Figure 7:
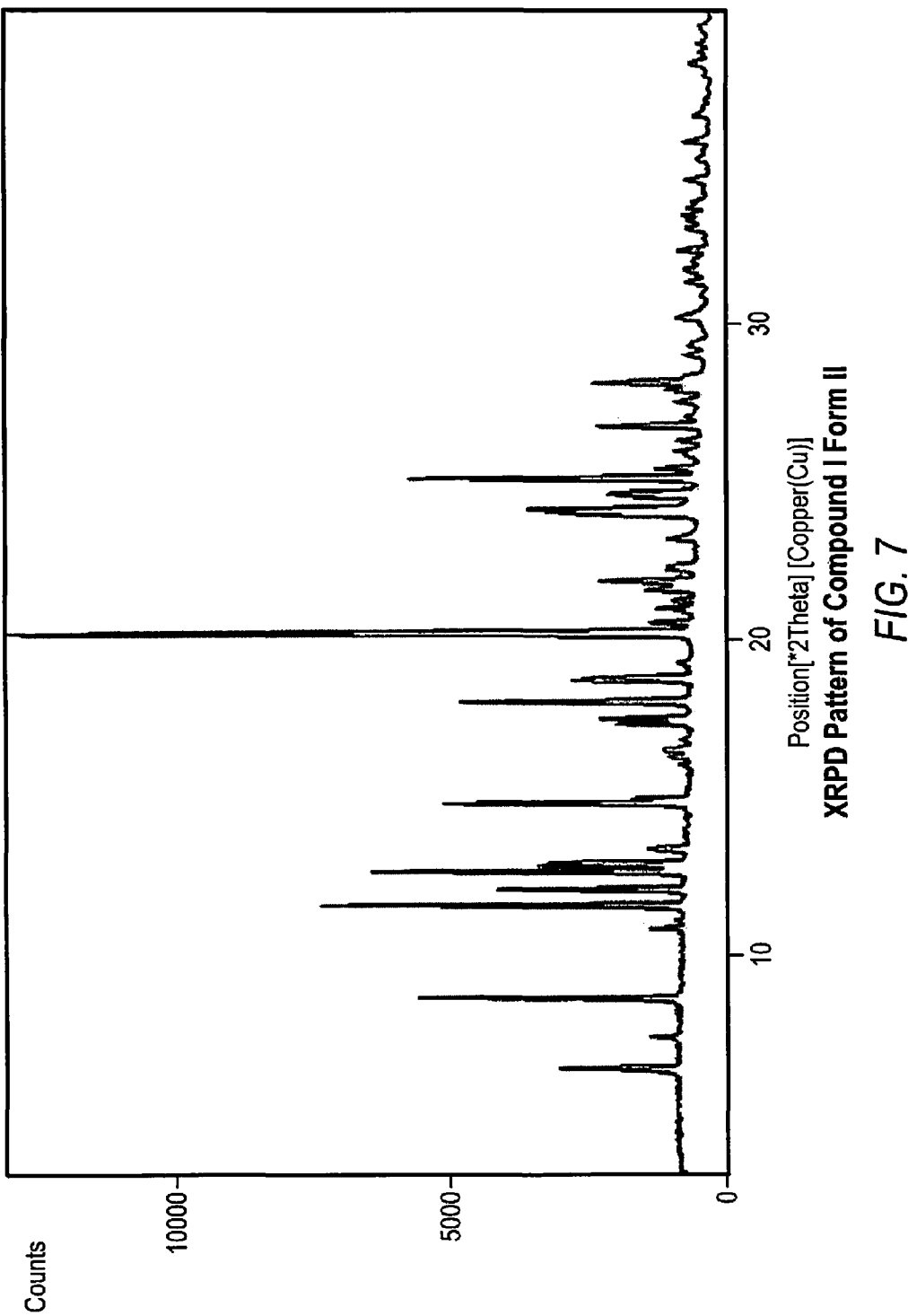
FIG. 7 shows the experimental x-ray powder diffraction (XRPD) pattern for Compound 1 Form II.

Compound 1 Form II may be characterized by at least one of the following:
(i) an x-ray powder diffraction pattern (CuK α) comprising two or more peaks as depicted in FIG. 7, wherein measurement of the crystalline form is at an ambient room temperature; and
(ii) an x-ray powder diffraction (XRPD) spectrum substantially in accordance with the pattern shown in FIG. 7.

In on embodiment, Compound 1 Form II may be characterized by an x-ray powder diffraction pattern (CuKα) comprising peaks at 6.4, 11.6, 12.1, 12.6, 12.9, 14.8, 14.9, 18.0, 18.8, and 20.2 (°2θ±0.2 °2θ). In another embodiment, Compound 1 Form II may be characterized by an x-ray powder diffraction pattern (CuKα) comprising peaks at 6.4, 11.6, 12.1, 12.6, 12.9, 14.8, 14.9, and 20.2 (°2θ±0.2 °2θ). In another embodiment, Compound 1 Form II may be characterized by an x-ray powder diffraction pattern (CuKα)

comprising peaks at 11.6, 12.1, 12.6, 12.9, and 14.9 (°2θ±0.2 °2θ). In a further embodiment, Compound 1 Form II may be characterized by an x-ray powder diffraction pattern (CuKα) comprising peaks at 6.4, 8.6, 14.9, and 20.2 (°2θ±0.2 °2θ).

Figure 8:
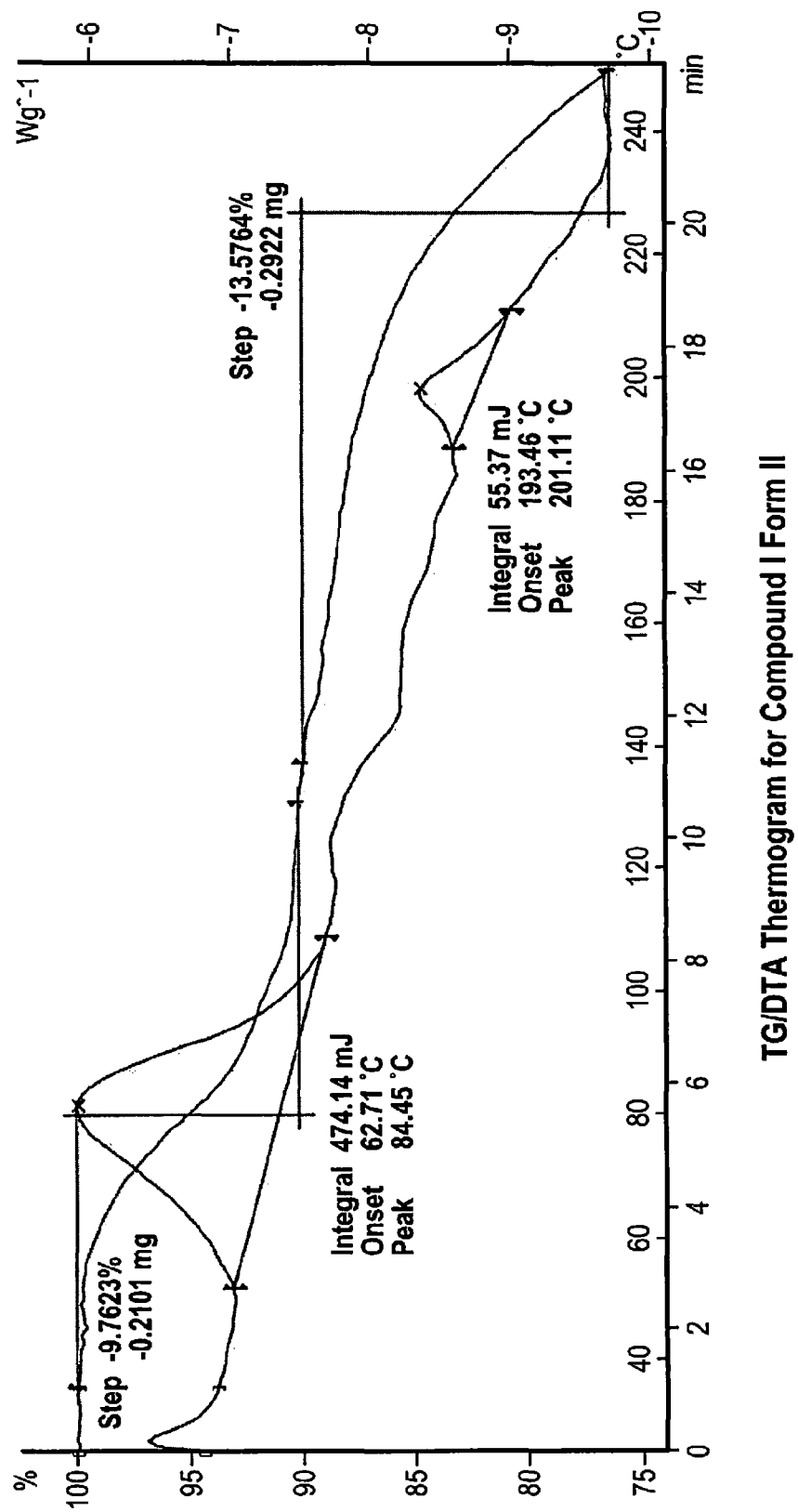
FIG. 8 shows the thermogravimetric differential thermal analysis (TG/DTA) thermogram for crystalline Compound 1 Form II, run from 30-300° C. at 10° C./min.
Figure 9:
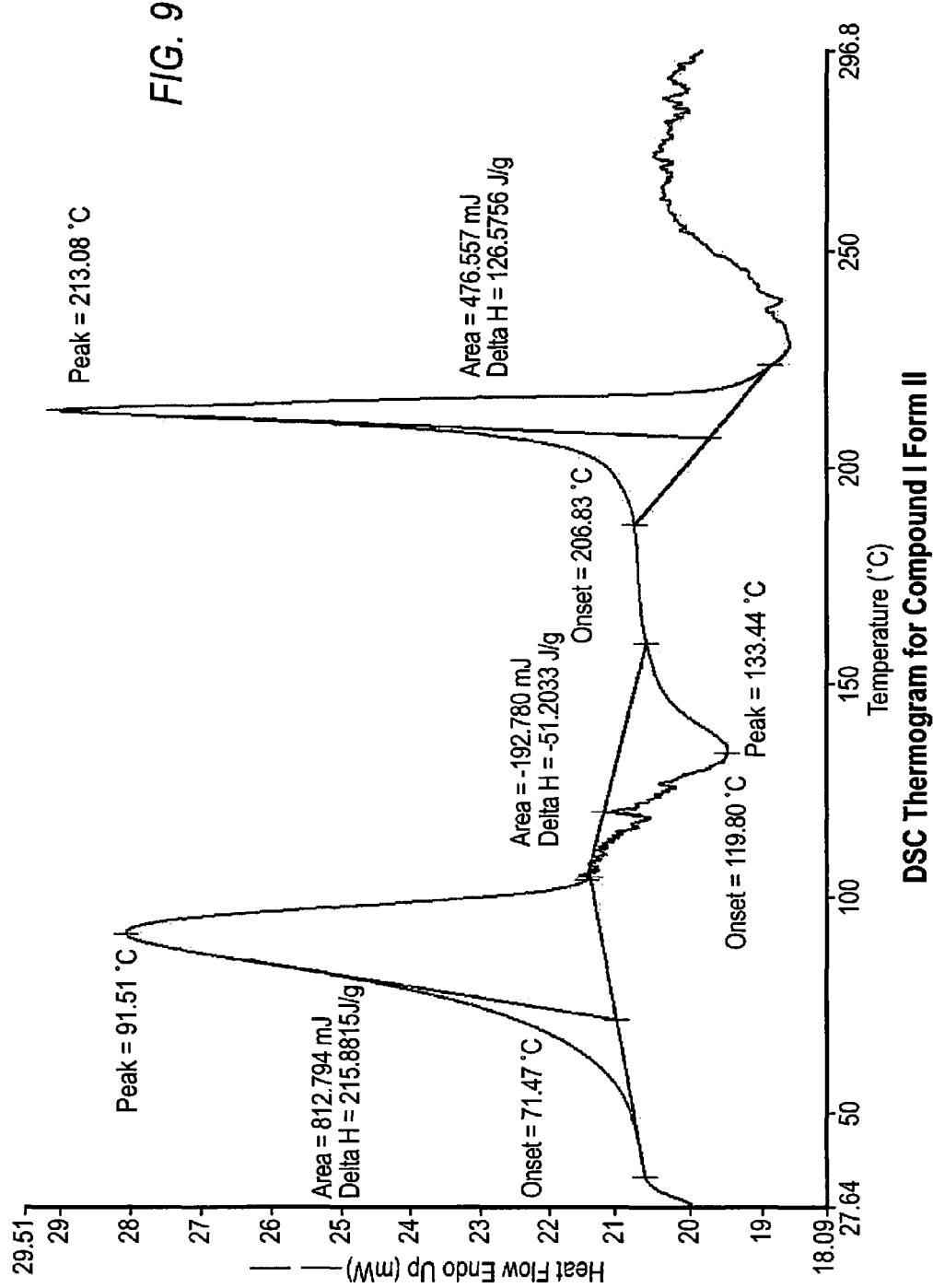
FIG. 9 shows the differential scanning calorimetry (DSC) thermogram for Compound 1 Form II, run from 30-300° C. at 10° C./min.
Figure 10:
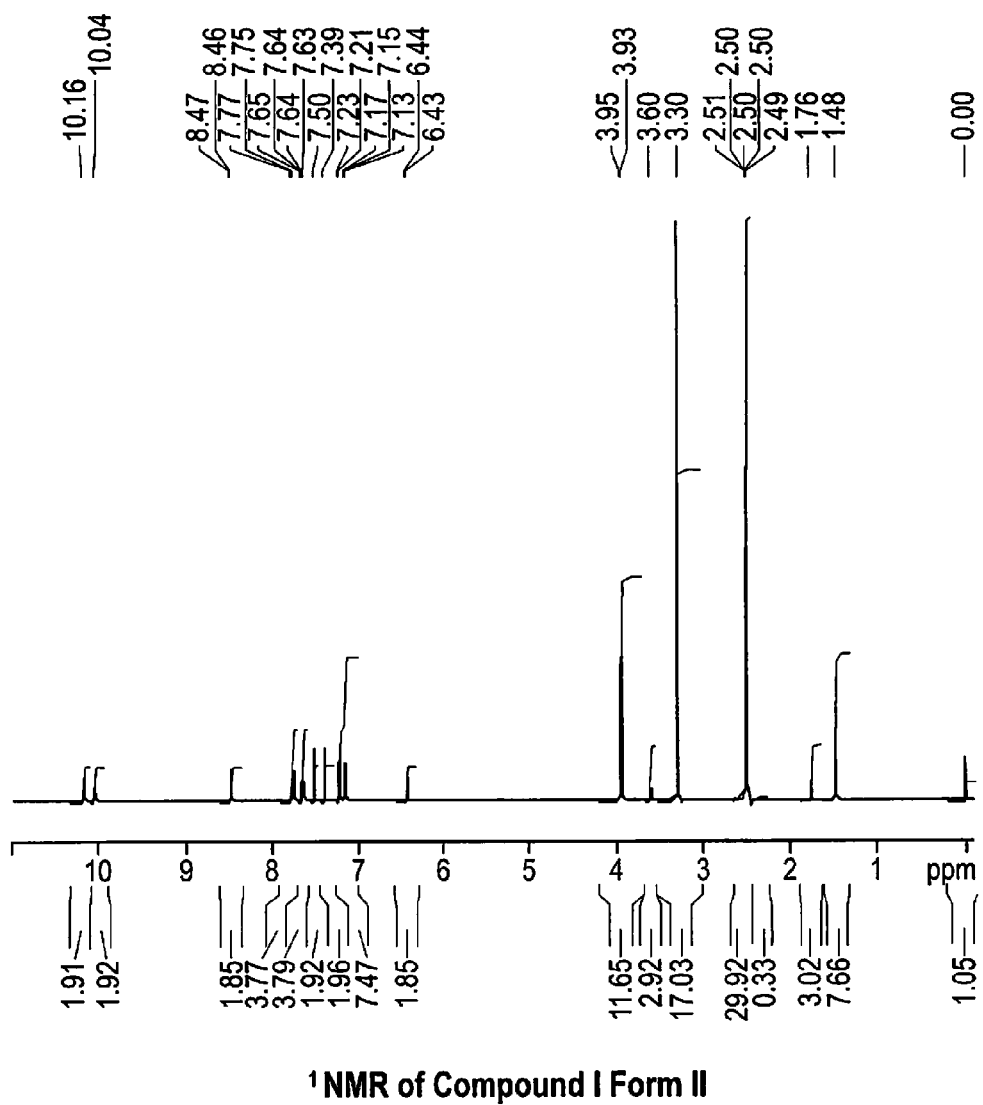
FIG. 10 shows the $^1$H nuclear magnetic resonance (NMR) spectrum for Compound 1 Form II.

Other solid state properties which may be used to characterize Compound 1 Form II are shown in the FIGS. (FIGS. 8-10) and discussed in the examples below. For example, thermogravimetric/differential analysis (TG/DTA) of Compound 1 Form II showed weight loss of 9.8 percent, attributable to the loss of a mixture of tetrahydrofuran (THF) and water (FIG. 8).

Compound 1 Form II can be prepared by agitating a mixture of Compound 1 Form I and THF at ambient temperature until the Compound 1 Form I is dissolved. Water is then added portionwise, and the mixture is stirred for a sufficient time. The solid Compound 1 Form II is collected and dried.

Figure 11:
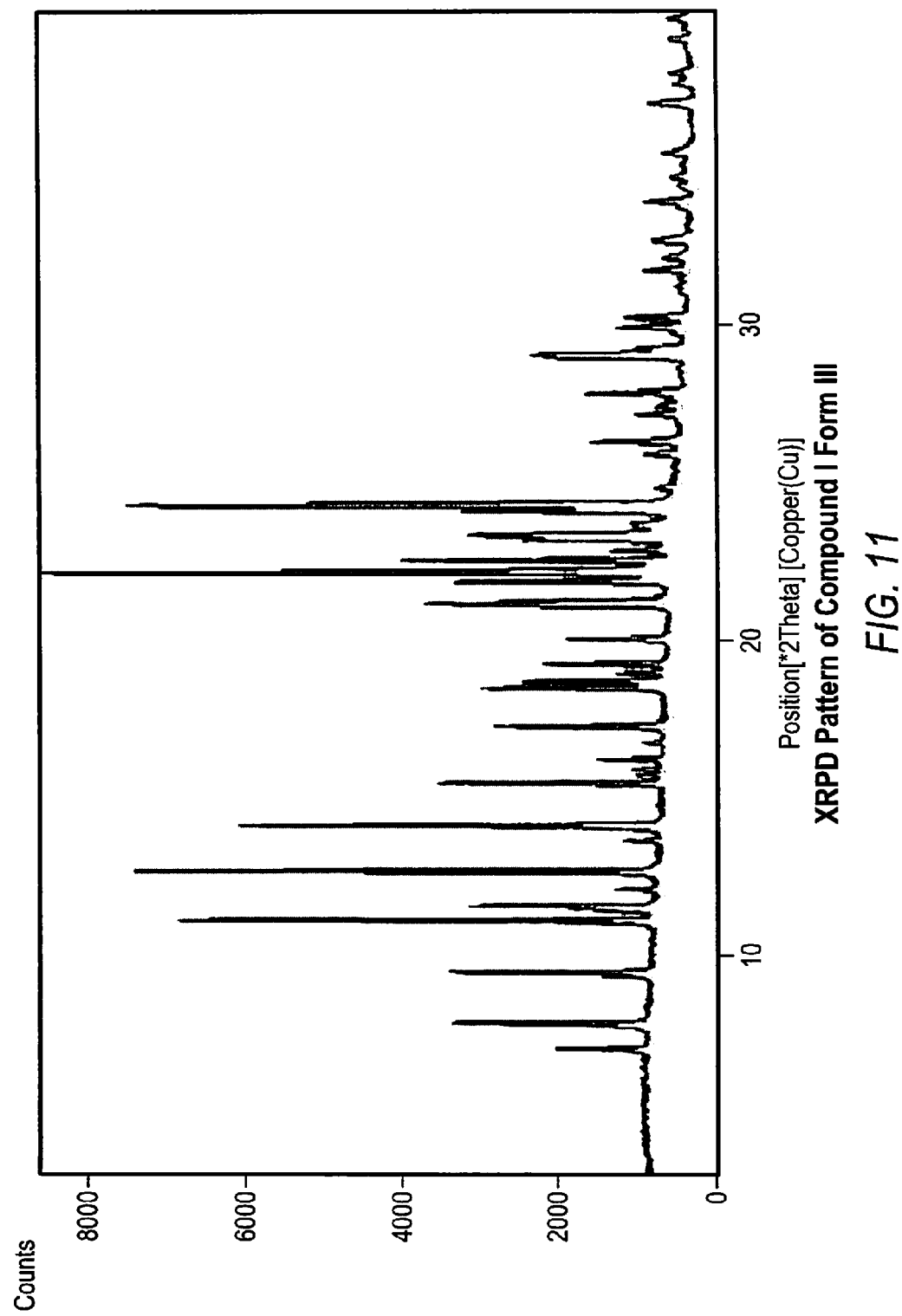
FIG. 11 shows the experimental x-ray powder diffraction (XRPD) pattern for Compound 1 Form III.

Compound 1 Form III may be characterized by at least one of the following:

(i) an x-ray powder diffraction pattern (CuKα) comprising two or more peaks as depicted in FIG. 11, wherein measurement of the crystalline form is at an ambient room temperature; and (ii) an x-ray powder diffraction (XRPD) spectrum substantially in accordance with the pattern shown in FIG. 11.

In one embodiment, Compound 1 Form III may be characterized by an x-ray powder diffraction pattern (CuKα) comprising peaks at 7.0, 7.8, 9.4, 11.1, 12.6, 14.1, 15.5, 17.3 22.3, and 24.3 (°2θ±0.2 °2θ). In another embodiment, Compound 1 Form III may be characterized by an x-ray powder diffraction pattern (CuKα) comprising peaks at 7.0, 7.8, 9.4, 11.1, 12.6, 14.1, 22.3, and 24.3 (°2θ±0.2 °2θ). In another embodiment, Compound 1 Form III may be characterized by an x-ray powder diffraction pattern (CuKα) comprising peaks at 9.4, 12.6, 22.3, and 24.3 (°2θ±0.2 °2θ). In a further embodiment, Compound 1 Form III may be characterized by an x-ray powder diffraction pattern (CuKα) comprising peaks at 7.0, 7.8, 11.1, and 14.1 (°2θ±0.2 °2θ).

Figure 12:
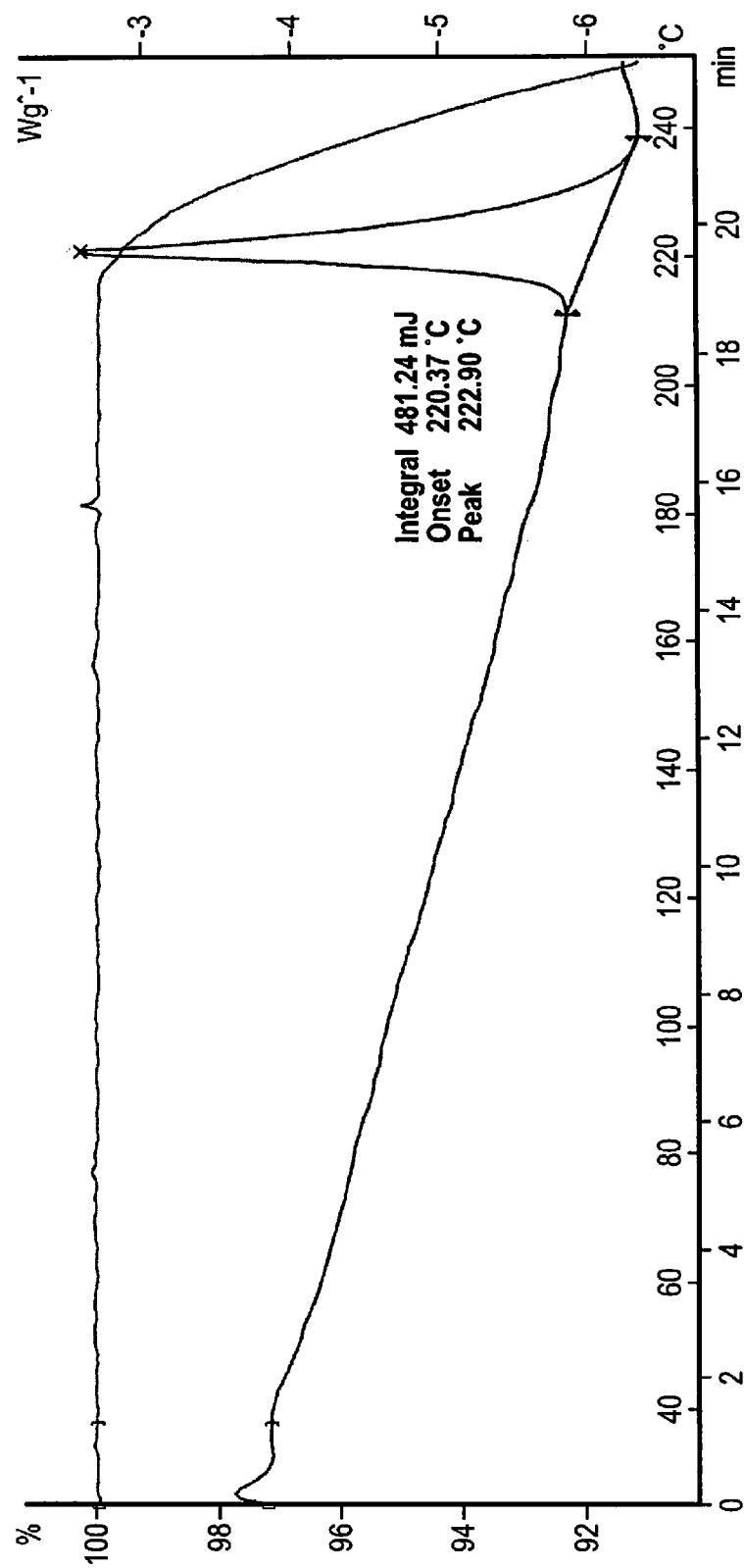
FIG. 12 shows the thermogravimetric differential thermal analysis (TG/DTA) thermogram for Compound 1 Form III, run from 30-300° C. at 10° C./min.
Figure 13:
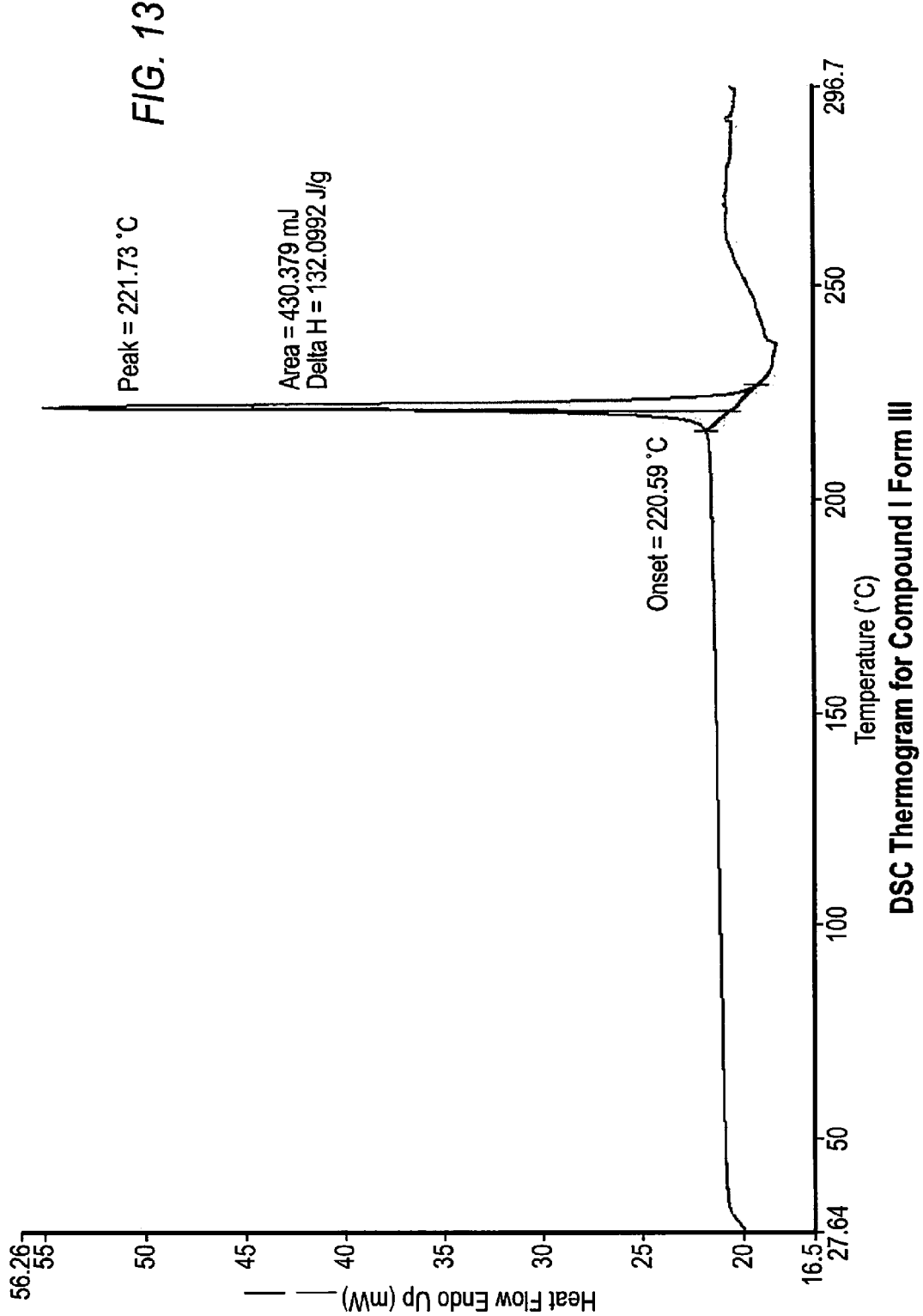
FIG. 13 shows the differential scanning calorimetry (DSC) thermogram for Compound 1 Form III, run from 30-300° C. at 10° C./min.

Other solid state properties which may be used to characterize Compound 1 Form III are shown in the FIGS. (FIGS. 12-15) and discussed in the examples below. For example, no weight loss was observed in the TG/DTA analysis of Compound 1 Form III, indicating that Compound 1 Form III is an anhydrous material (FIG. 12). The hygroscopicity and the sorption properties of Compound 1 Form III indicated very small weight gain between 0% RH and 80% RH, indicating that Compound 1 Form III is non-hygroscopic according to the European Pharmacopeia classification.

Compound 1 Form III can be prepared by agitating a mixture of Compound 1 Form I and THF at ambient temperature until Compound 1 Form I is dissolved. The mixture is then heated to a temperature of at least 40° C. and the pressure is reduced to approximately 100 torr. After approximately one-half of the volume of THF was removed by distillation, methanol was added to the flask to achieve the approximate starting volume. This distillation was repeated at least two times, and the mixture was returned to ambient temperature and pressure. The resulting solids were collected and dried.

Figure 16:
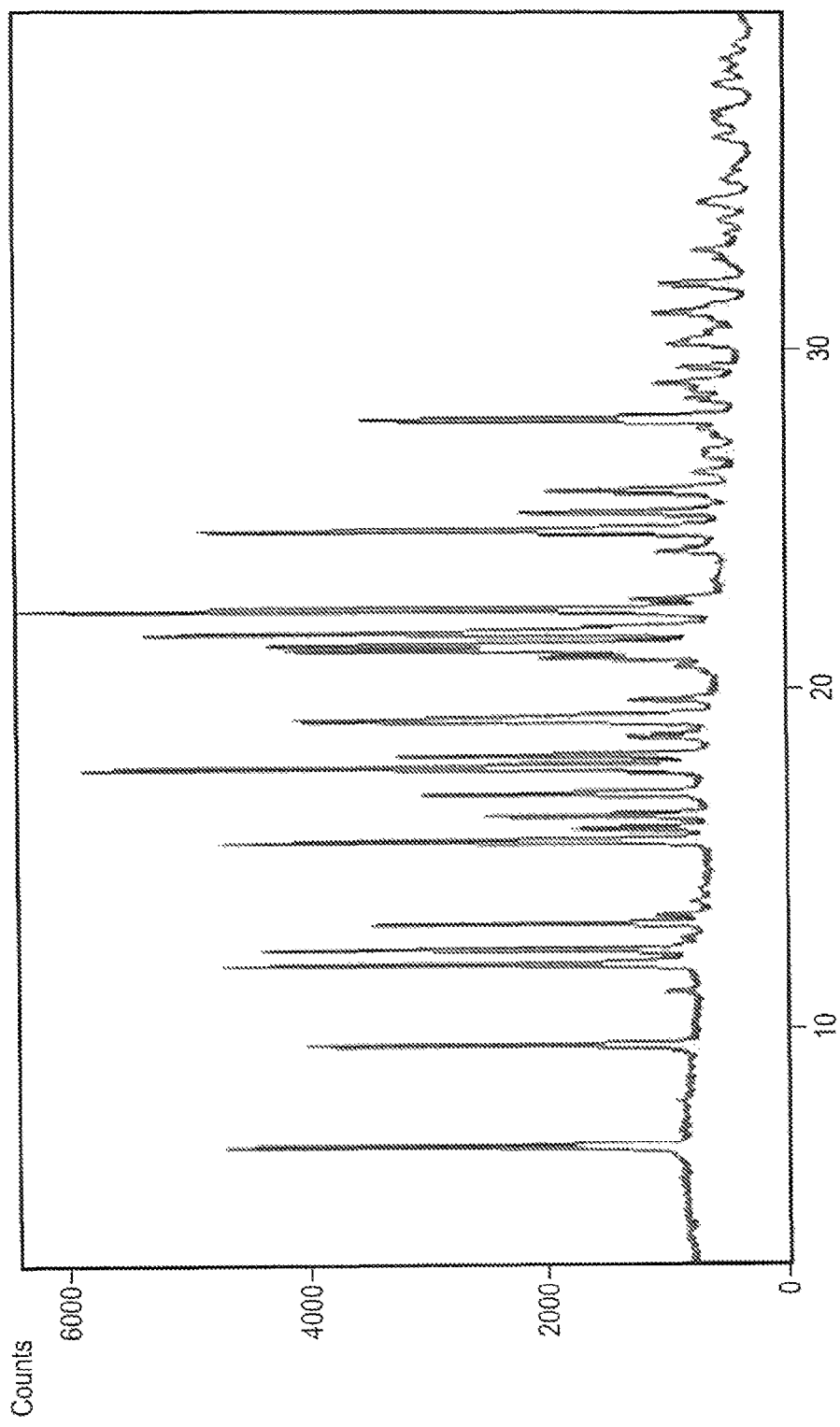
FIG. 16 shows the experimental x-ray powder diffraction (XRPD) pattern for Compound 1 Form XXVIII.

Compound 1 Form XXVIII may be characterized by at least one of the following:

(i) an x-ray powder diffraction pattern (CuKα) comprising two or more peaks as depicted in FIG. 16, wherein measurement of the crystalline form is at an ambient room temperature; and (ii) an x-ray powder diffraction (XRPD) spectrum substantially in accordance with the pattern shown in FIG. 16.

In one embodiment, Compound 1 Form XXVIII may be characterized by an x-ray powder diffraction pattern (CuKα) comprising peaks at 6.5, 9.5, 11.8, 12.3, 13.04, 15.5, 16.9, 17.7, 19.1, 21.7 and 22.3 (°2θ±0.2 °2θ). In another embodiment, Compound 1 Form XXVIII may be characterized by an x-ray powder diffraction pattern (CuKα) comprising peaks at 6.5, 9.5, 11.8, 12.3, 13.0, 17.7, 19.1, and 22.3 (°2θ±0.2 °2θ). In another embodiment, Compound 1 Form XXVIII may be characterized by an x-ray powder diffraction pattern (CuKα) comprising peaks at 9.5, 11.8, 13.0, and 22.3 (°2θ±0.2 °2θ). In a further embodiment, Compound 1 Form XXVIII may be characterized by an x-ray powder diffraction pattern (CuKα) comprising peaks at 6.5, 12.3, 17.7, 19.1 (°2θ±0.2 °2θ).

Figure 17:
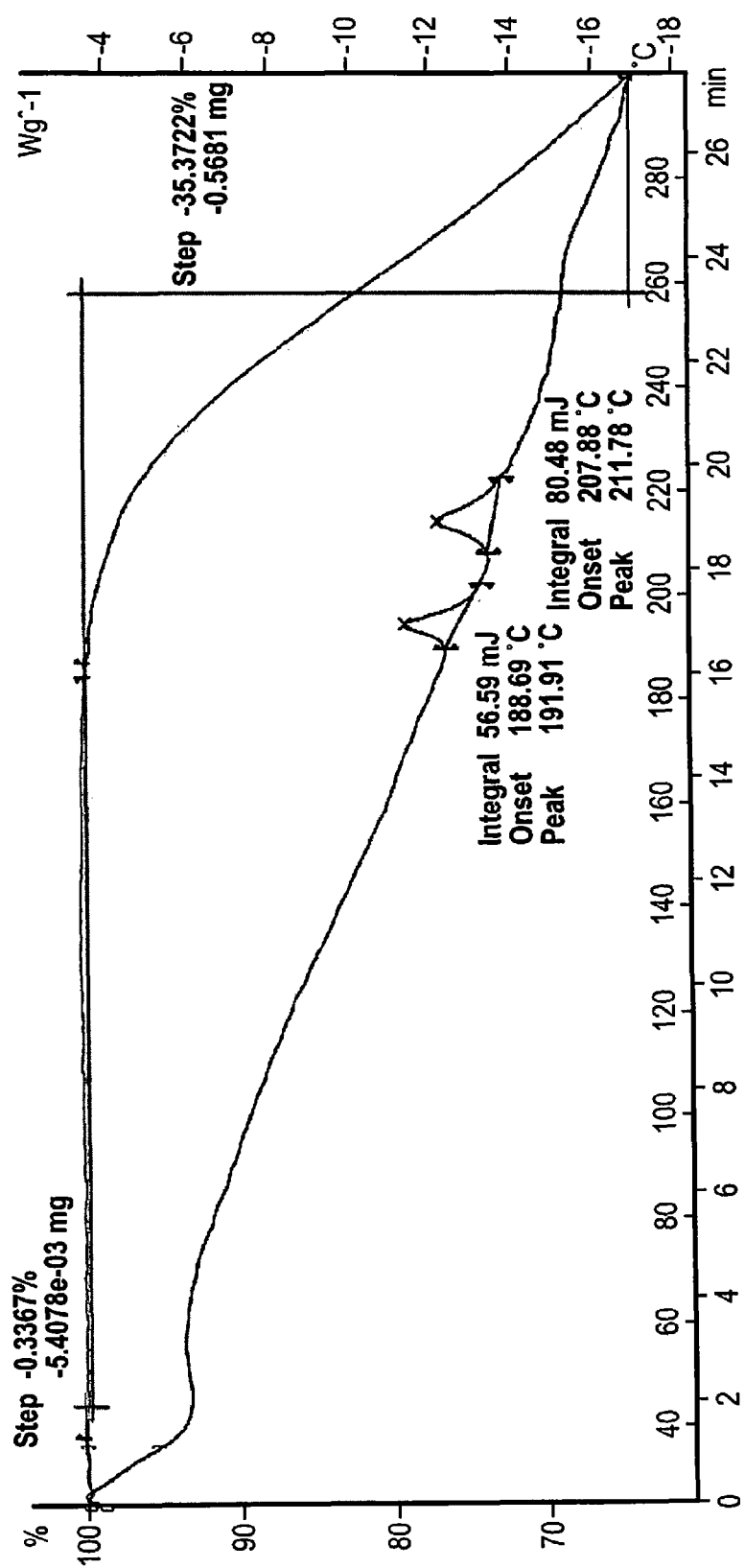
FIG. 17 shows the thermogravimetric differential thermal analysis (TG/DTA) thermogram for Compound 1 Form XXVIII, run from 30-300° C. at 10° C./min.
Figure 18:
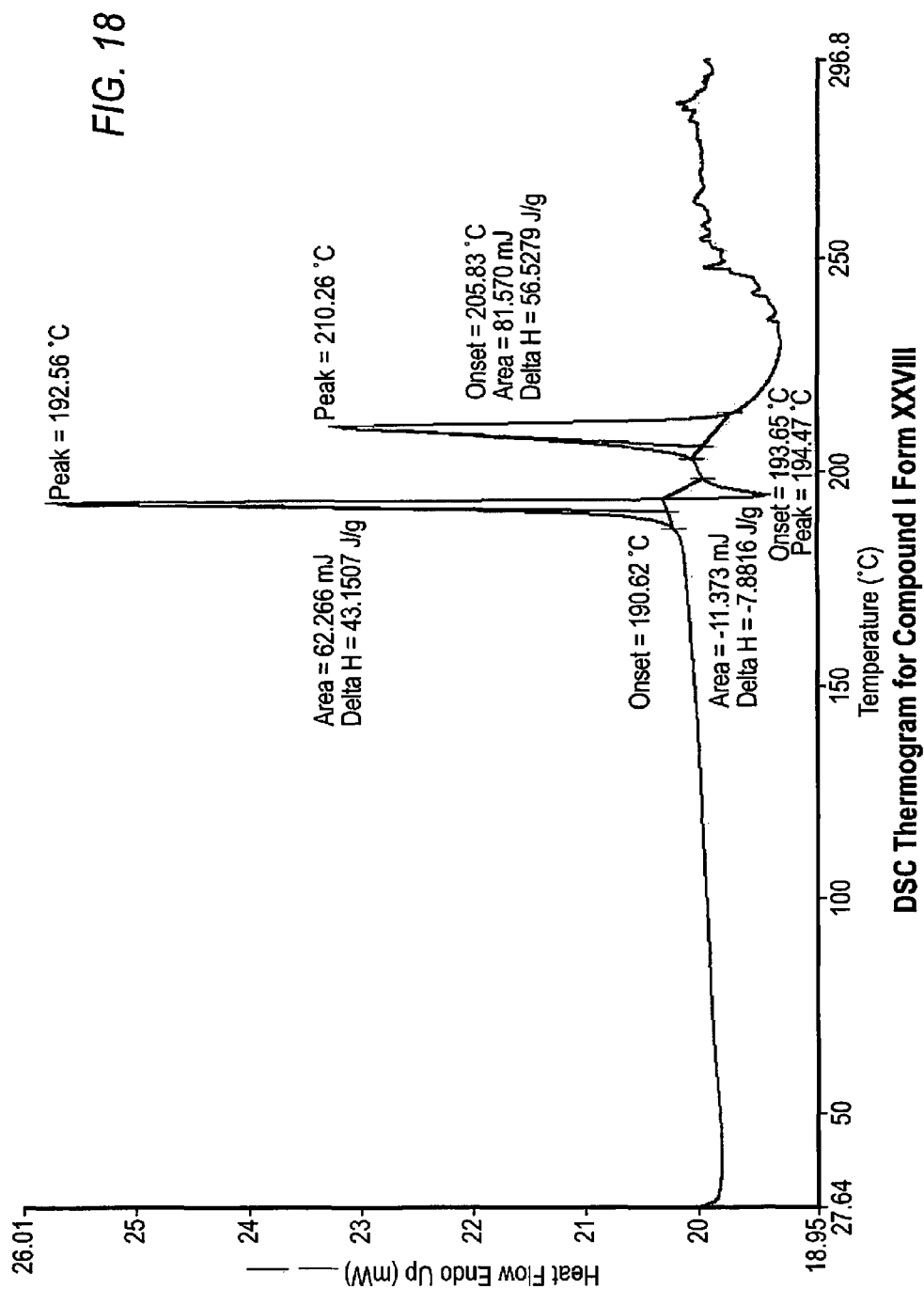
FIG. 18 shows the differential scanning calorimetry (DSC) thermogram for Compound 1 Form XXVIII, run from 30-300° C. at 10° C./min.
Figure 19:
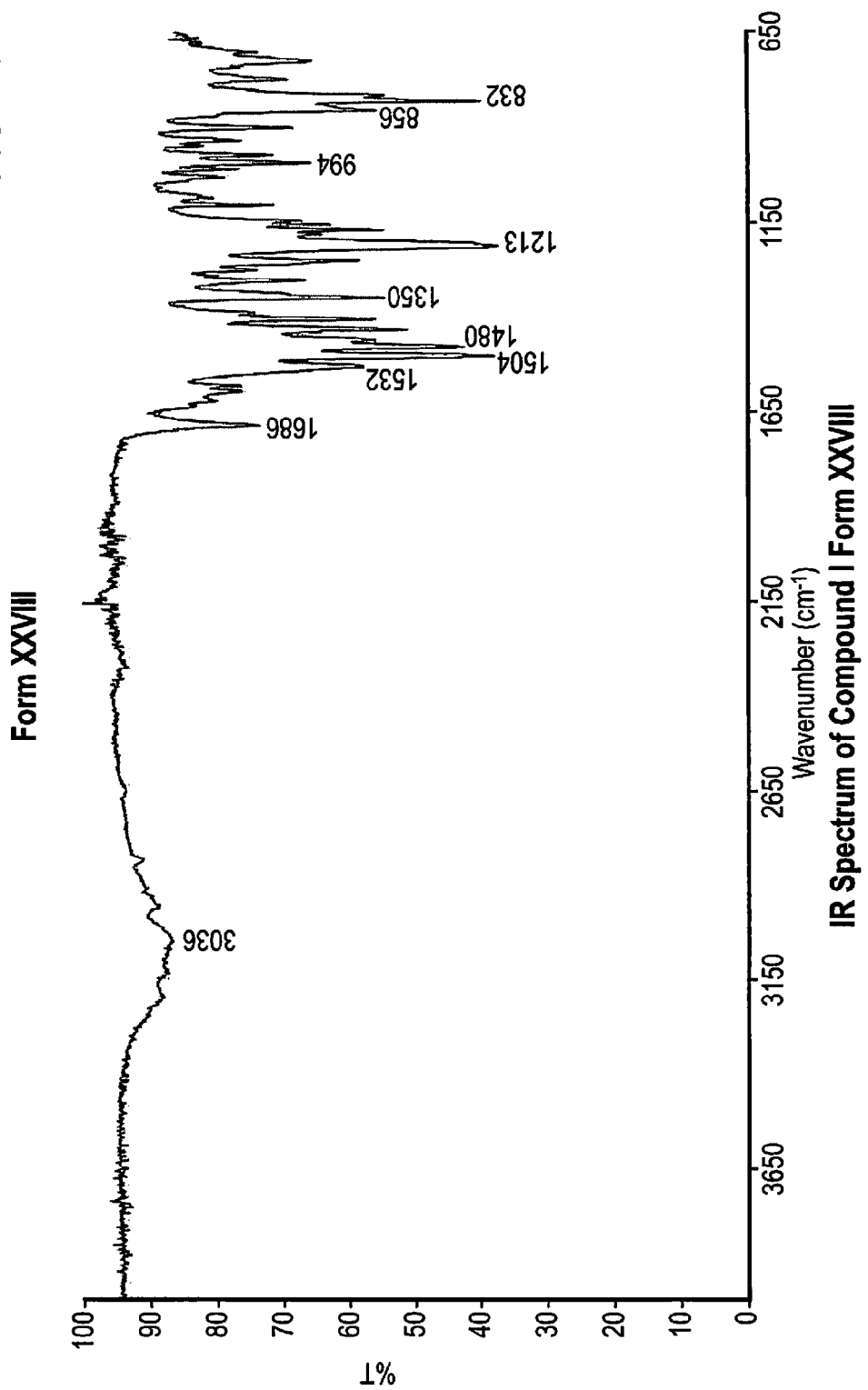
FIG. 19 shows the Fourier transfer infrared (FT-IR) spectrum for Compound 1 Form XXVIII.
Figure 20:
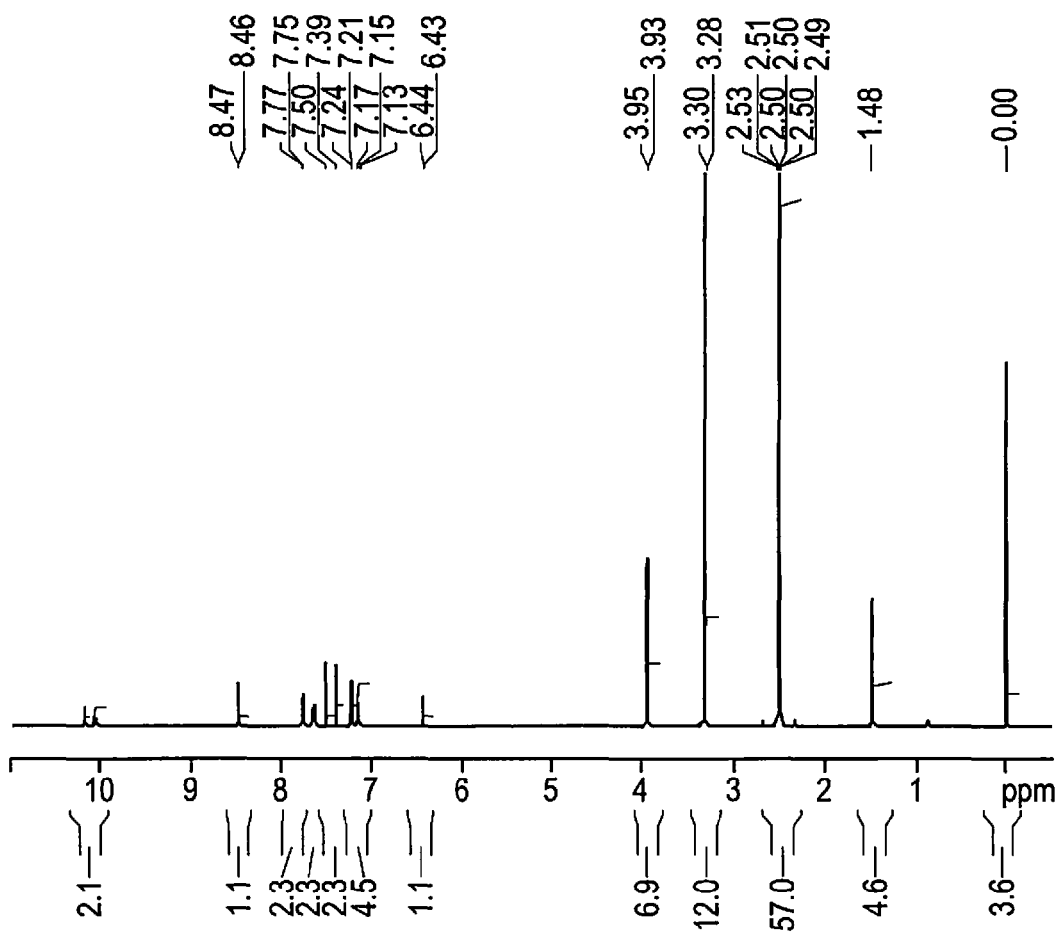
FIG. 20 shows the $^1$H nuclear magnetic resonance (NMR) spectrum for Compound 1 Form XXVIII.

Other solid state properties which may be used to characterize Compound 1 Form XXVIII are shown in the FIGS. (FIGS. 17-20) and discussed in the examples below. For example, no weight loss was observed in the TG/DTA analysis of Compound 1 Form XXVIII, indicating that Compound 1 Form XXVIII is an anhydrous material (FIG. 17). The hygroscopicity and the sorption properties indicated very small weight gain between 0% RH and 80% RH, indicating that Compound 1 Form XXVIII is non-hygroscopic.

Compound 1 Form XXVIII can be prepared by combining Compound 1 Form I and 1-butanol at low temperature (e.g., 0-10° C.) for several days. The solid Compound 1 Form XXVIII was recovered by filtration and air dried. In an alternative procedure, amorphous Compound 1 can be slurried in nitromethane for several days at room temperature. The resulting solid Compound 1 Form XXVIII are then collected, dried, and desolvated on a TG/DTA at 110° C. for 15 minutes.

Figure 21:
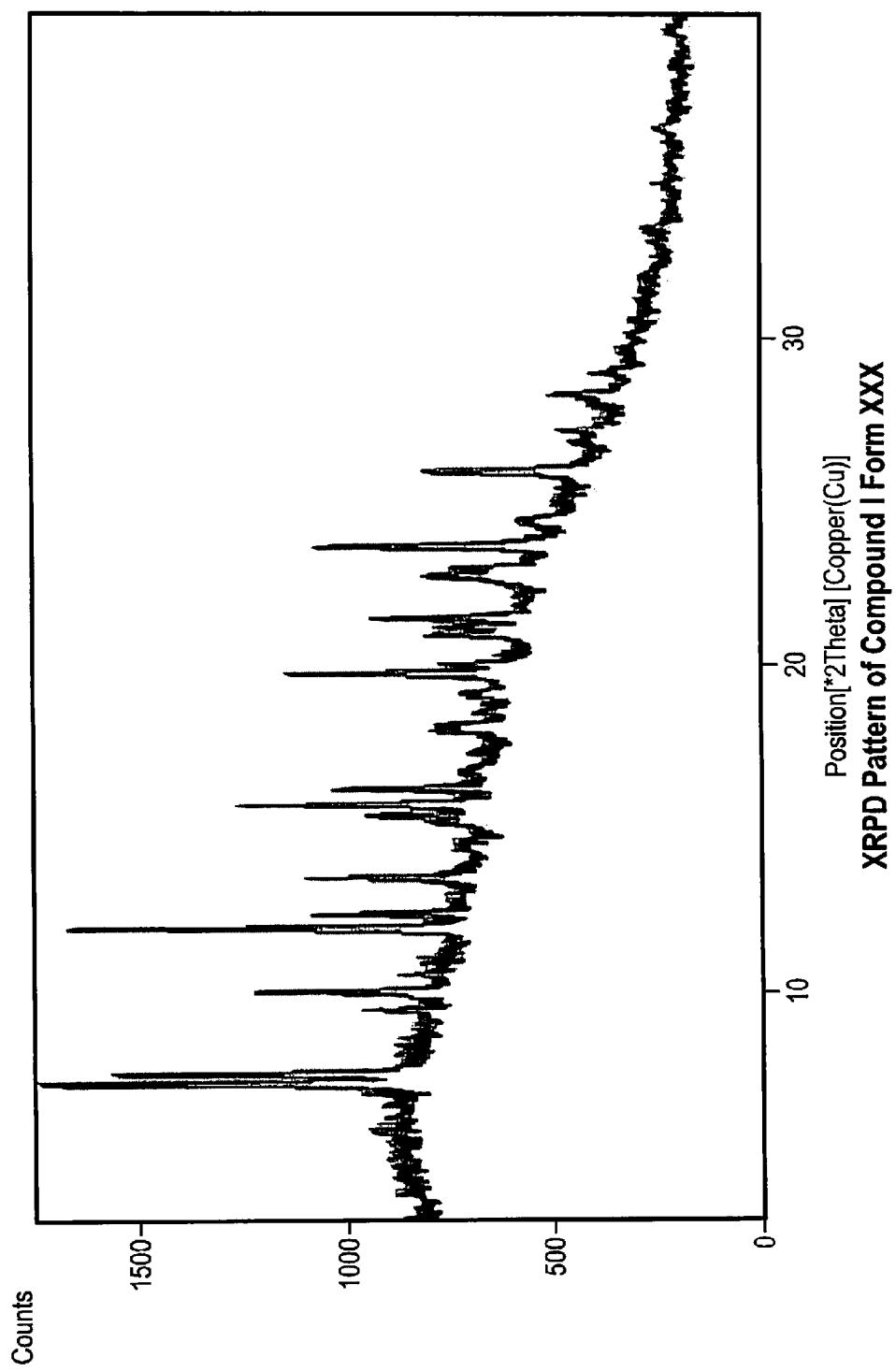
FIG. 21 shows the experimental x-ray powder diffraction (XRPD) pattern for Compound 1 Form XXX.

Compound 1 Form XXX may be characterized by at least one of the following:

(i) an x-ray powder diffraction pattern (CuKα) comprising two or more peaks as depicted in FIG. 21, wherein measurement of the crystalline form is at an ambient room temperature; and (ii) an x-ray powder diffraction (XRPD) spectrum substantially in accordance with the pattern shown in FIG. 21.

In one embodiment, Compound 1 Form XXX may be characterized by an x-ray powder diffraction pattern (CuKα) comprising peaks at 7.2, 7.5, 10.0, 12.0, 12.4, 13.5, 15.8, and 19.8 (°2θ±0.2 °2θ). In another embodiment, Compound 1 Form XXX may be characterized by an x-ray powder diffraction pattern (CuKα) comprising peaks at 7.2, 7.5, 10.0, 12.0, 12.4, 13.5, and 19.8 (°2θ±0.2 °2θ). In another embodiment, Compound 1 Form XXX may be characterized by an x-ray powder diffraction pattern (CuKα) comprising peaks at 10.0, 12.0, and 12.4 (°2θ±0.2 °2θ). In a further embodiment, Compound 1 Form XXX may be characterized by an x-ray powder diffraction pattern (CuKα) comprising peaks at 7.2, 7.5, 13.5, and 19.8 (°2θ±0.2 °2θ).

Figure 22:
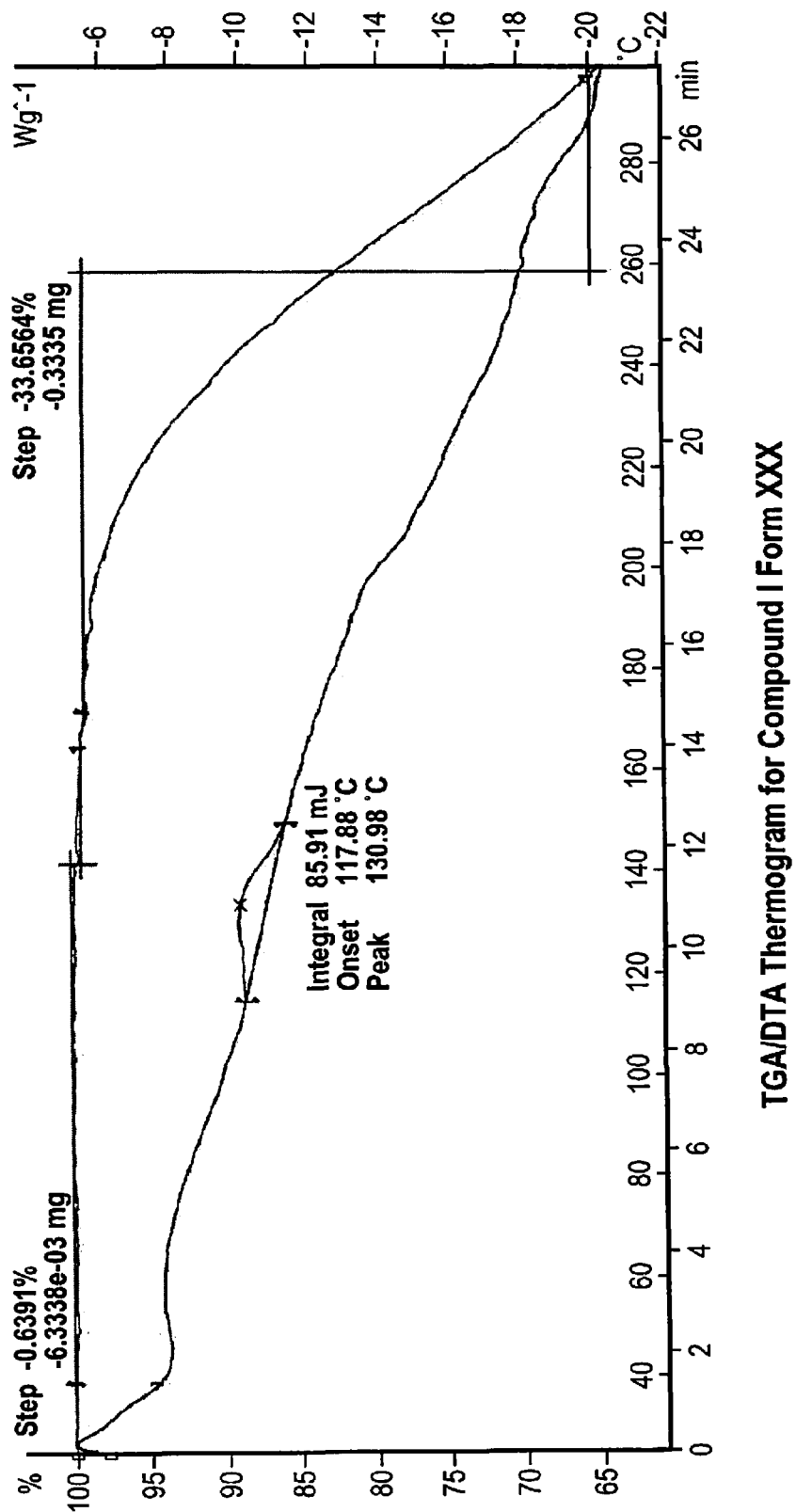
FIG. 22 shows the thermogravimetric differential thermal analysis (TG/DTA) thermogram for Compound 1 Form XXX, run from 30-300° C. at 10° C./min.
Figure 23:
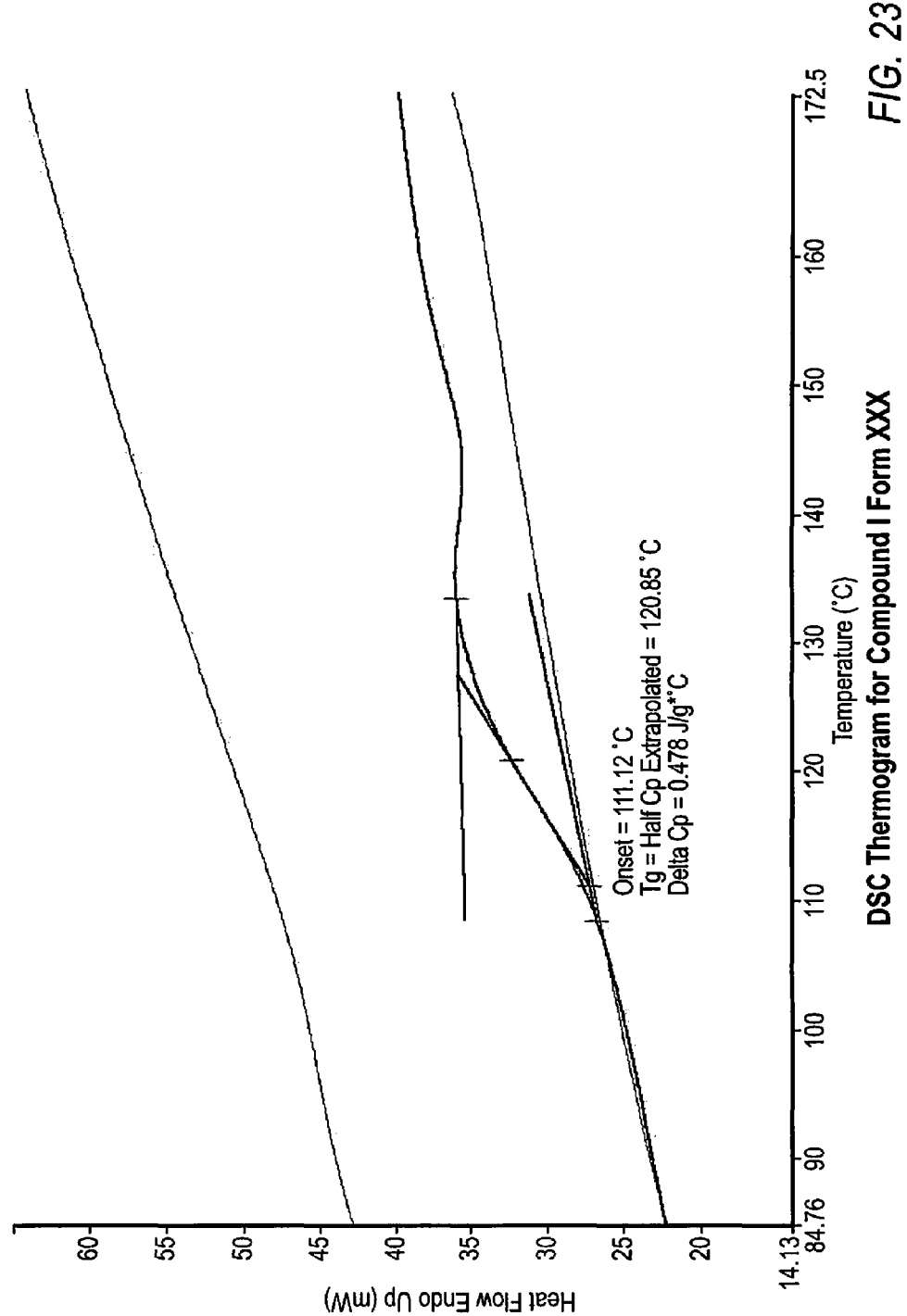
FIG. 23 shows the differential scanning calorimetry (DSC) thermogram for Compound 1 Form XXX, run from 30-300° C. at 10° C./min.
Figure 24:
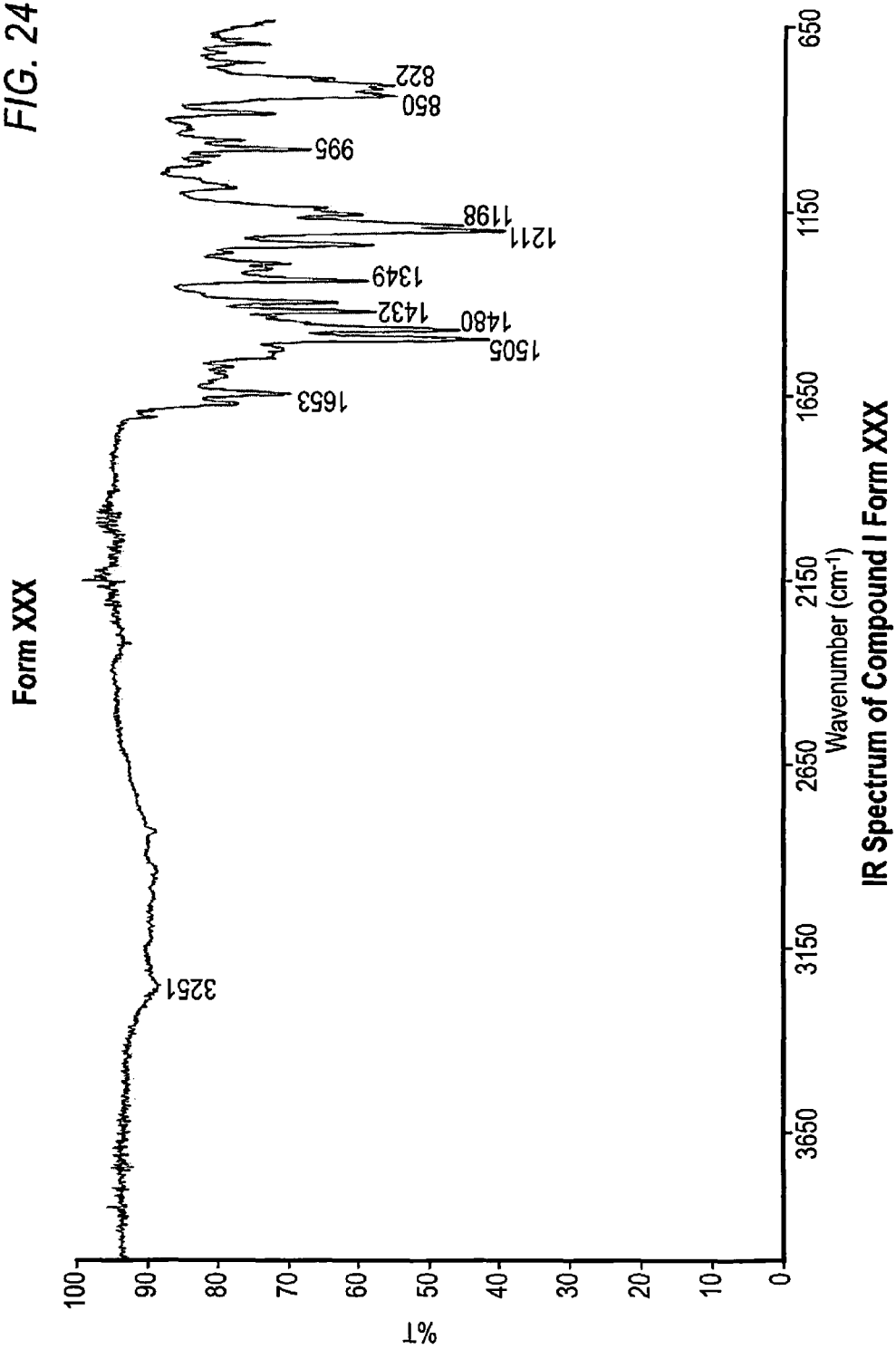
FIG. 24 shows the Fourier transfer infrared (FT-IR) spectrum for Compound 1 Form XXX.
Figure 25:
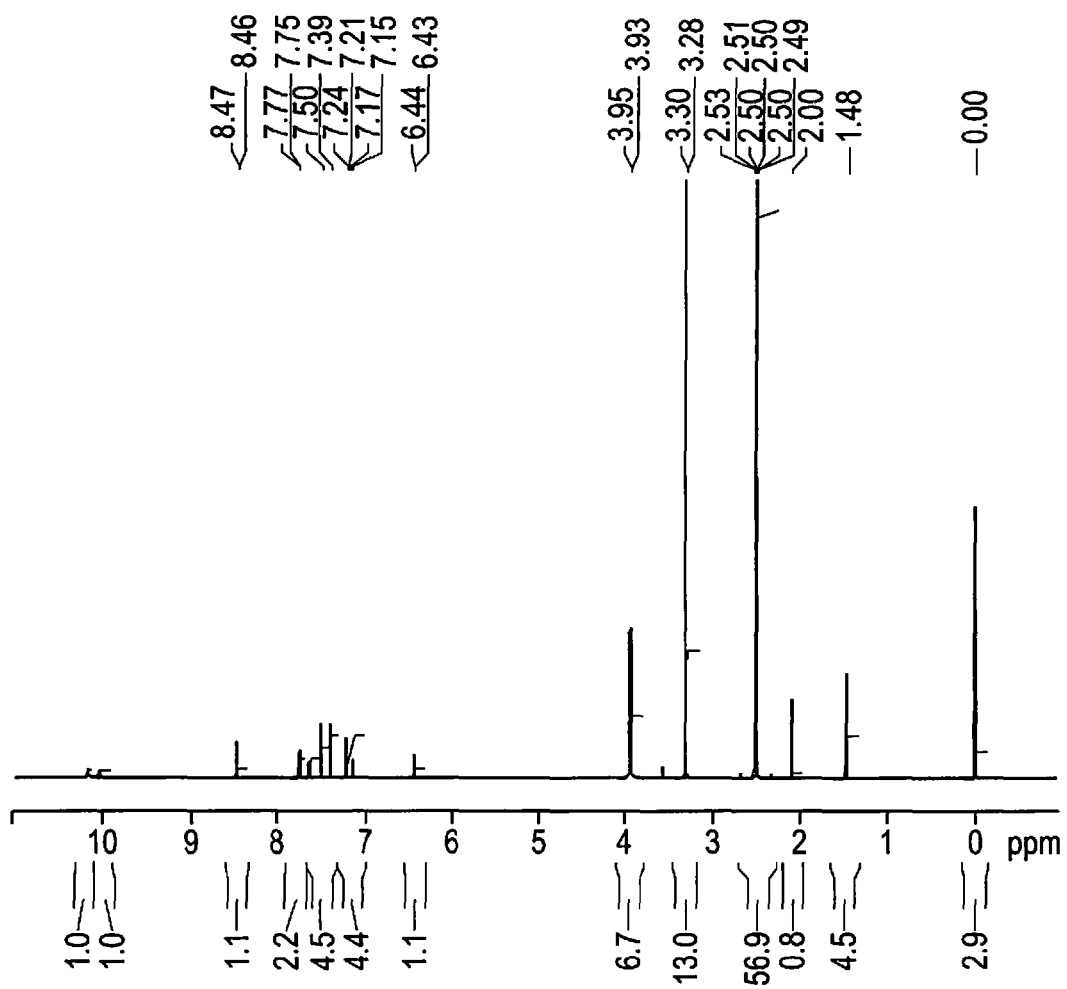
FIG. 25 shows the $^1$H nuclear magnetic resonance (NMR) spectrum for Compound 1 Form XXX.

Other solid state properties which may be used to characterize Compound 1 Form XXX are shown in the FIGS. (FIGS. 21-25) and discussed in the examples below. For example, no weight loss was observed in the TG/DTA analysis of Compound 1 Form XXX, indicating that Compound 1 Form XXX is an anhydrous material (FIG. 22). The hygroscopicity and the sorption properties of Compound 1 Form XXX indicated that Compound 1 Form XXX is hygroscopic according to the European Pharmacopeia classification.

Compound 1 Form XXX can be prepared by adding amorphous Compound 1 to a container. The container is placed unsealed inside a larger container that contains acetone. After several days, the material can be desolvated on a TG/DTA at 105° C. for 25 minutes followed by desolvation at 100° C. for 40 minutes to yield Compound 1 Form XXX.

Figure 26:
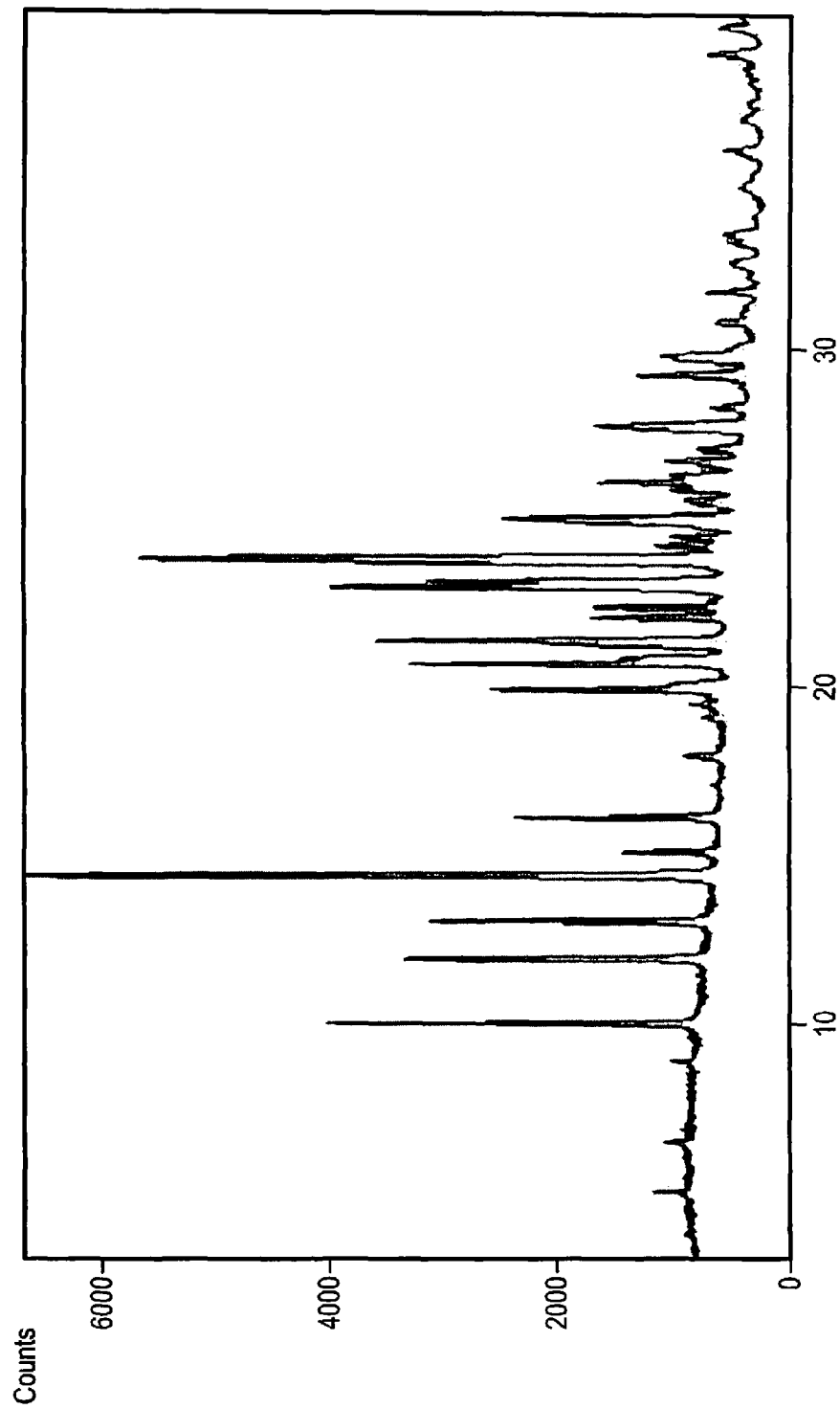
FIG. 26 shows the experimental x-ray powder diffraction (XRPD) pattern for Compound 1 Form XXXI.

Compound 1 Form XXXI may be characterized by at least one of the following:
  (i) an x-ray powder diffraction pattern (CuKα) comprising two or more peaks as depicted in FIG. 26, wherein measurement of the crystalline form is at an ambient room temperature; and
  (ii) an x-ray powder diffraction (XRPD) spectrum substantially in accordance with the pattern shown in FIG. 26.

In one embodiment, Compound 1 Form XXXI may be characterized by an x-ray powder diffraction pattern (CuKα) comprising peaks at 5.0, 10.0, 11.9, 13.0, 14.4, 16.1, 19.9, 21.4, and 23.8 (°2θ±0.2 °2θ). In another embodiment, Compound 1 Form XXXI may be characterized by an x-ray powder diffraction pattern (CuKα) comprising peaks at 5.0, 10.0, 11.9, and 13.0 (°2θ±0.2 °2θ). In a further embodiment, Compound 1 Form XXXI may be characterized by an x-ray powder diffraction pattern (CuKα) comprising peaks at 14.4, 16.1, 19.9, and 23.8 (°2θ±0.2 °2θ).

Figure 27:
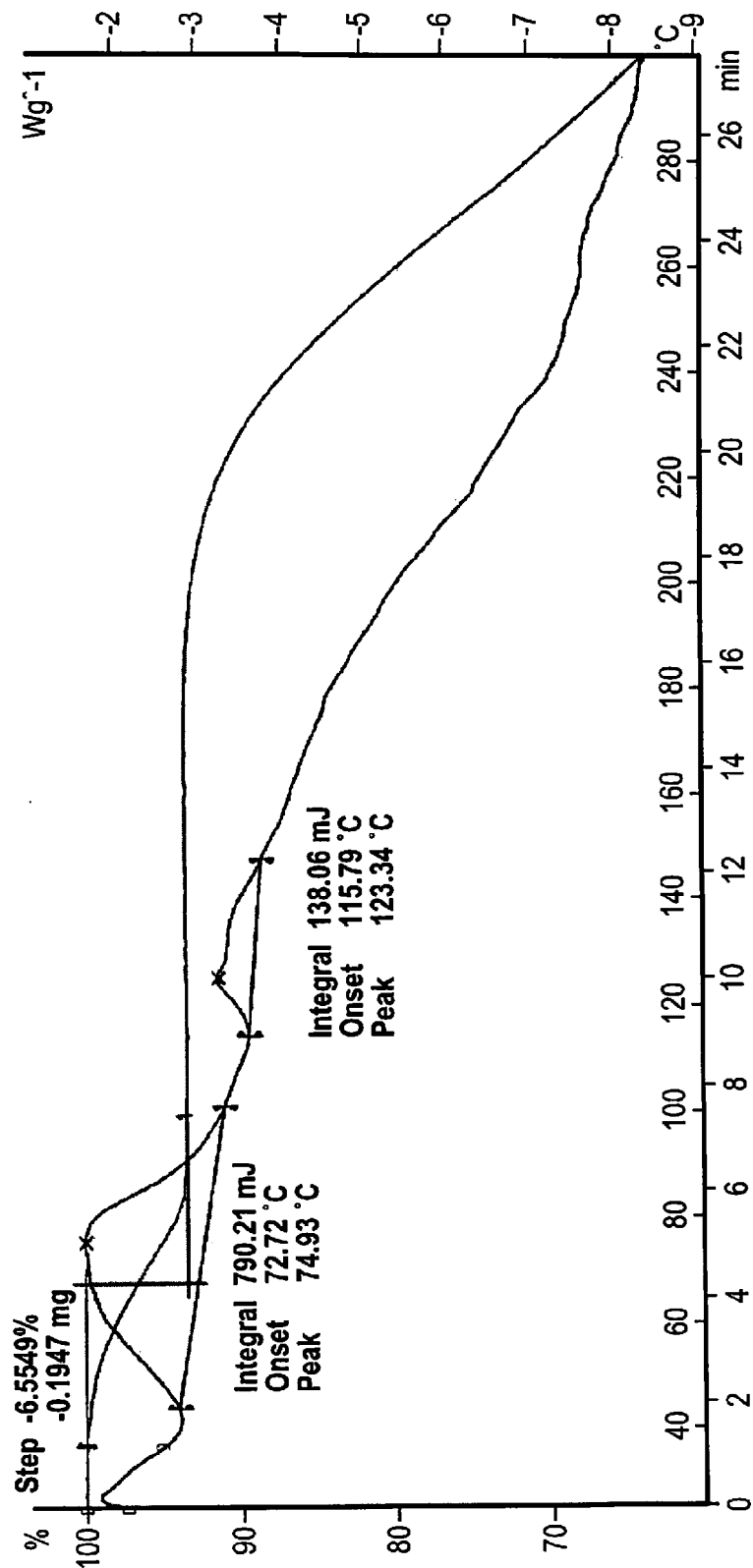
FIG. 27 shows the thermogravimetric differential thermal analysis (TG/DTA) thermogram for Compound 1 Form XXXI, run from 30-300° C. at 10° C./min
Figure 28:
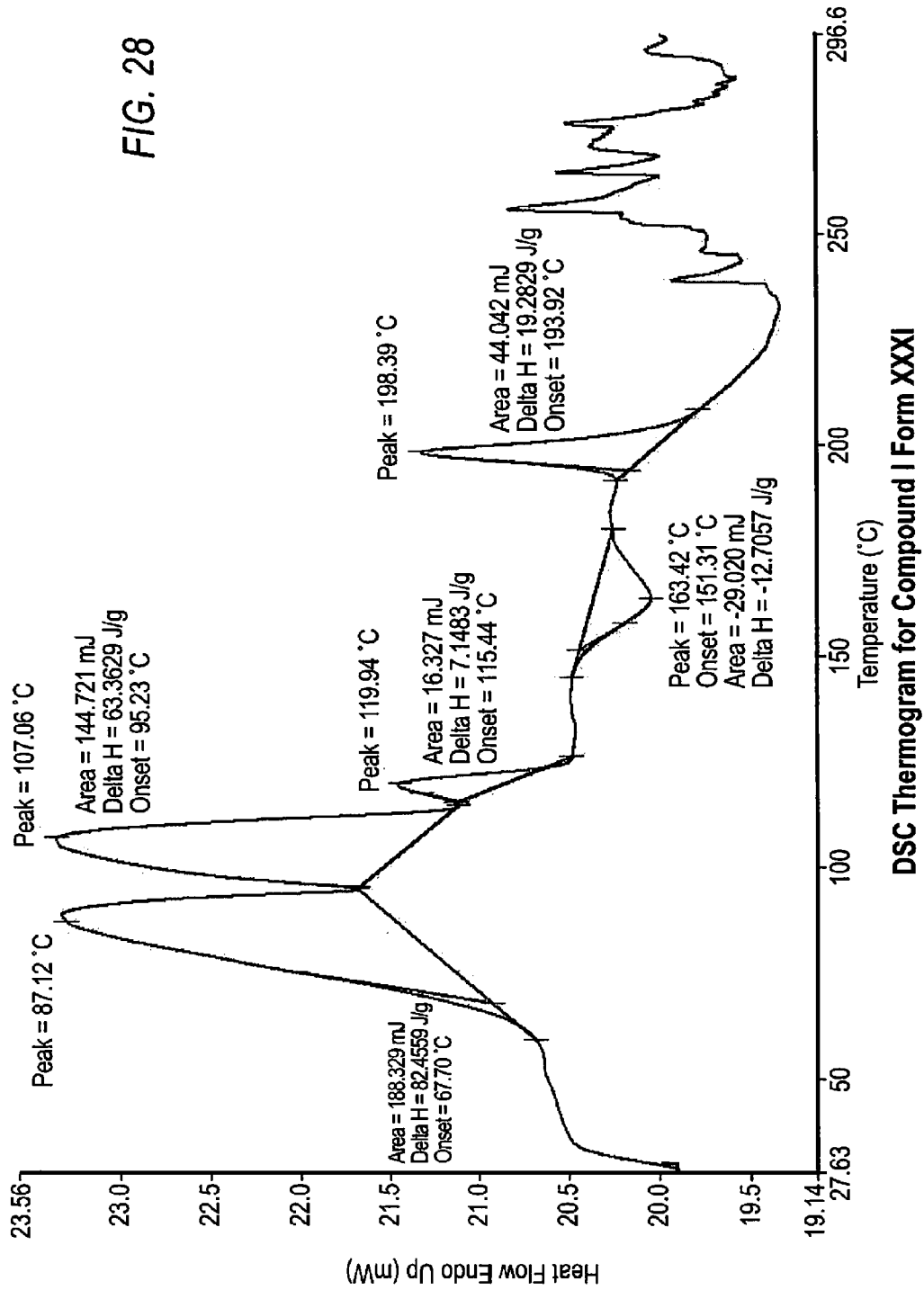
FIG. 28 shows the differential scanning calorimetry (DSC) thermogram for Compound 1 Form XXXI, run from 30-300° C. at 10° C./min.
Figure 29:
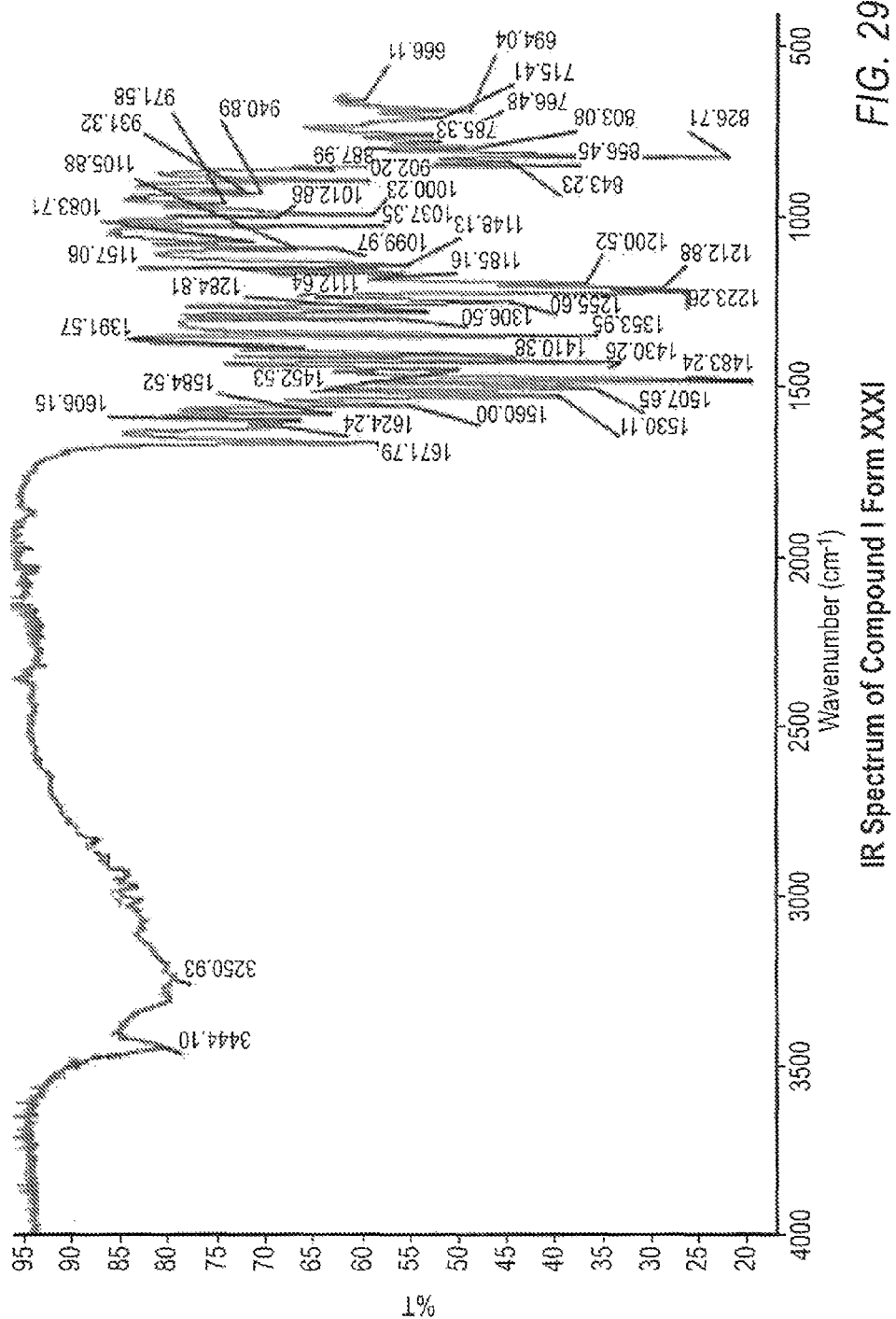
FIG. 29 shows the Fourier transfer infrared (FT-IR) spectrum for Compound XXXI, Form I.
Figure 30:
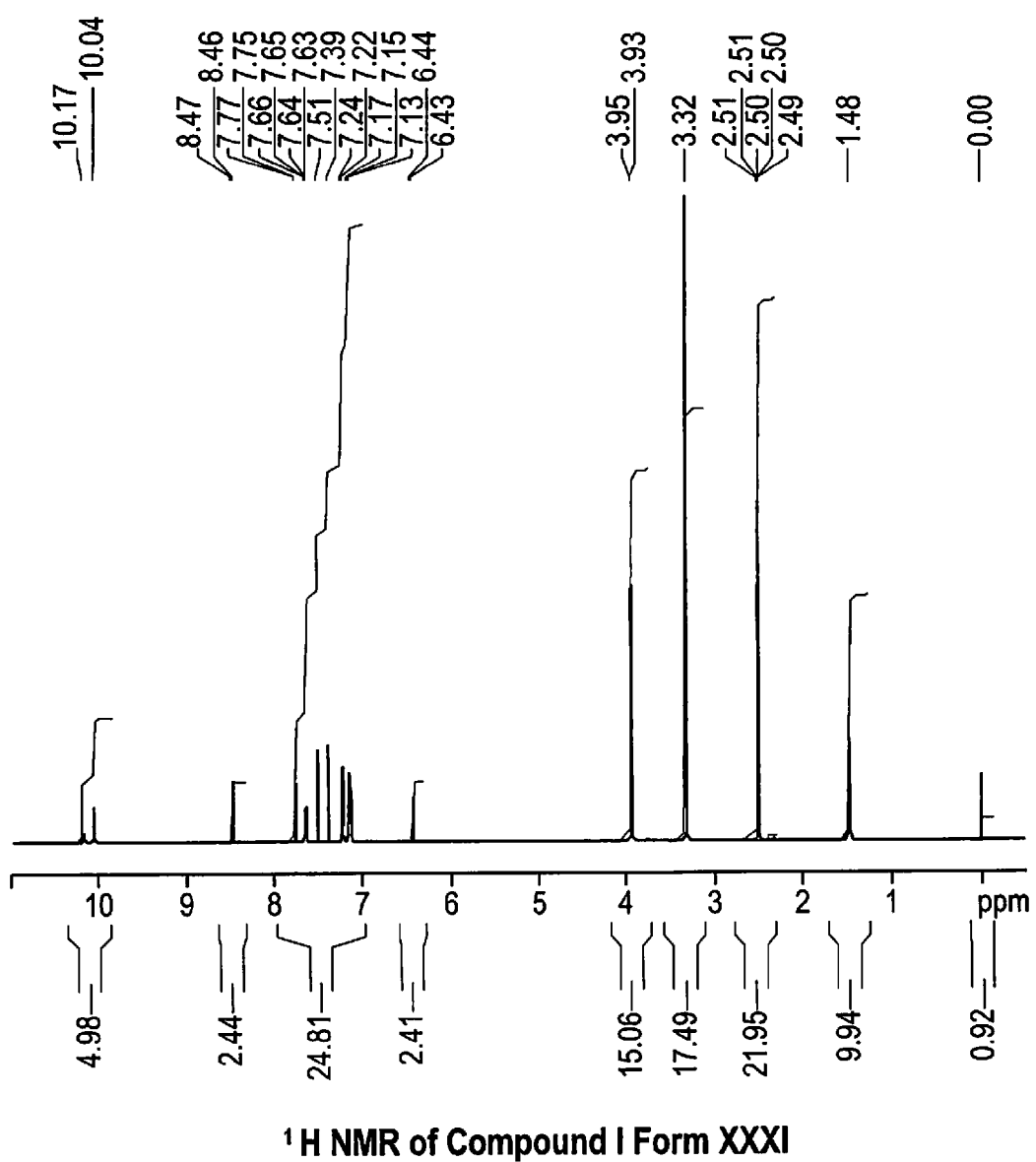
FIG. 30 shows the $^1$H nuclear magnetic resonance (NMR) spectrum for Compound 1 Form XXXI.

Other solid state properties which may be used to characterize Compound 1 Form XXXI are shown in the FIGS. (FIGS. 27-30) and discussed in the examples below. For example, 6.61 percent weight loss was observed in the TG/DTA analysis of Compound 1 Form XXXI, indicating that Compound 1 Form XXXI is a dihydrate (FIG. 27).

Compound 1 Form XXXI can be prepared by stirring a mixture of Compound 1 Form III in 2-methyltetrahydrofuran at 0-10° C. for at least two weeks to allow for saturation. Compound 1 Form I and Compound 1 Form XXXI were added, and the mixture was stirred for several days to allow for complete conversion to Compound 1 Form XXXI. The solid was recovered by vacuum filtration and dried on the filter.

In an embodiment, the disclosure relates to a solid form of Compound 1, as described herein in any of the aspects and/or embodiments, which is substantially pure Compound 1 Form I.

In another embodiment, the disclosure relates to a solid form of Compound 1, as described herein in any of the aspects and/or embodiments, which is substantially pure Compound 1 Form II.

In another embodiment, the disclosure relates to a solid form of Compound 1, as described herein in any of the aspects and/or embodiments, which is substantially pure Compound 1 Form III.

In another embodiment, the disclosure relates to a solid form of Compound 1, as described herein in any of the aspects and/or embodiments, which is substantially pure Compound 1 Form XXVIII.

In another embodiment, the disclosure relates to a solid form of Compound 1, as described herein in any of the aspects and/or embodiments, which is substantially pure Compound 1 Form XXX.

In another embodiment, the disclosure relates to a solid form of Compound 1, as described herein in any of the aspects and/or embodiments, which is substantially pure Compound 1 Form XXXI.

A further aspect of the disclosure relates to mixtures of the crystalline solid forms of Compound 1 as described herein in any of the aspects and/or embodiments.

Each of the crystalline solid forms of Compound 1 described herein has unique characteristics that can distinguish them one from another. These characteristics can be understood by comparing the physical properties of the solid state forms which are presented in the Examples below.

In another embodiment, the invention is directed to Compound 1 crystalline solid Form I, II, III, XXVIII, XXX, or XXXI with an XRPD pattern selected from the group consisting of:

| Compound 1 | | | | | |
| --- | --- | --- | --- | --- | --- |
| Form I | Form II | Form III | Form XXVIII | Form XXX | Form XXXI |
| 10.1 | 6.4 | 7.0 | 6.5 | 7.2 | 5.0 |
| 11.9 | 11.6 | 7.8 | 9.5 | 7.5 | 10.0 |
| 12.9 | 12.1 | 9.4 | 11.8 | 10.0 | 11.9 |
| 14.4 | 12.6 | 11.1 | 12.3 | 12.0 | 13.0 |
| 16.0 | 12.9 | 12.6 | 13.0 | 12.4 | 14.4 |
| 23.0 | 14.8 | 14.1 | 15.5 | 13.5 | 16.1 |
| 23.6 | 14.9 | 15.5 | 16.9 | 15.8 | 19.9 |
| 24.7 | 18.0 | 17.3 | 17.7 | 19.8 | 21.4 |
|  | 18.8 | 22.3 | 19.1 |  | 23.8 |
|  | 20.2 | 24.3 | 21.7 |  |  |
|  |  |  | 22.3 |  |  |

In another embodiment, the invention is directed to Compound 1 crystalline solid Form I, II, II, XXVIII, XXX, or XXXI with an XRPD pattern selected from the group consisting of:

| Compound 1 | | | | | |
| --- | --- | --- | --- | --- | --- |
| Form I | Form II | Form III | Form XXVIII | Form XXX | Form XXXI |
| 10.1 | 6.4 | 7.0 | 6.5 | 7.2 | 5.0 |
| 11.9 | 8.6 | 7.8 | 9.5 | 7.5 | 10.0 |
| 12.9 | 12.1 | 9.4 | 11.8 | 10.0 | 11.9 |
| 14.4 | 12.6 | 11.1 | 12.3 | 12.0 | 13.0 |
| 16.0 | 12.9 | 12.6 | 13.0 | 12.4 | 14.3 |
| 23.6 | 14.8 | 14.1 | 17.7 | 13.5 | 14.4 |
|  | 14.9 | 22.3 | 19.1 | 19.8 | 16.1 |
|  | 20.2 | 24.3 | 22.3 |  | 19.9 |
|  |  |  |  |  | 23.8 |

In another embodiment, the invention is directed to Compound 1 crystalline solid Form I, II, III, XXVIII, XXX, or XXXI with an XRPD pattern selected from the group consisting of:

| Compound 1 | | | | | |
| --- | --- | --- | --- | --- | --- |
| Form I | Form II | Form III | Form XXVIII | Form XXX | Form XXXI |
| 11.9 | 6.4 | 7.0 | 6.5 | 7.2 | 14.4 |
| 14.4 | 8.6 | 7.8 | 12.3 | 7.5 | 16.1 |
| 16.0 | 14.9 | 11.1 | 17.7 | 13.5 | 19.9 |
| 23.6 | 20.2 | 14.1 | 19.1 | 19.8 | 23.8 |

In another embodiment, the invention is directed to Compound 1 crystalline solid Form I, II, III, XXVIII, XXX, or XXXI with an XRPD pattern selected from the group consisting of:

| Compound 1 | | | | | |
|---|---|---|---|---|---|
| Form I | Form II | Form III | Form XXVIII | Form XXX | Form XXXI |
| 10.1 | 11.6 | 9.4 | 9.5 | 10.0 | 5.0 |
| 12.9 | 12.1 | 11.5 | 11.8 | 12.0 | 10.0 |
|  | 12.6 | 12.6 | 13.0 | 12.4 | 11.9 |
|  | 12.9 | 22.3 | 22.3 |  | 13.0 |
|  | 14.9 | 24.3 |  |  | 14.3 |

In another embodiment, the the invention is directed to a crystalline solid form of compound 1 having an XRPD patterns as represented by:

| Compound 1 | | | | |
|---|---|---|---|---|
| Form I | Form III | Form XXVIII | Form XXX | Form XXXI |
| FIG. 2 | FIG. 11 | FIG. 16 | FIG. 21 | FIG. 26 |

As indicated above the disclosed herein can be used to form the L-malate salt of cyclopropane-1,1-dicarboxylic acid [4-(6,7-dimethoxy-quinolone-4-yloxy)-phenyl]-amide (4-fluoro-phenyl)-amide (cabozantinib). For example, L-malic acid can be added to a solution of, cyclopropane-1,1-dicarboxylic acid [4-(6,7-dimethoxy-quinolone-4-yloxy)-phenyl]-amide (4-fluoro-phenyl)-amide free base in ethanol, maintaining a temperature of approximately 25° C. Carbon (0.5 kg) and thiol silica (0.1 kg) are then added, and the resulting mixture is heated to approximately 78° C., at which point water (6.0 kg) is added. The reaction mixture is then filtered, followed by the addition of isopropanol (38.0 kg), and is allowed to cool to approximately 25° C. The product is recovered by filtration and washed with isopropanol (20.0 kg) and dried at approximately 65° C. to afford the L-malate salt of cyclopropane-1,1-dicarboxylic acid [4-(6,7-dimethoxy-quinolone-4-yloxy)-phenyl]-amide (4-fluoro-phenyl)-amide.

Pharmaceutical Compositions and Methods of Treatment

Another aspect of this disclosure relates to a pharmaceutical composition comprising at least one crystalline solid form of Compound 1 as described herein in any of the aspects and/or embodiments, or combinations thereof, and a pharmaceutically acceptable excipient. Pharmaceutical compositions of Compound 1 have been disclosed in, for example, commonly assigned PCT Patent Publication Nos. WO 2005/030140, WO 2012/009722, and WO 2012/109510, each of which is incorporated by reference herein in its entirety.

The amount of the crystalline Compound 1 solid form or combinations thereof in the pharmaceutical composition can be a therapeutically effective amount. The crystalline solid forms of Compound 1 may individually be present in the pharmaceutical composition or as combinations. The crystalline solid forms as disclosed herein include Compound 1 Form I, Compound 1 Form II, Compound 1 Form III, Compound 1 Form XXVIII, Compound 1 Form XXX, and Compound 1 Form XXXI. Accordingly, another aspect of this disclosure relates to a solid or dispersion pharmaceutical composition comprising at least one of a therapeutically effective amount of a solid form of Compound 1, as described herein in any of the aspects and/or embodiments, or combinations thereof, and a pharmaceutically acceptable excipient.

A pharmaceutical composition such as disclosed herein may be any pharmaceutical form which contains an active crystalline Compound 1 solid form. The pharmaceutical composition may be, for example, a tablet, capsule, liquid suspension, injectable, topical, or transdermal. The pharmaceutical compositions generally contain about 1% to about 99% by weight of the active compound(s), or a solid form of the active compound(s), and 99% to 1% by weight of a suitable pharmaceutical excipient. In one example, the composition will be between about 5% and about 75% by weight of active compound, with the rest being suitable pharmaceutical excipients or other adjuvants, as discussed below.

The actual amount required for treatment of any particular subject will depend upon a variety of factors including the disease state being treated and its severity; the specific pharmaceutical composition employed; the age, body weight, general health, sex, and diet of the subject; the mode of administration; the time of administration; the route of administration; and the rate of excretion of the active compound(s), or a solid form of the active compound(s), according to this disclosure; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173, 2001, which is incorporated herein by reference. The active compound(s), or a solid form of active compound(s), according to this disclosure and pharmaceutical compositions comprising them, may be used in combination with anticancer or other agents that are generally administered to a subject being treated for cancer. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends partly upon the desired method of administration to be used. For a pharmaceutical composition of this disclosure, that is, one of the active compound(s), or a solid form of the active compound(s), of this disclosure, a carrier should be chosen so as to substantially maintain the particular form of the active compound(s), whether it would be solid or not. In other words, the carrier should not substantially alter the form of the active compound(s). Nor should the carrier be otherwise incompatible with the form of the active compound(s), such as by producing any undesirable biological effect or otherwise interacting in a deleterious manner with any other component(s) of the pharmaceutical composition.

The pharmaceutical compositions of this disclosure may be prepared by methods know in the pharmaceutical formulation art, for example, see Remington's Pharmaceutical Sciences, 18$^{th}$ Ed., (Mack Publishing Company, Easton, Pa., 1990). In solid dosage forms, Compound 1 Form I, II, III, XXVIII, or XXX, or combinations thereof, is admixed with at least one pharmaceutically acceptable excipient such as sodium citrate or dicalcium phosphate or (a) fillers or extenders, as for example, starches, lactose, sucrose, glucose, mannitol, and silicic acid, (b) binders, as for example, cellulose derivatives, starch, alginates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, I solution retarders, as for example paraffin, (f) absorption accelerators, as for example, quaternary ammonium compounds, (g) wetting agents, as for example, cetyl alcohol, and glycerol monostearate, magnesium stearate, and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of this disclosure. These include, but are not limited to, preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. If desired, a pharmaceutical composition of this disclosure may also contain minor amounts of auxiliary substances such as wetting or emulsifying agents, pH buffering agents, and antioxidants, such as, for example, citric acid, sorbitan monolaurate, triethanolamine oleate, and butylated hydroxytoluene.

In some instances, the pharmaceutical dosage form may be a solid dispersion. The term "solid dispersion" refers to a system in a solid state comprising at least two components, wherein one component is dispersed throughout the other component or components. For example, the can be an amorphous solid dispersion. The tem "amorphous solid dispersion" as used herein, refers to stable solid dispersions comprising amorphous drug substance (Compound 1) and a stabilizing polymer. By "amorphous drug substance," it is meant that the amorphous solid dispersion contains drug substance in a substantially amorphous solid state form, that is at least 80% of the drug substance in the dispersion is in an amorphous form. More preferably, at least 90% and most preferably at least 95% of the drug substance in the dispersion is in amorphous form. The term "stabilizing polymer" any polymer known to the skilled practitioner that is used to stabilize an amorphous drug substance in a solid dispersion such as are described, for instance, in Remington's Pharmaceutical Sciences, 18$^{th}$ Ed., (Mack Publishing Company, Easton, Pa., 1990).

Processes for making such solid dispersions are also available to the skilled practitioner and include, for instance, spray drying, melt extrusion, freeze drying, rotary evaporation, drum drying, or other solvent removal processes. In the spray drying process, the amorphous dispersion is formed by dispersing or dissolving the drug substance and the stabilizing polymer in a suitable solvent to form a feed solution, pumping the feed solution through an atomizer into a drying chamber, and removing the solvent to form the amorphous solid dispersion powder in the drying chamber. A drying chamber uses hot gases, such as forced air, nitrogen, nitrogen-enriched air, or argon to dry particles. The feed solution can be atomized by conventional means well known in the art, such as a two-fluid sonicating nozzle and a two-fluid non-sonicating nozzle.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the active compound(s), or a solid form of the active compound(s), with, for example, suitable non-irritating excipients or carriers such as cocoa butter, polyethyleneglycol, or a suppository wax, which are solid at ordinary temperatures but liquid at body temperature and therefore melt while in a suitable body cavity and release the active component therein.

Solid dosage forms are preferred for the pharmaceutical composition of this disclosure. Solid dosage forms for oral administration, which includes capsules, tablets, pills, powders, and granules, are particularly preferred. In such solid dosage forms, the active compound(s) mixed with at least one inert, pharmaceutically acceptable excipient (also known as a pharmaceutically acceptable carrier). Administration of the active compound(s), or a solid form of the active compound(s), in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. One preferable route of administration is oral administration, using a convenient dosage regimen that can be adjusted according to the degree of severity of the disease-state to be treated.

Thus, in one embodiment, Compound 1 Form I, II, III, XXVIII, XXX, or XXXI is administered as a pharmaceutical formulation additionally comprising a pharmaceutically acceptable carrier and excipient. In some embodiments, the Compound 1 crystalline solid form is administered as a tablet. In other embodiments, compound 1 is administered as a capsule.

In another embodiment, the invention is directed to a pharmaceutical dosage form comprising 20 mg, 40 mg, 60 mg, 80 m6, 100 mg, 120 mg, or 140 mg of Compound 1 Form I, II, III, XXVIII, XXX, or XXXI or a pharmaceutical composition comprising Compound 1 Form I, II, III, XXVIII, XXX, or XXXI and a pharmaceutically acceptable carrier. The dosage form can be administered orally with fasting once daily as a tablet or capsule. In some embodiments, the dosage form is a tablet. In other embodiments, the dosage form is a capsule.

The desired dosage of Compound 1 Form I, II, III, XXVIII, XXX, or XXXI can be achieved using a combination of tablets or capsules as needed. For example to achieve a target dose of 20 mg would require administration of one 20 mg tablet or capsule. To achieve a target dose of 100 mg would require administration of one 80 mg capsule or tablet and one 20 mg capsule or tablet. To achieve a target dose of 80 mg would require administration of one 80 mg capsule or tablet. To achieve a target dose of 60 mg would require administration of three 20 mg capsules or tablets.

For example, in one embodiment, 60 mg of Compound 1 Form I, II, III, XXVIII, XXX, or XXXI is administered once daily to a patient with cancer in need of treatment. To achieve a dose of 60 mg of compound 1, a patient is administered three 20 mg tablets. The three 20 mg tablets can be taken at the same time or sequentially. In a further embodiment, compound 1 is orally administered with fasting (that is, without eating) for approximately two hours before and 1 hour after administration. Compound 1 as one of the crystalline solid forms disclosed herein is preferably administered with a glass of water (approximately 8 ounces/ 240 mL).

In another embodiment, 40 mg of Compound 1 Form I, II, III, XXVIII, XXX, or XXXI is administered once daily to a patient with cancer in need of treatment. To achieve a dose of 40 mg of compound 1, a patient is administered two 20 mg tablets. The two 20 mg tablets can be taken at the same time or sequentially. In a further embodiment, compound 1 is orally administered with fasting (that is, without eating) for approximately two hours before and 1 hour after administration. Compound 1 as one of the crystalline solid forms disclosed herein is preferably administered with a glass of water (approximately 8 ounces/240 mL).

In one embodiment, 20 mg of Compound 1 Form I, II, III, XXVIII, XXX, or XXXI is administered once daily to a patient with cancer in need of treatment. To achieve a dose of 20 mg of compound 1, a patient is administered one 20 mg tablet. In a further embodiment, Compound 1 Form I, II, III, XXVIII, XXX, or XXXI is orally administered with fasting (that is, without eating) for approximately two hours before and 1 hour after administration. Compound 1 Form I, II, III, XXVIII, XXX, or XXXI is preferably administered with a glass of water (approximately 8 ounces/240 mL).

In another embodiment, the once-daily tablet or capsule formulation comprises:

| Ingredient | (% w/w) |
| --- | --- |
| Compound 1 Form I, II, III, XXVIII, XXX, or XXXI | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |
| Croscarmellose Sodium | 3.00 |
| Magnesium Stearate | 0.75 |
| Total | 100.00 |

In another embodiment, the once-daily tablet or capsule formulation comprises:

| Ingredient | (% w/w) |
| --- | --- |
| Compound 1 Form I, II, III, XXVIII, XXX, or XXXI | 25.0-33.3 |
| Microcrystalline Cellulose | q.s |
| Hydroxypropyl Cellulose | 3 |
| Poloxamer | 0-3 |
| Croscarmellose Sodium | 6.0 |
| Colloidal Silicon Dioxide | 0.5 |
| Magnesium Stearate | 0.5-1.0 |
| Total | 100 |

In another embodiment, the once-daily tablet or capsule formulation comprises:

| Ingredient | Theoretical Quantity (mg/unit dose) |
| --- | --- |
| Compound 1 Form I, II, III, XXVIII, XXX, or XXXI | 100.0 |
| Microcrystalline Cellulose PH-102 | 155.4 |
| Lactose Anhydrous 60M | 77.7 |
| Hydroxypropyl Cellulose, EXF | 12.0 |
| Croscarmellose Sodium | 24 |
| Colloidal Silicon Dioxide | 1.2 |
| Magnesium Stearate (Non-Bovine) | 3.0 |
| Opadry Yellow | 16.0 |
| Total | 416 |

In another embodiment, the once-daily tablet or capsule formulation comprises:

| Ingredient | Function | % w/w |
| --- | --- | --- |
| Compound 1 Form I, II, III, XXVIII, XXX, or XXXI | Active Ingredient | 31.7 |
| Microcrystalline Cellulose (Avicel PH-102) | Filler | 38.9 |
| Lactose Anhydrous (60M) | Filler | 19.4 |
| Hydroxypropyl Cellulose (EXF) | Binder | 3.0 |
| Croscarmellose Sodium (Ac-Di-Sol) | Disenegrant | 6.0 |
| Colloidal Silicon Dioxide, | Glidant | 0.3 |
| Magnesium Stearate | Lubricant | 0.75 |
| Opadry Yellow Film Coating which includes: HPMC 2910/Hypromellose 6 cp Titanium dioxide Triacetin Iron Oxide Yellow | Film Coating | 4.00 |

Any of the tablet or capsule formulations provided above can be adjusted according to the dose of the crystalline solid form of compound 1 desired. Thus, the amount of each of the formulation ingredients can be proportionally adjusted to provide a table formulation containing various amounts of Compound 1 Form I, II, III, XXVIII, XXX, or XXXI as provided in the previous paragraphs. In another embodiment, the formulations can contain 20, 40, 60, or 80 mg of Compound 1 Form I, II, III, XXVIII, XXX, or XXXI.

Another aspect of this disclosure relates to a method of treating cancer comprising administering to a subject in need thereof at least one of solid form of Compound 1 as described herein in any of the aspects and/or embodiments, or combinations thereof. Methods of treatment comprising administering Compound 1 have been disclosed in, for example, commonly assigned PCT Patent Publication Nos. WO 2005/030140, WO 2011, 017639, WO 2012/044572, WO 2012/044577, WO 2012/151326, WO 2013/043840, WO 2013/070890, WO 2013/070903, and WO2013/066296, and US Patent Application Publication Nos. US 2012/ 0070368 and US 2012/0252840, each of which is incorporated by reference herein in its entirety. The amount of the Compound 1 solid form or combinations thereof administered can be a therapeutically effective amount.

Another aspect of this disclosure relates to a method of treating diseases or disorders associated with uncontrolled, abnormal, and/or unwanted cellular activities associated with RTK overexpression, particularly cMET of RET overexpression, comprising administering to a subject in need of such treatment a therapeutically effective amount of at least one solid form of Compound 1 as described herein in any of the aspects and/or embodiments, or combinations thereof, such as discussed above.

Another aspect of this disclosure relates to a use of solid Compound 1 according to any of the above embodiments for the manufacture of a medicament for the treatment of a disease or disorder discussed above. When dissolved, a solid or amorphous form according to this disclosure loses its solid state structure, and is therefore referred to as a solution of, for example, Compound 1. At least one solid form disclosed herein may be used to prepare at least one liquid formulation in which at least one solid form according to the disclosure is dissolved and/or suspended.

In another aspect, the invention is directed to a method of treating cancer, comprising: administering a pharmaceutical dosage form comprising Compound 1 Form I, II, III, XXVIII, XXX, or XXXI or a pharmaceutical composition comprising Compound 1 Form I, II, III, XXVIII, XXX, or XXXI and a pharmaceutically acceptable carrier.

In one embodiment of this aspect, the invention is directed to a method of treating cancer, comprising administering to a patient in need of such treatment a pharmaceutical dosage form comprising 140 mg, 120 mg, 100 mg, 80 mg, 60 mg, 40 mg, or 20 mg of Compound 1 Form I, II, III, XXVIII, XXX, or XXXI or a pharmaceutical composition comprising Compound 1 Form I, II, III, XXVIII, XXX, or XXXI and a pharmaceutically acceptable carrier. In some embodiments, the dosage form is administered orally with fasting orally once daily as a tablet or capsule. In some embodiments, Compound 1 Form I, II, III, XXVIII, XXX, or XXXI or a pharmaceutical composition comprising Compound 1 Form I, II, III, XXVIII, XXX, or XXXI is administered as a tablet. In other embodiments, Compound 1 Form I, II, III, XXVIII, XXX, or XXXI or a pharmaceutical composition comprising Compound 1 Form I, II, III, XXVIII, XXX, or XXXI is administered as a capsule.

Any of the tablet or capsule formulations provided above can be adjusted according to the dose of compound 1 desired. Thus, the amount of each of the formulation ingredients can be proportionally adjusted to provide a table formulation containing various amounts of compound 1 as provided in the previous paragraphs. In another embodiment, the formulations can contain 20, 40, 60, or 80 mg of Compound 1 Form I, II, III, XXVIII, XXX, or XXXI.

In this method, the desired dosage of Compound 1 crystalline solid form can be achieved using a combination of tablets or capsules as needed. For example to achieve a target dose of 20 mg would require administration of one 20 mg tablet or capsule. To achieve a target dose of 100 mg would require administration of one 80 mg tablet or capsule and one 20 mg tablet or capsule. To achieve a target dose of 80 mg would require administration of one 80 mg tablet or capsule. To achieve a target dose of 60 mg would require administration of three 20 mg tablets or capsules.

In another embodiment of this method, 60 mg of compound 1 is administered once daily to a patient with cancer in need of treatment. To achieve a dose of 60 mg of compound 1, a patient is administered three 20 mg tablets. The three 20 mg tablets can be taken at the same time or sequentially. In a further embodiment, compound 1 is orally administered with fasting (that is, without eating) for approximately two hours before and 1 hour after administration. Compound 1 is preferably administered with a glass of water (approximately 8 ounces/240 mL).

In another embodiment of this method, 40 mg of compound 1 is administered once daily to a patient with cancer in need of treatment. To achieve a dose of 40 mg of compound 1, a patient is administered two 20 mg tablets. The two 20 mg tablets can be taken at the same time or sequentially. In a further embodiment, compound 1 as one of the crystalline solid forms disclosed herein (that is, Compound 1 Forms I, III, XXVIII, XXX, or XXXI) is orally administered with fasting (that is, without eating) for approximately two hours before and 1 hour after administration. Compound 1 is preferably administered with a glass of water (approximately 8 ounces/240 mL).

In another embodiment of this method, 20 mg of compound 1 is administered once daily to a patient with cancer in need of treatment. To achieve a dose of 20 mg of compound 1, a patient is administered one 20 mg tablet. In a further embodiment, compound 1 is orally administered with fasting (that is, without eating) for approximately two hours before and 1 hour after administration. Compound 1 is preferably administered with a glass of water (approximately 8 ounces/240 mL).

In another embodiment, the method comprises administering Compound 1 Form I, II, III, XXVIII, XXX, or XXXI orally once daily as a tablet or capsule as provided in the following table.

| Ingredient | (% w/w) |
| --- | --- |
| Compound 1 Form I, II, III, XXVIII, XXX, or XXXI | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |
| Croscarmellose Sodium | 3.00 |
| Magnesium Stearate | 0.75 |
| Total | 100.00 |

In some embodiments, the pharmaceutical dosage form is administered as a tablet. In other embodiments, the pharmaceutical dosage form is administered as a capsule.

In another embodiment, the method comprises administering compound 1 orally as one of the crystalline solid forms disclosed herein (that is, Compound 1 Forms I, II, III, XXVIII, XXX, or XXXI) orally once daily as a tablet or capsule as provided in the following table.

| Ingredient | (% w/w) |
| --- | --- |
| Compound 1 Form I, II, III, XXVIII, XXX, or XXXI | 25.0-33.3 |
| Microcrystalline Cellulose | q.s |
| Hydroxypropyl Cellulose | 3 |
| Poloxamer | 0-3 |
| Croscarmellose Sodium | 6.0 |
| Colloidal Silicon Dioxide | 0.5 |
| Magnesium Stearate | 0.5-1.0 |
| Total | 100 |

In some embodiments, the pharmaceutical dosage form is administered as a tablet. In other embodiments, the pharmaceutical dosage form is administered as a capsule.

In another embodiment, the method comprises administering compound 1 orally as one of the crystalline solid forms disclosed herein (that is, Compound 1 Forms I, II, III, XXVIII, XXX, or XXXI) orally once daily as a tablet or capsule as provided in the following table.

| Ingredient | Theoretical Quantity (mg/unit dose) |
|---|---|
| Compound 1 Form I, II, III, XXVIII, XXX, or XXXI | 100.0 |
| Microcrystalline Cellulose PH-102 | 155.4 |
| Lactose Anhydrous 60M | 77.7 |
| Hydroxypropyl Cellulose, EXF | 12.0 |
| Croscarmellose Sodium | 24 |
| Colloidal Silicon Dioxide | 1.2 |
| Magnesium Stearate (Non-Bovine) | 3.0 |
| Opadry Yellow | 16.0 |
| Total | 416 |

In some embodiments, the pharmaceutical dosage form is administered as a tablet. In other embodiments, the pharmaceutical dosage form is administered as a capsule.

In another embodiment, the method comprises administering Compound 1 Form I, II, III, XXXVIII, XXX, or XXXI orally once daily as a tablet or capsule as provided in the following table.

| Ingredient | Function | % w/w |
|---|---|---|
| Compound 1 Form I, II, III, XXVIII, XXX, or XXXI | Active Ingredient | 31.7 |
| Microcrystalline Cellulose (Avicel PH-102) | Filler | 38.9 |
| Lactose Anhydrous (60M) | Filler | 19.4 |
| Hydroxypropyl Cellulose (EXF) | Binder | 3.0 |
| Croscarmellose Sodium (Ac-Di-Sol) | Disenegrant | 6.0 |
| Colloidal Silicon Dioxide, | Glidant | 0.3 |
| Magnesium Stearate | Lubricant | 0.75 |
| Opadry Yellow Film Coating which includes: HPMC 2910/Hypromellose 6 cp Titanium dioxide Triacetin Iron Oxide Yellow | Film Coating | 4.00 |

In some embodiments, the pharmaceutical dosage form is administered as a tablet. In other embodiments, the pharmaceutical dosage form is administered as a capsule.

In some embodiments, the cancer to be treated is thyroid cancer, liver cancer, gastrointestinal cancer, pancreatic cancer, bone cancer, hematologic cancer, skin cancer, kidney cancer, breast cancer, colon cancer, fallopian tube cancer, ovarian cancer, brain cancer, lung cancer or prostate cancer.

In one embodiment, the cancer is thyroid cancer.

More particularly, the thyroid cancer is medullary thyroid cancer.

In one embodiment, the cancer in liver cancer.

More particularly, the liver cancer is hepatocellular carcinoma, cholangiocarcinoma, hepatoblastoma, angiosarcoma, hepatocellular adenoma, or hemagioma.

In one embodiment, the cancer is gastrointestinal cancer.

More particularly, the gastrointestinal cancer is cancer of the esophagous which is squamous cell carcinoma, adenocarcinoma, or leiomyosarcoma; cancer of the stomach which is carcinoma, or lymphoma; cancer of the pancreas, which is ductal adenocarcinoma, insulinoma, gucagonoma, gastrinoma, carcinoid tumors, or vipoma; cancer of the small bowel, which is adenocarcinoma, lymphoma, carcinoid tumors, Karposi's sarcoma, leiomyoma, hemagioma, lipoma; or cancer of the large bowel, which is adenocarcinoma, tubular adenoma, villous adenoma, hamartoma, or leiomyoma.

In one embodiment, the cancer is cancer of the pancreas.

More particularly, the cancer of the pancreas is ductal adenocarcinoma, insulinoma, gucagonoma, gastrinoma, carcinoid tumors, or vipoma.

In one embodiment, the cancer is bone cancer.

More particularly, the bone cancer is osteosarcoma, fibrosarcoma, malignant fibrous histiocytoma, chondrosarcoma, Ewing's sarcoma, malignant reticulum cell sarcoma, malignant giant cell tumor chordoma, osteocartiliginous exostoses, chondroblastoma, chondromyofibroma, or osteoid osteoma.

In one embodiment, the cancer is hematologic cancer.

More particularly, the hematologic cancer is myeloid leukemia, acute lymphoblastic leukemia, chronic lymphocytic leukemia, myeloproliferative diseases, multiple myeloma, or myelodysplastic syndrome.

In one embodiment, the cancer is skin cancer.

More particularly, the skin cancer is malignant melanoma, basal cell carcinoma, squamous cell carcinoma, or Karposi's sarcoma.

In one embodiment, the cancer is renal cancer.

More particularly, the renal cancer is a renal tumor.

In one embodiment, the cancer is breast cancer.

More particularly, the breast cancer is a breast tumor.

In one embodiment, the cancer is colon cancer.

More particularly, the colon cancer is a colon cancer tumor.

In one embodiment, the cancer is fallopian tube cancer.

More particularly, the fallopian tube cancer is fallopian tube carcinoma.

In one embodiment, the cancer is ovarian cancer.

More particularly, the ovarian cancer is ovarian carcinoma [serous cystadenocarcinoma, mucinous cystadenocarcinoma, unclassified carcinoma], granulosa-thecal cell tumors, Sertoli Leydig cell tumors, dysgerminoma, malignant teratoma), vulva (squamous cell carcinoma, intraepithelial carcinoma, adenocarcinoma, fibrosarcoma, or melanoma.

In another embodiment, the cancer is prostate cancer.

More particularly, the prostate cancer is adenocarcinoma or sarcoma.

In another embodiment, the prostate cancer is castration resistant prostate cancer (CRPC).

In another embodiment, the cancer is lung cancer.

More particularly, the lung cancer is bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, or inesothelioma.

The antitumor effect of the dosage form of the invention is measured using serological and/or radiographic methods available to the skilled practitioner. For serological methods, the relative concentration of a cancer biomarker is measured before and after administration of Compound 1 Form I, II, III, XXVIII, XXX, or XXXI. A positive response means that there is a lower serological concentration of the biomarker after treatment as compared to the concentration before treatment. As an example, for patients being treated for prostate cancer, particularly castration-resistant prostate cancer, the serological concentration of the biomarker PSA will be determined before, during, and after treatment. Patients can be assigned a PSA response according to the following criteria:

Complete Serological Response: PSA level less than 0.2 ng/mL measured for 2 consecutive measurements at least 4 weeks apart.

Serological Partial Response (PR): decline of PSA value, referenced to the pre-study level, by greater than or equal to 50% for 2 consecutive measurements at least 2 weeks apart.

PSA Stable Disease: Patients who do not meet the criteria for response (CR or PR) or serological progression Serological Progression (PD): is observed when the PSA demonstrates an increase that is more than 50% of nadir, taking as reference the lowest recorded PSA level since starting therapy. Two consecutive increases must be documented with each measurement obtained at least 2 weeks apart. On occasions, there may be an intermediate fluctuant value. In accordance with the Recommendations of the Prostate Cancer Clinical Trials Working Group this will not restart the evaluation period so long as the intermediate value was not below the previous nadir[18]. The date of first recorded increase (not defeated by a subsequent drop in PSA level to create a new nadir) will be deemed the date of progression. If a patient achieves a PSA that is less than 2 ng/mL, progression will only be deemed to have been confirmed once: (1) There has been an observed rise that is more than 50% of nadir since starting ADT; AND (2) The confirming increase was to a value that is more than 2.0 ng/mL (the unconfirmed and second increase may be a value that is less than 2.0 ng/mL but greater than 50% of nadir since starting ADT).

These serological response levels can be modified as needed based on the biomarker at issue.

In one embodiment, a complete serological response is observed in patients being treated with the dosage form. In another embodiment, a serological partial response is observed in patients being treated with the dosage form. In a further embodiment, stable disease is observed in patients being treated with the dosage form.

With respect to radiographic methods, radiographic disease progression is defined by RECIST 1.1 for soft tissue disease, or the appearance of two or more new bone lesions on bone scan. Progression in the absence of clear symptomatic worsening at the first scheduled reassessment after commencement of treatment requires a confirmatory scan at later point in time. Standard imaging procedures available to the skilled practitioner, including technetium bone scans and CT scans can be used to measure radiographic effect. Other radiographic methods such as NaF and FDG-PET may also be used to measure radiographic effect.

As indicated previously, the amount of Compound 1 Form I, II, III, XXVIII, XXX, or XXXI that is administered can be adjusted to avoid adverse events. For example, in one embodiment, a pharmaceutical dosage comprising 60 mg of Compound 1 Form I, II, III, XXVIII, XXX, or XXXI is administered to a patient that had one or more adverse events at a dosage greater than 60 mg.

In another embodiments, 60 mg of Compound 1 Form I, II, III, XXVIII, XXX, or XXXI is administered to a patient that had one or more adverse events at a pharmaceutical dosage between 80 mg and 160 mg.

In another embodiment, 60 mg of Compound 1 Form I, II, III, XXVIII, XXX, or XXXI is administered to a patient that had one or more adverse events at a dosage of 70 mg.

In another embodiment, 60 mg of Compound 1 Form I, II, III, XXVIII, XXX, or XXXI is administered to a patient that had one or more adverse events at a dosage of 80 mg.

In another embodiment, 60 mg of Compound 1 Form I, II, III, XXVIII, XXX, or XXXI is administered to a patient that had one or more adverse event at a dosage of 90 mg.

In another embodiment, 60 mg of Compound 1 Form I, II, III, XXVIII, XXX, or XXXI is administered to a patient that had one or more adverse events at a dosage of 100 mg.

In another embodiment, 60 mg of Compound 1 Form I, II, III, XXVIII, XXX, or XXXI is administered to a patient that had one or more adverse events at a dosage of 120 mg.

In another embodiment, 60 mg of Compound 1 Form I, II, III, XXVIII, XXX, or XXXI is administered to a patient that had one or more adverse events at a dosage of 130 mg.

In another embodiment, 60 mg of Compound 1 Form I, II, III, XXVIII, XXX, or XXXI is administered to a patient that had one or more adverse events at a dosage of 140 mg.

In another embodiment, 60 mg of Compound 1 Form I, II, III, XXVIII, XXX, or XXXI is administered to a patient that had one or more adverse events at a dosage of 150 mg.

In another embodiment, 60 mg of Compound 1 Form I, II, III, XXXVIII, XXX, or XXXI is administered to a patient that had one or more adverse events at a dosage of 160 mg.

In other embodiments, 60 mg of Compound 1 Form I, II, III, XXVIII, XXX, or XXXI is administered to a patient that had one or more adverse events at a pharmaceutical dosage of 140 mg or 100 mg.

In another embodiment, the pharmaceutical dosage comprising 40 mg of Compound 1 Form I, II, III, XXVIII, XXX, or XXXI is administered to a patient that had one or more adverse events at a dosage greater than 40 mg.

In another, 40 mg of Compound 1 Form I, II, III, XXVIII, XXX, or XXXI is administered to a patient that had one or more adverse events at a pharmaceutical dosage between 60 mg and 160 mg.

In another embodiment, 40 mg of Compound 1 Form I, II, III, XXVIII, XXX, or XXXI is administered to a patient that had one or more adverse events at a dosage of 50 mg.

In another embodiment, 40 mg of Compound 1 Form I, II, III, XXVIII, XXX, or XXXI is administered to a patient that had one or more adverse events at a dosage of 60 mg.

In another embodiment, 40 mg of Compound 1 Form I, II, III, XXVIII, XXX, or XXXI is administered to a patient that had one or more adverse events at a dosage of 70 mg.

In another embodiment, 40 mg of Compound 1 Form I, II, III, XXVIII, XXX, or XXXI is administered to a patient that had one or more adverse events at a dosage of 80 mg.

In another embodiment, 40 mg of Compound 1 Form I, II, III, XXVIII, XXX, or XXXI is administered to a patient that had one or more adverse events at a dosage of 90 mg.

In another embodiment, 40 mg of Compound 1 Form I, II, III, XXVIII, XXX, or XXXI is administered to a patient that had one or more adverse events at a dosage of 100 mg.

In another embodiment, 40 mg of Compound 1 Form I, II, III, XXVIII, XXX, or XXXI is administered to a patient that had one or more adverse events at a dosage of 120 mg of compound 1.

In another embodiment, 40 mg of Compound 1 Form I, II, III, XXVIII, XXX, or XXXI is administered to a patient that had one or more adverse events at a dosage of 130 mg.

In another embodiment, 40 mg of Compound 1 Form I, II, III, XXVIII, XXX, or XXXI is administered to a patient that had one or more adverse events at a dosage of 140 mg.

In another embodiment, 40 mg of Compound 1 Form I, II, III, XXVIII, XXX, or XXXI is administered to a patient that had one or more adverse events at a dosage of 150 mg.

In another embodiment, 40 mg of Compound 1 Form I, II, III, XXVIII, XXX, or XXXI is administered to a patient that had one or more adverse events at a dosage of 160 mg.

In another embodiment, 40 mg of Compound 1 Form I, II, III, XXVIII, XXX, or XXXI is administered to a patient that had one or more adverse events at a pharmaceutical dosage of 140 mg, 100 mg, or 60 mg.

In another embodiment, the pharmaceutical dosage comprising 20 mg of Compound 1 Form I, II, III, XXVIII, XXX, or XXXI is administered to a patient that had one or more adverse events at a dosage greater than 60 mg.

In another embodiment, 20 mg of Compound 1 Form I, II, III, XXVIII, XXX, or XXXI is administered to a patient that had one or more adverse events at a pharmaceutical dosage between 40 mg and 160 mg.

In another embodiment, 20 mg of Compound 1 Form I, II, III, XXVIII, XXX, or XXXI is administered to a patient that had one or more adverse events at a dosage of 30 mg.

In another embodiment, 20 mg of Compound 1 Form I, II, III, XXVIII, XXX, or XXXI is administered to a patient that had one or more adverse events at a dosage of 40 mg.

In another embodiment, 20 mg of Compound 1 Form I, II, III, XXVIII, XXX, or XXXI is administered to a patient that had one or more adverse events at a dosage of 50 mg.

In another embodiment, 20 mg of Compound 1 Form I, II, III, XXVIII, XXX, or XXXI is administered to a patient that had one or more adverse events at a dosage of 60 mg.

In another embodiment, 20 mg of Compound 1 Form I, II, III, XXVIII, XXX, or XXXI is administered to a patient that had one or more adverse events at a dosage of 70 mg.

In another embodiment, 20 mg of Compound 1 Form I, II, III, XXXVIII, XXX, or XXXI is administered to a patient that had one or more adverse events at a dosage of 80 mg.

In another embodiment, 20 mg of Compound 1 Form I, II, III, XXVIII, XXX, or XXXI is administered to a patient that had one or more adverse events at a dosage of 90 mg.

In another embodiment, 20 mg of Compound 1 Form I, II, III, XXVIII, XXX, or XXXI is administered to a patient that had one or more adverse events at a dosage of 100 mg.

In another embodiment, 20 mg of Compound 1 Form I, II, III, XXVIII, XXX, or XXXI is administered to a patient that had one or more adverse events at a dosage of 120 mg.

In another embodiment, 20 mg of Compound 1 Form I, II, III, XXVIII, XXX, or XXXI is administered to a patient that had one or more adverse events at a dosage of 130 mg.

In another embodiment, 20 mg of Compound 1 Form I, II, III, XXX VIII, XXX, or XXXI is administered to a patient that had one or more adverse events at a dosage of 140 mg.

In another embodiment, 20 mg of Compound 1 Form I, II, III, XXX VIII, XXX, or XXXI is administered to a patient that had one or more adverse events at a dosage of 150 mg.

In another embodiment, 20 mg of Compound 1 Form I, II, III, XXX VIII, XXX, or XXXI is administered to a patient that had one or more adverse events at a dosage of 160 mg.

In other embodiments, 20 mg of Compound 1 Form I, II, III, XXVIII, XXX, or XXXI is administered to a patient that had one or more adverse events at a pharmaceutical dosage of 140 mg, 100 mg, 60 mg, or 40 mg.

In some embodiments, the adverse event is one or more of diarrhea, stomatitis, palmar-plantar erythrodysesthesia syndrome (PPES), decreased weight, decreased appetite, nausea, fatigue, oral pain, hair color changes, dysgeusia, hypertension, abdominal pain, constipation, increased AST, increased ALT, lymphopenia, increased alkaline phosphatase, hypocalcemia, neutropenia, thrombocytopenia, hypophosphatemia, hyperbilirubinemia, perforations, fistulas, hemorrhage, thromboembolic events, wound complications, osteonecrosis of the jaw, proteinuria, reversible posterior leukoencephalopathy syndrome (RPLS), and embryo-fetal toxicity.

In some embodiments, the adverse event is Grade 1. In some embodiments, the adverse event is Grade 2. In some embodiments, the adverse event is Grade 3. In some embodiments, the adverse event is Grade 4. In some embodiments, the adverse event is Grade 5.

In one embodiment, treatment is temporarily suspended for a patient who had a Grade 4 adverse event. In another embodiment, upon resolution or improvement of the Grade 4 adverse event, the dose of compound 1 is resumed at the same or a reduced dosage. In some embodiments, resolution or improvement of the Grade 4 adverse event means returning to baseline. In other embodiments, resolution or improvement of the Grade 4 adverse event means resolution to a Grade 1 adverse event.

In one embodiment, treatment is temporarily suspended for a patient who had a Grade 3 adverse event. In another embodiment, upon resolution or improvement of the Grade 3 adverse event, the dose of compound 1 is resumed at the same or a reduced dosage. In some embodiments, resolution or improvement of the Grade 3 adverse event means returning to baseline. In other embodiments, resolution or improvement of the Grade 4 adverse event means resolution to a Grade 1 adverse event.

In one embodiment, treatment is temporarily suspended for a patient who had a Grade 2 adverse event. In another embodiment, upon resolution or improvement of the Grade 2 adverse event, the dose of compound 1 is resumed at the same or a reduced dosage. In some embodiments, resolution or improvement of the Grade 2 adverse event means returning to baseline. In other embodiments, resolution or improvement of the Grade 2 adverse event means resolution to a Grade 1 adverse event.

In one embodiment, treatment is temporarily suspended for a patient who had a Grade 1 adverse event. In another embodiment, upon resolution or improvement of the Grade 4 adverse event, the dose of compound 1 is resumed at the same or a reduced dosage. In some embodiments, resolution or improvement of the Grade 1 adverse event means returning to baseline.

In some embodiments, the dose is further reduced one or more times following the first reduction as a result of one or more adverse events. In one embodiment, the dose is reduced a first time. In another embodiment, the dose is reduced a first and second time. In another embodiment, the dose is reduced a first, second, and third time.

General Preparation Methods of Crystalline Solid Forms

Crystalline solid forms may be prepared by a variety of methods including, but not limited to, for example, crystallization or recrystallization from a suitable solvent mixture; sublimation; growth from a melt; solid state transformation from another phase; crystallization from a supercritical fluid; and jet spraying. Techniques for crystallization or recrystallization of crystalline solid forms of a solvent mixture include, but are not limited to, for example, evaporation of the solvent; decreasing the temperature of the solvent mixture; crystal seeding of a supersaturated solvent mixture of the compound and/or salt thereof; crystal seeding a supersaturated solvent mixture of the compound and/or a salt from thereof; freeze drying the solvent mixture; and adding antisolvents (countersolvents) to the solvent mixture. High throughput crystallization techniques may be employed to prepare crystalline solid forms including polymorphs.

Crystals of drugs, including polymorphs, methods of preparation, and characterization of drug crystals, are discussed in *Solid-State Chemistry of Drugs*, S. R. Byrn, R. R. Pfeiffer, and J. G. Stowell, $2^{nd}$ Edition, SSCI, West Lafayette, Ind. (1999).

In a crystallization technique in which solvent is employed, the solvent(s) are typically chosen based on one or more factors including, but not limited to, for example, solubility of the compound; crystallization technique utilized; and vapor pressure of the solvent. Combinations of solvents may be employed. For example, the compound may be solubilized in a first solvent to afford a solution to which antisolvent is then added to decrease the solubility of the Compound 1 in the solution and precipitate the formation of crystals. An antisolvent is a solvent in which a compound has low solubility.

In one method that can be used in preparing crystals, Compound 1 can be suspended and/or stirred in a suitable solvent to afford a slurry, which may be heated to promote dissolution. The term "slurry," as used herein, means a saturated solution of the compound, wherein such solution may contain an additional amount of compound to afford a heterogeneous mixture of compound and solvent at a given temperature.

Seed crystals may be added to any crystallization mixture to promote crystallization. Seeding may be employed to control growth of a particular polymorph and/or to control the particle size distribution of the solid product. Accordingly, calculation of the amount of seeds needed depends on the size of the seed available and the desired size of an average product particle as described, for example, in Programmed Cooling Batch Crystallizers," J. W. Mullin and J. Nyvlt, Chemical Engineering Science, 1971, 26, 3690377. In general, seeds of small size are needed to effectively control the growth of crystals in the batch. Seeds of small size may be generated by sieving, milling, or micronizing large crystals, or by microcrystallizing a solution. In the milling or micronizing of crystals, care should be taken to avoid changing crystallinity from the desired solid form (i.e., changing to an amorphous or other polymorphic form).

A cooled crystallization mixture may be filtered under vacuum and the isolated solid product washed with a suitable solvent, such as, for example, cold recrystallization solvent. After being washed, the product may be dried under a nitrogen purge to afford the desired solid form. The product may be analyzed by a suitable spectroscopic or analytical technique including, but not limited to, for example, differential scanning calorimetry (DSC); x-ray powder diffraction (XRPD); and thermogravimetric analysis (TGA) to assure the solid form of the compound has been formed. The resulting solid form may be produced in an amount greater than about 70 weight percent isolated yield, based on the weight of the compound originally employed in the crystallization procedure, and preferably greater than about 90 weight percent isolated yield. Optionally, the product may be delumped by being comilled or passed through mesh screen.

The features and advantages of this disclosure may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of this disclosure that are, for brevity reasons, described in the context of a single embodiment, may also be combined so as to form sub-combinations thereof. The disclosure is further illustrated by the following examples, which are not to be construed as limiting the disclosure in scope or spirit to the specific procedures described in them.

Synthesis

The solid compounds of the invention can be synthesized from readily available starting materials as described below and in the Examples. It will be appreciated that while specific process conditions (i.e., reaction temperatures, times, mole ratios of reactants, solvents, pressures, etc.) are given, other process conditions can also be used unless otherwise stated. Generally, the reactions are conducted in a suitable inert diluent, examples of which include, but are not limited to, methanol, ethanol, isopropanol, isobutanol, ethyl acetate, acetonitrile, dichloromethane, methyl t-butyl ether, and the like, and mixtures thereof, typically containing water. Upon completion of any of the foregoing reactions, the solid compounds can be isolated from the reaction mixture by any conventional means such as precipitation, concentration, centrifugation, and the like.

The Compound 1 employed in the invention can be readily prepared from commercially available starting materials and reagents using the procedures described in the Examples, or using the procedures described in WO 2005/030140, as well as in WO 2012/109510 and WO 2013/059788, each of which is incorporated by reference in its entirety.

The molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

EXAMPLES

The following examples illustrate the scope of the invention. The examples and preparations which follow are provided to enable those skilled in the art to more clearly understand and to practice the present invention. They should not be considered as limiting the scope of the invention, but merely as being illustrative and representative thereof.

Experimental Techniques

X-ray Powder Diffraction (XRPD)

XRPD analyses were performed using a Panalytical Xpert Pro diffractometer equipped with a Cu X-ray tube and a Pixcel detector system. The isothermal samples were analyzed in transmission mode and held between low density polyethylene films. The XRPD analysis program used an analysis range of 3-40°2θ, step size 0.013°, counting time 99 seconds, and an approximate run time of 22 minutes. Variable temperature samples were loaded into capillaries and temperature controlled using an Oxford Cryostream system. XRPD patterns were sorted, manipulated, and indexed using HighScore Plus 2.2c software.

Differential Scanning Calorimetry (DSC)

DSC analyses were carried out on a Perkin Elmer Jade Differential Scanning calorimeter. Accurately weighed samples were placed in crimped aluminum pans. Each sample was heated under nitrogen at a rate of 10° C./minute to a maximum of 300° C. Indium metal was used as the calibration standard. Temperatures were reported at the transition onset to the nearest 0.01 degree.

Hyper Differential Scanning Calorimetry (DSC)

Hyper DSC analyses were carried out on a Perkin Elmer Diamond Differential Scanning calorimeter. Accurately weighed samples were placed in crimped aluminum pans. Each sample was heated and cooled under helium over two cycles at a rate of 300° C./minute using a temperature range of −50 to 300° C. Indium metal was used as the calibration standard.

Hyper DSC allows the measurement of thermal events using very fast scanning rates. The fast scanning rate results in a much increased heat flow signal and therefore greatly increases sensitivity. This allows extremely low energy transitions, such as the glass transition temperature (Tg), to be identified and measured much more effectively.

Thermogravimetric Differential Thermal Analysis (TG/DTA)

Thermogravimetric analyses were carried out on a Mettler Toledo TGA/DSC1 STARe. The calibration standard was indium. Samples were placed in an aluminum sample pan, inserted into the TG furnace and accurately weighed. The heat flow signal was stabilized for one minute at 30° C., prior to heating to a maximum of 300° C. in a stream of nitrogen at a rate of 10° C./minute.

$^1$H/$^{13}$C Nuclear Magnetic Resonance Spectroscopy (NMR)

NMR analysis was carried out on either a Bruker 400 MHz or 500 MHz instrument in DMSO-d6.

Optical and Hot-Stage Microscopy

Microscopy analysis was carried out on an Olympus BX51 microscope. Photomicrographs of cabozantinib were obtained at objective lens magnifications ×10 using a polarized light source. Hot stage microscopy analyses were performed using a Linkam hot stage accessory. Solid samples were heated using pre-set temperature programs which included the selected ramp rate, final temperature, and interval hold times if required for individual samples.

Dynamic Vapor Sorption (DVS)

Dynamic Vapor Sorption (DVS) was performed using a Hiden Analytical Instruments IGAsorp Vapor Sorption Balance. Approximately 30 mg of sample was placed into a wire-mesh Vapor sorption balance pan, loaded into the IGAsorp Vapor sorption balance and held at 25° C.±0.1° C. The sample was subjected to a step profile from 0 to 90% RH at 10% increments, followed by desorption from 80% RH to 0% RH at 10% increments. The equilibrium criterion was set to 99.0% step completion within a minimum of 60 minutes and a maximum of 5 hours for each increment. The weight change during the sorption cycle was monitored, allowing for the hygroscopic nature of the sample to be determined. The data collection interval was in seconds.

Fourier Transfer Infra-Red (FTIR) Spectroscopy

Fourier Transform Infa-Red (FTIR) was performed using Attenuated Total Reflectance (ATR) on a Thermonicolet 370 Avatar Infra-Red Spectrometer equipped with an ATR Smart Golden Gate Accessory. A small portion of the sample was placed on the ATR crystal. The sample spectrum was collected in % Transmittance in the range of 650 cm$^{-1}$-4000 cm$^{-1}$, using a resolution of 4 cm$^{-1}$ and an acquisition of 20 scans.

Experiments

Preparation of Forms

Preparation of Compound 1 Form I

Compound 1 Form I was prepared by adding Compound 1 Form I (1 g) or amorphous material and THF (12 mL) to a flask and agitating at ambient temperature until dissolved. Water (about 20 mL) was added to the ambient temperature solution over approximately 2 hours, stirred for about 8 hours, and the solids were collected and dried. The material was fully characterized.

Preparation of Compound 1 Form II

Compound 1 Form I (1 g) and THF (12 mL) were added to a flask and agitated at ambient temperature until dissolved. Water (about 12 mL) was added to the ambient temperature solution over approximately 2 hours, stirred for about 8 hours, and the solids were collected and dried. The material was fully characterized.

Preparation of Compound 1 Form III

Compound 1 Form I (1 g) and THF (12 mL) were added to a flask and agitated at ambient temperature until dissolved. The contents of the flask were heated at a temperature from 30 to 50° C. and the pressure reduced to approximately 100 torr. After approximately one-half of the volume was removed by distillation, methanol was added to the flask to achieve the approximate starting volume. This distillation was repeated at least two times, and the contents of the flask returned to ambient temperature and pressure. The resulting solids were collected, dried, and fully characterized.

Preparation of Compound 1 Form XXVIII

Compound 1 Form I (150 mg) and 1-butanol (1 mL) were added to a vial and stirred at 5° C. for 7 days. The solids were recovered by filtration, air dried, and characterized. In another scale-up method, amorphous Compound 1 was slurried in nitromethane for 11 days, and the solids were collected, dried, and desolvated on a TG/DTA at 110° C.±30° C. for 15 minutes. The resulting solids were fully characterized.

Preparation of Compound 1 Form XXX

Amorphous Compound 1 (approximately 100 mg) was added to a vial which was placed unsealed inside a larger vial containing acetone. After 5 days, the sample was desolvated on the TG/DTA at 105° C. for 25 minutes, followed by desolvation at 100° C.±30° C. for 40 minutes to yield pattern XXX material. The material was fully characterized.

Preparation of Compound 1 Form XXXI

Compound 1 Form III (140 mg) and EtOH:water (44:56% v/v, 5.6 mL) were stirred in a sealed vial for 3 hours to allow for saturation. Compound 1 Form I (50 mg) and pattern XXXI cabozantinib (approximately 1-2 mg) were added, and the mixture was stirred for 3 days to allow for complete conversion to Compound 1 Form XXXI. The solid was recovered by vacuum filtration and dried on the filter with vacuum suction for 30 minutes prior to analysis by XRPD.

Synthesis of Amorphous Compound 1

Hyper DSC was performed in order to generate amorphous material from fast cooling of molten forms of Compound 1.

Amorphous Compound 1 was generated by melting Compound 1 followed by fast cooling. A thermogram taken from the second heating of a heat-cool-heat cycle demonstrates the presence of a Tg, observed at 99.19° C. (half-height value).

Amorphous Compound 1 was generated by melting Compound 1 Form II followed by fast cooling. A thermogram taken from the second heating of a heat-cool-heat cycle demonstrates the presence of a Tg, observed at 103.72° C. (half-height value).

Amorphous Compound 1 was generated by melting Compound 1 Form III followed by fast cooling. An expanded thermogram taken from the second heating of a heat-cool-heat cycle demonstrated the presence of a Tg, observed at 120.72° C. (half-height value), higher than was observed with Compound 1 Forms I or II, because in these forms, the solvent vapor generated plasticizes the amorphous state and lowers the Tg.

Amorphous Compound 1 was also generated on a 200 mg scale from Compound Form I, Compound 1 Form II, or Compound 1 Form III material by freeze-drying a filtered solution in dioxane. Compound 1 (200 mg) was dissolved in dioxane (20 mL), filtered through a 0.2 µm filter into a round-bottomed flask containing liquid nitrogen. The flask was rotated within a Dewar flask containing liquid nitrogen, forming frozen droplets inside the flask. The flask was lyophilized under vacuum (0.08 mbar) for 18 hours at 20° C. XRPD analysis displayed a halo pattern indicative of X-ray amorphous material (FIG. 1).

Data for Crystalline Solid Forms

X-ray powder diffraction (XRPD) data (CuKα, (°2θ±0.2 °2θ) for Compound 1 Forms I, II, III, XXVIII, XXX, and XXXI is summarized in Table 1.

TABLE 1

| Compound 1 | | | | | |
| --- | --- | --- | --- | --- | --- |
| Form I | Form II | Form III | Form XXVIII | Form XXX | Form XXXI |
| 10.1 | 6.4 | 7.0 | 6.5 | 7.2 | 5.0 |
| 11.9 | 11.6 | 7.8 | 9.5 | 7.5 | 10.0 |
| 12.9 | 12.1 | 9.4 | 11.8 | 10.0 | 11.9 |
| 14.4 | 12.6 | 11.1 | 12.3 | 12.0 | 13.0 |
| 16.0 | 12.9 | 12.6 | 13.0 | 12.4 | 14.4 |
| 23.0 | 14.8 | 14.1 | 15.5 | 13.5 | 16.1 |
| 24.7 | 14.9 | 15.5 | 16.9 | 15.8 | 19.9 |
|  | 18.0 | 17.3 | 17.7 | 19.8 | 21.4 |
|  | 18.8 | 22.3 | 19.1 |  | 23.8 |
|  | 20.2 | 24.3 | 21.7 |  |  |
|  |  |  | 22.3 |  |  |

Compound 1 Form I

The XRPD pattern obtained for Compound 1 Form is shown in FIG. 2. Thermogravimetric/Differential Thermal Analysis (TG/DTA) was performed to determine the thermal profile and associated % weight changes of Compound 1 Form I. As depicted in FIG. 3, weight loss of approximately 6.5% from 25-80° C. was noted, which corresponds to approximately 1.92 moles of water and confirms that Compound 1 Form I cabozantinib is a dihydrate. A second weight loss at temperatures greater than 200° C. corresponds to the initiation of decomposition of the material. Two endotherms were observed at onset temperature approximately 56.6° C. and 116.7° C. These correspond to the loss of water and subsequent melting of the dehydrated form respectively.

Figure 4:
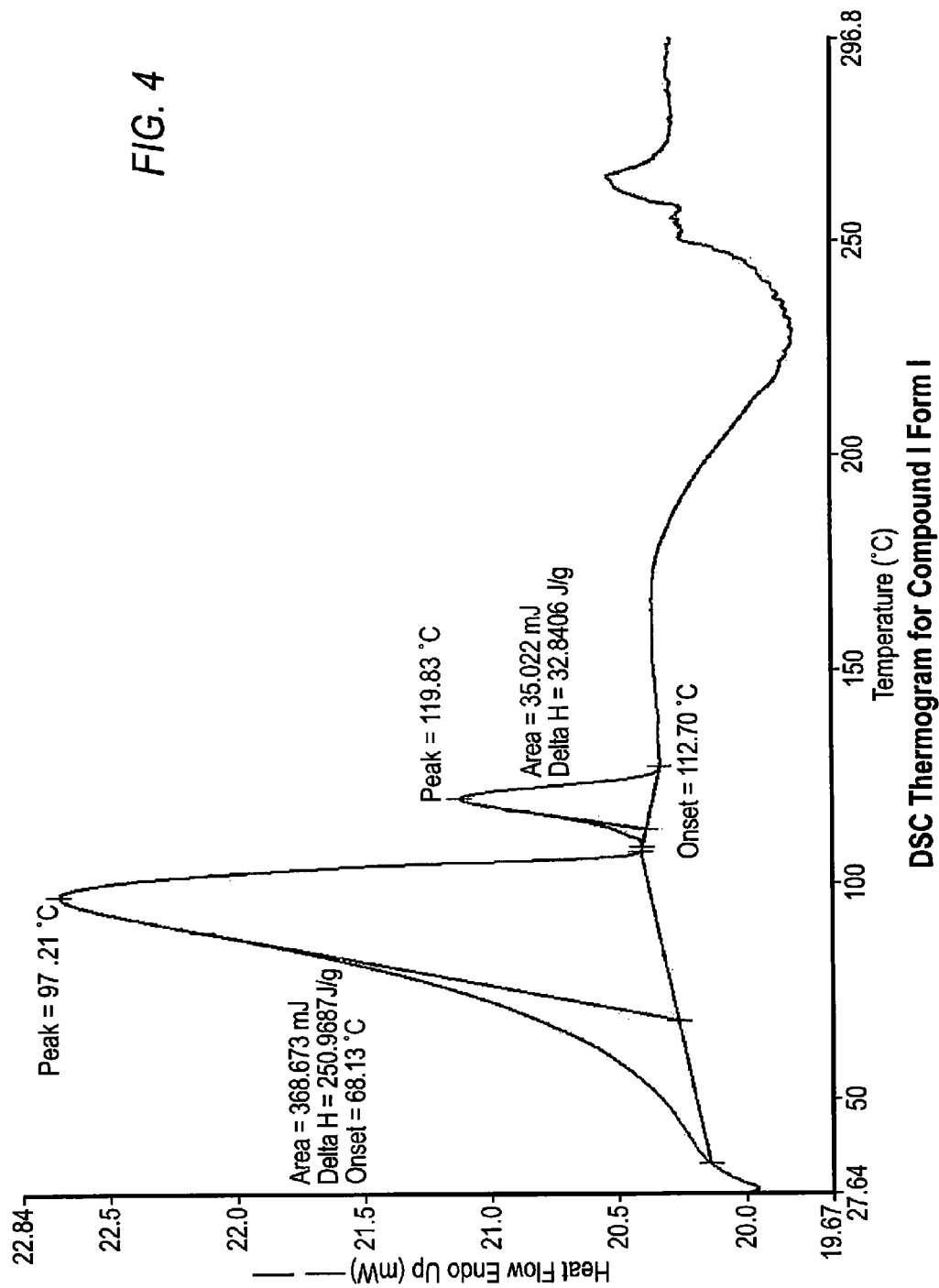
FIG. 4 shows the differential scanning calorimetry (DSC) thermogram for Compound 1 Form I, run from 30-300° C. at 10° C./min.

The DSC thermogram obtained for Compound 1 Form I at 10° C./min is shown in FIG. 4. The thermogram showed two endotherms, the first one at onset 68.13° C. due to loss of water, and the second endotherm at onset 112.70° C., which is the melting endotherm. This was confirmed visually by hot-stage microscopy.

Figure 5:
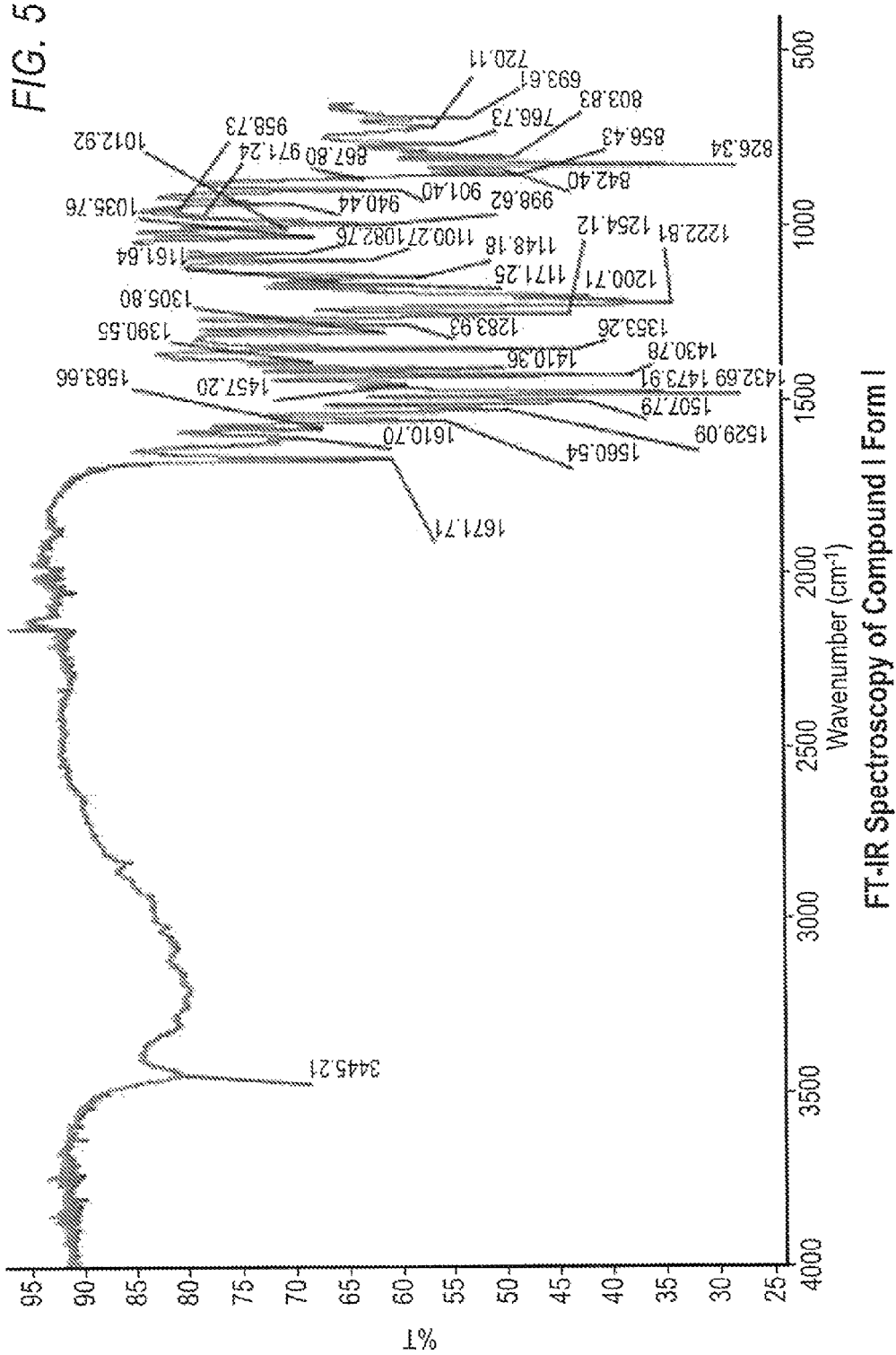
FIG. 5 shows the Fourier transfer infrared (FT-IR) spectrum for Compound 1 Form I.
Figure 6:
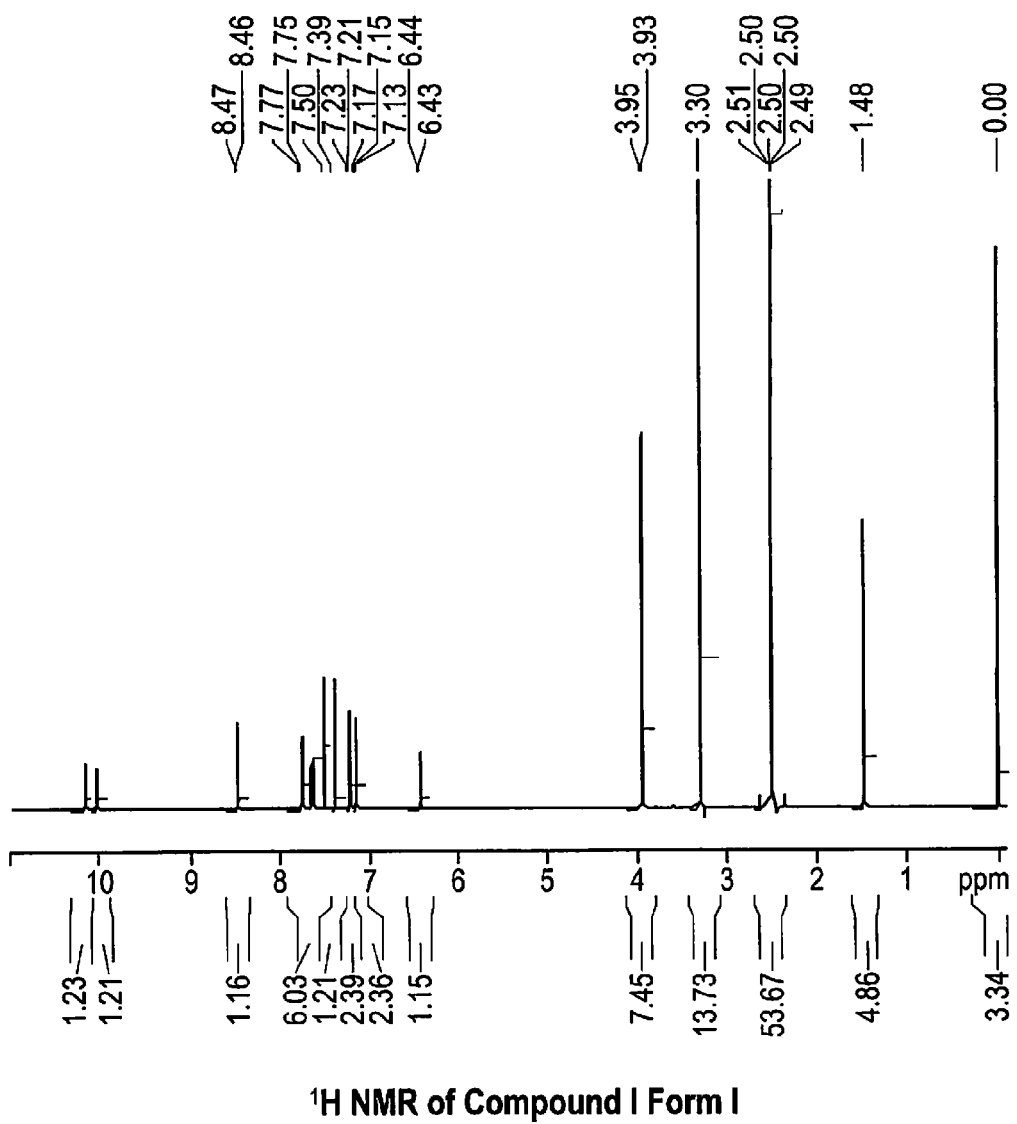
FIG. 6 shows the $^1$H nuclear magnetic resonance (NMR) spectrum for Compound 1 Form I.

The FT-IR spectrum obtained for the material is shown in FIG. 5 and includes stretches at 3445, 3200, 1671, 1561, 1508, 1433, 1431, 1353, 1254, 1223, 826 FTIR (cm$^{-1}$). The spectrum was shown to conform to the material structure with all expected functional groups present. The presence of water is clearly visible (broad, 3200 cm$^{-1}$), and peak shifts are significantly different to anhydrous Compound 1 Form III. $^1$H NMR (FIG. 6) conformed to structure.

Compound 1 Form II

The XRPD pattern obtained for Compound 1 Form II is shown in FIG. 7 and is indicative of a highly crystalline material. Thermogravimetric/Differential Thermal Analysis (TG/DTA) was performed to determine the thermal profile and associated % weight changes (FIG. 8).

Weight loss of approximately 9.8% was observed, and this was attributed to loss of a mixture of THF and water. A second weight loss at temperatures above 140° C. may be due to a mixture solvent loss and decomposition. The first endotherm, at onset 62.7° C., corresponds to the loss of solvent and/or water. The second at onset approximately 196.5° C. corresponds to the melt of an anhydrous form, later confirmed as low crystallinity Compound 1 Form III (see below).

The DSC thermogram (FIG. 9) showed two endotherms, the first at onset 71.47° C. was a broad peak corresponding to loss of solvent/water. An exotherm was observed at onset approximately 119.8° C., which suggests recrystallization to another form. A second endotherm was noted at onset 206.83° C., which corresponds to the melting point of Compound 1 Form III.

$^1$H NMR (FIG. 10) of Compound 1 Form II conforms to structure and shows the presence of THF (0.4 mole equivalents). This implies that 5.5% w/w of weight loss from TGA can be attributed to THF and the remainder to water (4.3% w/w, or approximately 1.2 mol eq).

Compound 1 Form III

The XRPD pattern for Compound 1 Form III is shown in FIG. 11 and is indicative of a highly crystalline material. Thermogravimetric/Differential Thermal Analysis (TG/DTA) was performed to determine the thermal profile and associated % weight changes of Compound 1 Form III (FIG. 12).

No weight loss was observed below 200° C., suggesting as Compound 1 Form III is an anhydrous material. A melting endotherm was observed at onset temperature 220.37° C. Weight loss due to decomposition was also observed above this point. The DSC thermogram obtained for Compound 1 Form III (FIG. 13) confirmed the melting onset at 220.59° C. Hot stage microscopy showed the onset of melting between 220° C. and 230° C., with the material completely molten by 235° C.

Figure 14:
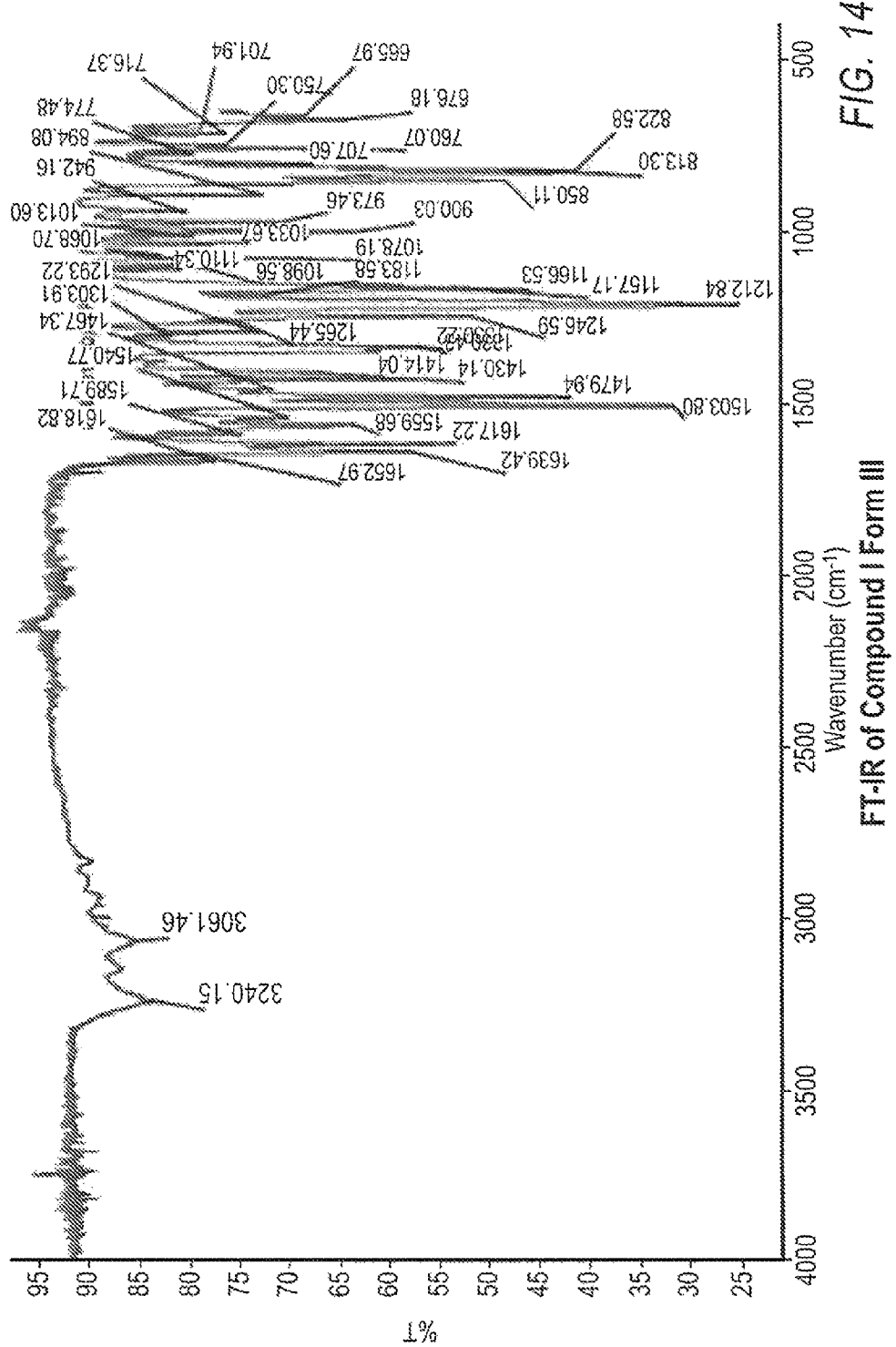
FIG. 14 shows the Fourier transfer infrared (FT-IR) spectrum for Compound 1 Form III.
Figure 15:
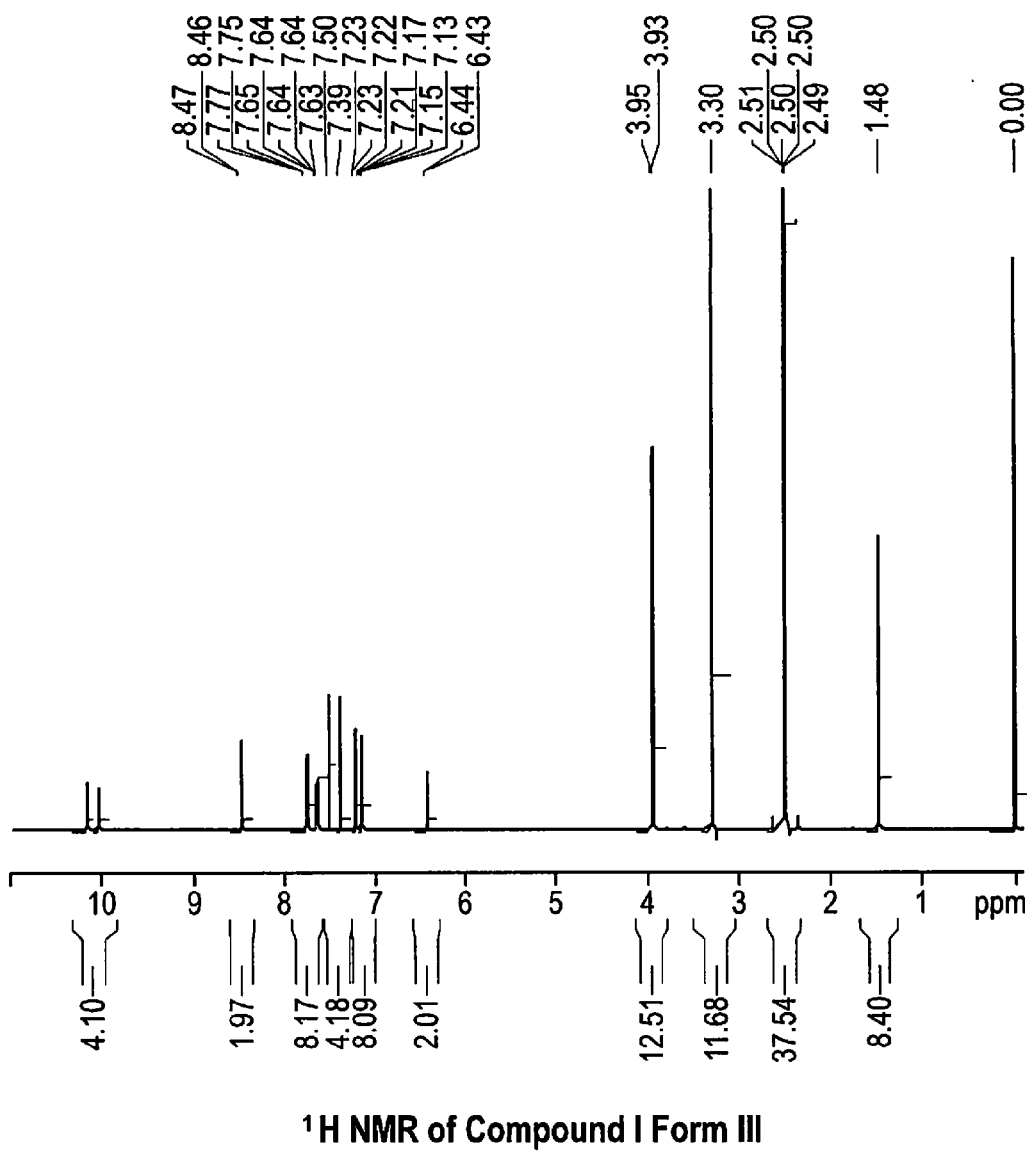
FIG. 15 shows the $^1$H nuclear magnetic resonance (NMR) spectrum for Compound 1 Form III.

$^1$H NMR (DMSO-d6, FIG. 15) conformed to structure and showed an absence of solvent. The FT-IR spectrum obtained for the material is shown in FIG. 14 and was shown to conform to the material structure with all expected functional groups present. FTIR (cm$^{-1}$): 3240, 3061, 1639, 1560, 1504, 1480, 1430, 1213, 1165, 850, 822.

Compound 1 Form XXVIII

The XRPD for Compound 1 Form XXVIII is shown in FIG. 16. The intense narrow peaks are indicative of a highly crystalline material. Polarized light microscopy showed birefringent crystals with particle size generally less than 10 µm.

TG/DTA (FIG. 17) showed no weight loss from 25° C. to 180° C., confirming that the material was an anhydrous form. DSC (FIG. 18) showed an initial endothermic event at onset 190.62° C., a recrystallization exotherm at onset 193.65° C. and another endotherm at onset 205.83° C. These results indicate that Compound 1 Form XXVIII melts and recrystallizes to Compound 1 Form III which subsequently melts. The melting onset is lower than that observed for pure Compound 1 Form III (onset 220.59° C.), most likely due to lower crystallinity.

Hyper DSC was performed in order to generate amorphous material from fast cooling of molten Compound 1 Form XXVIII and determine the temperature of glass transition (Tg) during the reheat cycle. The thermogram demonstrates the presence of a Tg, observed during the second heating of a heat-cool-heat cycle at 120.85° C. (half-height value). The Tg is consistent with Compound 1 Form XXVIII being an anhydrous Form, as it is similar to the Tg of Compound 1 Form III material.

¹H NMR (FIG. 20) of Compound 1 Form XXVIII showed the material to conform to structure and contain no solvent. Infra-red spectroscopy carried out on Compound 1 Form XXVIII (FIG. 19) was broadly similar to Compound 1 Form III, except in the 1700-1500 cm⁻¹ region. Typically associated with carbonyl stretching, this implies differences in the hydrogen bonding network. FTIR (cm⁻¹): 3038, 1686, 1531, 1504, 1480, 1350, 1213, 994, 856, 831.

Compound 1 Form XXX

The XRPD pattern for Compound 1 Form XXX, shown in FIG. 21, is indicative of a crystalline material. Polarized light microscopy confirms that the material is crystalline with some aggregation or agglomeration present.

Thermal analysis (TG/DTA) (FIG. 22) did not show significant weight loss and confirmed Compound 1 Form XXX was an anhydrous form. The onset of melting (117.9° C.) was slightly higher than that observed by DSC (FIG. 23), which showed an initial melt at onset 110.6° C., followed by a recrystallization event to Compound 1 Form III at onset 136.25° C. and a final melt at onset 205.64° C. As was the case for other recrystallization events, the Compound 1 Form III had a lower onset temperature as a result of lower crystallinity.

¹H NMR (FIG. 25) of Compound 1 Form XXX showed the material to conform to structure and contain ~1.1% w/w (0.1 mol eq) of residual acetone. Several attempts to reduce this solvent level using heat, vacuum drying, and humid drying were unsuccessful and suggested that some acetone remains trapped within the crystal structure. Infra-red spectroscopy (FIG. 24) differs from Compound 1 Form III and Compound 1 Form XXVIII in the carbonyl stretch region. The residual acetone carbonyl can be seen at 1717 cm-1, which is comparable to liquid acetone (1715 cm-1) and implies that the acetone is not hydrogen bonded within the crystal structure in Compound 1 Form XXX. FTIR (cm⁻¹): 3250, 1652, 1504, 1480, 1432, 1349, 1211, 1197, 995, 850, 821.

Compound 1 Form XXXI

The XRPD of Compound 1 Form XXXI (FIG. 26) is indicative of crystalline material. Thermal analysis (TG/DTA) (FIG. 27) showed two endothermic events; the first at onset 72.7° C. with an associated weight loss of 6.61% (1.97 mol equiv of water) was due to dehydration and indicates that Compound 1 Form XXXI is a dihydrate.

The hygroscopicity and the sorption properties of Compound 1 Form XXXI were determined using Dynamic Vapor Sorption (DVS). The program differed from that used for Compound 1 Form I in that the sample was dried at 0% RH prior to performing sorption and desorption. The isotherm showed the material lost −7% weight on drying to 0% RH, consistent with loss of 2 mol eq of water.

The DSC thermogram (FIG. 28) obtained for Compound 1 Form XXXI was complex and showed three endothermic events occurring between −67° C. and −130° C.

¹H NMR (FIG. 30) of Compound 1 Form Compound 1 XXXI showed the material to conform to structure. Infra-red spectroscopy (FIG. 29) conformed to the spectrum of Compound 1 Form I (FIG. 5) within experimental error. FTIR (cm⁻¹): 3444, 3251, 1672, 1530, 1507, 1483, 1430, 1354, 1256, 1223, 1148, 1000, 856, 843, 826.

Compound 1 Amorphous Form

The XRPD for Compound 1 Amorphous Form is shown in FIG. 1. The hygroscopicity and the sorption properties of Compound 1 Amorphous Form were determined using Dynamic Vapor Sorption (DVS). The sample was dried at 0% RH prior to performing sorption and desorption. The isotherm showed the material exhibits slow uptake of moisture from 0% RH to 60% RH. The rate of uptake of moisture increased from 60% RH to 90% RH. The isotherm showed the total weight gain observed between 0% RH and 80% RH to be 4% w/w which indicated that the sample was hygroscopic, according to the European Pharmacopoeia classification. The rate of desorption was slower than the rate of sorption, as hysteresis was observed. All of the moisture adsorbed was lost upon return to 0% RH. XRPD of the sample post DVS confirmed that no crystallization had occurred (FIG. 1).

The physical stability of amorphous material was assessed under a range of stress conditions including temperature stress, relative humidity (RH), and exposure to selected organic vapors. Surprisingly, the material was stable to heat stressing at 100° C. for 4 days (i.e. below Tg of 120° C.). Exposure to relative humidity between 23% and 98% for 7-10 days induced no crystallization. From DVS, a water uptake of approximately 5% was observed at 90% RH and thus the plasticizing effect of water can be estimated from the Fox equation. This suggests that the amorphous form should have a glass transition of approximately 87° C. at 90% RH. A Tg over 100° C. coupled with the above stress data reveal that amorphous Compound 1 contains an exceptional combination of favorable physical attributes that provide utility in a variety of drug product formulations.

Other Embodiments

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The invention claimed is:

1. A crystalline solid form of Compound 1:

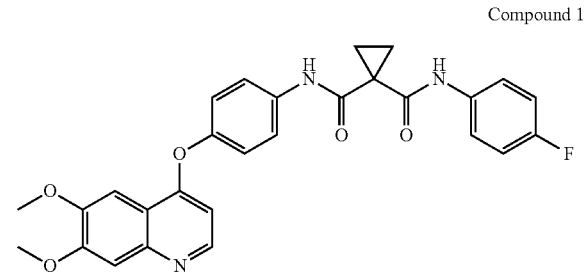 [SMILES: COc1cc2nccc(Oc3ccc(NC(=O)C4(C(=O)Nc5ccc(F)cc5)CC4)cc3)c2cc1OC]

Compound 1 wherein said crystalline solid form is in Form III and said Form III is characterized by an x-ray powder diffraction pattern (CuKα) comprising peaks at 7.0, 7.8, 11.1, and 14.1 (°2θ±0.2 °2θ), or at 9.4, 12.6, 22.3, and 24.3 (°2θ±0.2°2θ), or at 7.0, 7.8, 9.4, 11.1, 12.6, 14.1, 22.3, and 24.3 (°2θ±0.2 °2θ), wherein measurement is at room temperature.

2. The crystalline solid form of Compound 1 designated as Compound 1 Form III as recited in claim 1 wherein said Form III is characterized by an x-ray powder diffraction pattern (CuKα) comprising peaks at 7.0, 7.8, 11.1, and 14.1 (°2 θ±0.2°2θ), wherein measurement is at room temperature.

3. The crystalline solid form of Compound 1 designated as Compound 1 Form III as recited in claim 1 wherein said Form III is characterized by an x-ray powder diffraction pattern (CuKα) comprising peaks at 9.4, 12.6, 22.3, and 24.3 (°2 θ±0.2°2θ), wherein measurement is at room temperature.

4. The crystalline solid form of Compound 1 designated as Compound 1 Form III as recited in claim 1 wherein said Form III is characterized by an x-ray powder diffraction pattern (CuKα) comprising peaks at 7.0, 7.8, 9.4, 11.1, 12.6, 14.1, 22.3, and 24.3 (°2 θ±0.2°2θ), wherein measurement is at room temperature.

5. The crystalline solid form of Compound 1 designated as Compound 1 Form III as recited in claim 4 wherein said Form III is characterized by an x-ray powder diffraction pattern (CuKα) further comprising peaks at 15.5 and 17.3 (°2 θ±0.2°2θ) wherein measurement is at room temperature.

6. The crystalline solid form of Compound 1 designated as Compound 1 Form III as recited in claim 1 wherein said Form III is characterized by an x-ray powder diffraction pattern (CuKα) substantially in accordance with the pattern shown in FIG. 11.

7. A pharmaceutical composition comprising a therapeutically effective dose of a substantially pure crystalline solid form of Compound 1 designated as Compound 1 Form III as recited in claim 1 and a pharmaceutically acceptable carrier.

8. A pharmaceutical formulation comprising:

| Ingredient | (% w/w) |
|---|---|
| Compound 1 Solid Form III as recited in claim 1 | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |
| Croscarmellose Sodium | 3.00 |
| Magnesium Stearate | 0.75 |
| Total | 100.00. |

9. A pharmaceutical formulation comprising:

| Ingredient | (% w/w) |
|---|---|
| Compound 1 Solid Form III as recited in claim 1 | 25.0-33.3 |
| Microcrystalline Cellulose | q.s |
| Hydroxypropyl Cellulose | 3 |
| Poloxamer | 0-3 |
| Croscarmellose Sodium | 6.0 |
| Colloidal Silicon Dioxide | 0.5 |
| Magnesium Stearate | 0.5-1.0 |
| Total | 100. |

10. A pharmaceutical formulation comprising:

| Ingredient | Theoretical Quantity (mg/unit dose) |
|---|---|
| Compound 1 Solid Form III as recited in claim 1 | 100.0 |
| Microcrystalline Cellulose PH-102 | 155.4 |
| Lactose Anhydrous 60M | 77.7 |
| Hydroxypropyl Cellulose, EXF | 12.0 |
| Croscarmellose Sodium | 24 |
| Colloidal Silicon Dioxide | 1.2 |
| Magnesium Stearate (Non-Bovine) | 3.0 |
| Opadry Yellow | 16.0 |
| Total | 416. |

11. A pharmaceutical formulation comprising:

| Ingredient | % w/w |
|---|---|
| Compound 1 Solid Form III as recited in claim 1 | 31.7 |
| Microcrystalline Cellulose (Avicel PH-102) | 38.9 |
| Lactose Anhydrous (60M) | 19.4 |
| Hydroxypropyl Cellulose (EXF) | 3.0 |
| Croscarmellose Sodium (Ac-Di-Sol) | 6.0 |
| Colloidal Silicon Dioxide | 0.3 |
| Magnesium Stearate | 0.75 |
| Opadry Yellow Film Coating which includes: HPMC 2910/Hypromellose 6 cp Titanium dioxide Triacetin Iron Oxide Yellow. | 4.00 |

* * * * *

UNITED STATES PATENT AND TRADEMARK OFFICE
CERTIFICATE OF CORRECTION

PATENT NO. : 10,501,418 B2
APPLICATION NO. : 15/118738
DATED : December 10, 2019
INVENTOR(S) : Dana T. Aftab et al.

Page 1 of 1

It is certified that error appears in the above-identified patent and that said Letters Patent is hereby corrected as shown below:

In the Specification
In Column 19, Line 18, please delete "XXXVIII" and replace with --XXVIII--.
In Column 22, Line 14, please delete "XXXVIII" and replace with --XXVIII--.
In Column 23, Line 24, please delete "XXXVIII" and replace with --XXVIII--.
In Column 23, Line 39, please delete "XXX VIII" and replace with --XXVIII--.
In Column 23, Line 42, please delete "XXX VIII" and replace with --XXVIII--.
In Column 23, Line 45, please delete "XXX VIII" and replace with --XXVIII--.

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*